US012774333B2

(12) United States Patent
Liu et al.

(10) Patent No.: US 12,774,333 B2
(45) Date of Patent: Oct. 27, 2026

(54) COMPOSITIONS AND METHODS FOR MAKING AND USING MULTISPECIFIC ANTIBODIES

(71) Applicant: The Regents of the University of California, Oakland, CA (US)

(72) Inventors: Bin Liu, San Francisco, CA (US); Shanshan Lang, San Francisco, CA (US); Yang Su, San Francisco, CA (US); Scott Bidlingmaier, San Francisco, CA (US); Nam-Kyung Lee, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1132 days.

(21) Appl. No.: 17/639,225

(22) PCT Filed: Sep. 9, 2020

(86) PCT No.: PCT/US2020/049914
§ 371 (c)(1),
(2) Date: Feb. 28, 2022

(87) PCT Pub. No.: WO2021/050527
PCT Pub. Date: Mar. 18, 2021

(65) Prior Publication Data

US 2022/0411508 A1 Dec. 29, 2022

Related U.S. Application Data

(60) Provisional application No. 62/897,598, filed on Sep. 9, 2019.

(51) Int. Cl.
*C07K 16/00* (2006.01)
*C07K 16/28* (2006.01)

(52) U.S. Cl.
CPC ...... *C07K 16/2818* (2013.01); *C07K 16/2827* (2013.01); *C07K 16/2896* (2013.01); *C07K 2317/21* (2013.01); *C07K 2317/526* (2013.01); *C07K 2317/55* (2013.01); *C07K 2317/92* (2013.01); *C07K 2319/20* (2013.01)

(58) Field of Classification Search
None
See application file for complete search history.

(56) References Cited

U.S. PATENT DOCUMENTS

| | | | | |
|---|---|---|---|---|
| 2006/0063209 A1 | 3/2006 | Meares et al. | | |
| 2007/0274985 A1 | 11/2007 | Dubel et al. | | |
| 2010/0256338 A1 | 10/2010 | Brinkmann et al. | | |
| 2015/0307628 A1* | 10/2015 | Kim | C07K 16/468 | 435/69.6 |
| 2020/0172619 A1* | 6/2020 | Richter | C07K 16/40 | |
| 2022/0002432 A1* | 1/2022 | Liu | A61K 45/06 | |
| 2023/0145060 A1* | 5/2023 | Julien | A61K 49/0002 | 424/192.1 |

FOREIGN PATENT DOCUMENTS

| | | |
|---|---|---|
| WO | WO-2019/099374 A2 | 5/2019 |
| WO | WO-2019/104279 A1 | 5/2019 |

OTHER PUBLICATIONS

Spiess et al. Alternative molecular formats and therapeutic applications for bispecific antibodies. Molecular Immunology 2015, 67, 95-106.*
Ha et al. (2016) Immunoglobulin Fc Heterodimer Platform Technology: From Design to Applications in Therapeutic Antibodies and Proteins. Front. Immunol. 7:394, p. 1-16.*
Brinkmann et al. The making of bispecific antibodies. MABS 2017, vol. 9, No. 2, 182-212.*
Krah et al. Engineering bispecific antibodies with defined chain pairing. New Biotechnology 39 (2017) 167-173.*
Liu et al. (2017) Fc Engineering for Developing Therapeutic Bispecific Antibodies and Novel Scaffolds. Front. Immunol. 8:38. p. 1-15.*
Wranik et al. (2012) LUZ-Y, a Novel Platform for the Mammalian Cell Production of Full-length IgG-bispecific Antibodies. The Journal of Biological Chemistry, vol. 287, No. 52, pp. 43331-43339.*
Brinkmann, U. et al. (2017). "The making of bispecific antibodies," MAbs 9(2):182-212.
Extended European Search Report mailed on Aug. 29, 2023, for EP Patent Application No. 20864086.2, 10 pages.
International Search Report mailed on Jan. 6, 2021, for PCT Application No. PCT/US2020/049914, filed Sep. 9, 2020, 4 pages.
Lee, N.-K. et al. (Jan. 15, 2018). "Cell-type specific potent Wnt signaling blockade by bispecific antibody," *Sci Rep* 8:(1):766.
Lee, N.-K. et al. (Jun. 2019, e-published Apr. 8, 2019). "Manipulation of Cell-Type Selective Antibody Internalization by a Guide-Effector Bispecific Design," *Mol Cancer Ther* 18(6):1092-1103.
Written Opinion mailed on Jan. 6, 2021, for PCT Application No. PCT/US2020/049914, filed Sep. 9, 2020, 4 pages.

* cited by examiner

*Primary Examiner* — Ilia I Ouspenski
(74) *Attorney, Agent, or Firm* — Mintz Levin Cohn Ferris Glovsky and Popeo, P.C.

(57) ABSTRACT

The present disclosure relates generally to compositions and methods useful for the production of engineered antibodies having (i) multiple antigen-binding specificities and (ii) Fc regions that have been modified to promote heterodimer formation between heavy chains from antibodies with different specificities. Also provided are recombinant cells, recombinant nucleic acids encoding such engineered antibodies, as well as pharmaceutical compositions containing same.

22 Claims, 25 Drawing Sheets

Specification includes a Sequence Listing.

Single-chain IgG Sequence:

(sc36TMB linker)

(Light chain) -GLVPRGSGSGGGSGGGSEGGGSEGGGSEGGGSEGGGSGGGSGGLVPRGS- (heavy chain)

Thrombin

→

37° 2h (Light chain)-GLVPR + GS-(heavy chain)

FIG. 7

COMPOSITIONS AND METHODS FOR MAKING AND USING MULTISPECIFIC ANTIBODIES

CROSS-REFERENCE TO RELATED APPLICATIONS

The present application is a U.S. National Phase Application of PCT International Application No. PCT/US2020/049914, filed on Sep. 9, 2020, designating the United States of America, which is an International Application of and claims the benefit of priority to U.S. Provisional Patent Application Ser. No. 62/897,598, filed on Sep. 9, 2019. The disclosure of the above-referenced application is herein expressly incorporated by reference it its entirety, including any drawings.

STATEMENT REGARDING FEDERALLY SPONSORED R&D

This invention was made with government support under grant nos. R01 CA118919, R01 CA129491, R01 CA171315, and R01 CA223767 awarded by The National Institutes of Health. The government has certain rights in the invention.

INCORPORATION OF THE SEQUENCE LISTING

The present application is being filed along with a Sequence Listing in electronic format. The material in the accompanying Sequence Listing is hereby incorporated by reference into this application. The accompanying Sequence Listing text file, named "048536-647N01US_SequenceListing_ST25.txt," was created on Feb. 25 2022 and is 182 KB

FIELD

The present disclosure relates generally to the field of antibody engineering and particularly relates to multispecific antibodies that specifically bind to two or more different target antigens or epitopes. The disclosure also provides compositions and methods useful for producing such multispecific antibodies and pharmaceutical compositions containing the same.

BACKGROUND

Antibody constructs having more than one binding specificities have been reported to have several advantages compared to antibodies and antibody fragments having only one single binding site, such as an improved potency, multispecificity, multifunctionality. Compared to traditional monospecific antibodies that specifically recognize one ligand, multispecific antibodies can recognize two or more ligands and thus may provide an advantage in co-engaging different cell types, creating synthetic specificity, altering internalization dynamics, synergistically neutralizing virus and toxin, and simultaneously block multiple signaling pathways to maximize therapeutic benefits.

However, the production and use of multispecific antibodies has been hindered by the difficulty of obtaining multispecific antibodies in sufficient quantity and purity for both preclinical and clinical studies. A common problem in multispecific antibody generation is how to properly pair heavy and light chains from different specificities. For example, traditional production of full-length bispecific antibodies is typically based on the co-expression of two immunoglobulin heavy chain-light chain pairs, where the two chains have different specificities. The intrinsic tendency of the Fc portion of the antibody molecule to homodimerize leads to the formation of complex mixtures of up to 10 different IgG molecules consisting of various combinations of heavy and light chains, of which only one has the correct bispecific structure. In addition, purification of the correct molecule, which is usually done by affinity chromatography steps, is rather cumbersome, and the product yields are low. Thus, the production of a bispecific antibody molecule with the two Fab arms engineered to bind two different targets using traditional hybridoma techniques is challenging.

Another traditional method for multispecific antibody production is chemical conjugation of two antibodies or their fragments having different specificities. However, this method has been reported to be complex, and the chemical modification process may inactivate the antibody or promote aggregation. In addition, in the manufacture of multispecific antibodies, it is desirable to increase the yields of the desired multispecific antibodies. Because purification from undesired products remains difficult, the resulting low yield and poor quality of multispecific antibody make this process unsuitable for the large scale production required for clinical development. In addition, these molecules may not maintain the traditional antibody conformation.

In view of different problems and aspects of multispecific antibodies such as, e.g. pharmacokinetic and biological properties, stability, aggregation, expression yield, there remains a need in the art for alternative multispecific variant antibodies which have been modified to select for heterodimers with an increased stability and purity.

SUMMARY

Provided herein, inter alia, are compositions and methods concerning the production of engineered antibodies having (i) multiple antigen-binding specificities and (ii) Fc regions that have been modified to promote heterodimer formation between heavy chains from two different specificities. More particularly, provided herein are engineered antibodies having (i) two singe-chain antigen binding fragments specific for two different epitopes and (ii) Fc regions associated with one another via an interface which has been modified to promote heterodimer formation. Also provided are recombinant nucleic acids encoding at least one single-chain polypeptide chain of such engineered antibodies, recombinant cells including at least one recombinant nucleic acid as disclosed herein, as well as pharmaceutical compositions containing same.

In one aspect, provided herein are various engineered antibodies including a first and a second polypeptide chain, each of the first and second polypeptide chains including: (a) a single-chain antigen-binding (scFab) fragment which includes, in N-terminal to C-terminal direction, (i) a light chain variable domain (VL); (ii) a light chain constant domain (CL); (iii) a removable linker; (iv) a heavy chain variable domain (VH); and (v) a heavy chain constant domain CH1, wherein the scFab fragments of the first and second polypeptide chains have specificity for different antigens; and (b) an antibody Fc region N-terminally linked to the scFab fragment in (a), wherein the Fc regions of the first and a second polypeptide chains are associated with one another via an interface which has been modified to promote heterodimer formation.

In another aspect, provided herein are various engineered antibodies including a first and a second polypeptide chain, each of the first and second polypeptide chains including: (a) a single-chain antigen-binding (scFab) fragment which includes, in N-terminal to C-terminal direction, (i) a light chain variable domain (VL); (ii) a light chain constant domain (CL); (iii) a removable linker; (iv) a heavy chain variable domain (VH); and (v) a heavy chain constant domain CH1, wherein the scFab fragments of the first and second polypeptide chains have specificity for different antigens, and optionally wherein the N-terminus of the first polypeptide chain and/or the second polypeptide chain is operably linked to one or more additional scFab fragments having specificity for further antigens; and (b) an antibody Fc region N-terminally linked to the scFab fragment in (a), wherein the Fc regions of the first and a second polypeptide chains are associated with one another via an interface which has been modified to promote heterodimer formation.

In another aspect, provided herein are various engineered antibodies including a first and a second polypeptide chain, each of the first and second polypeptide chains including: (a) a single-chain antigen-binding (scFab) fragment which includes, in N-terminal to C-terminal direction, (i) a light chain variable domain (VL); (ii) a light chain constant domain (CL); (iii) a removable linker; (iv) a heavy chain variable domain (VH); and (v) a heavy chain constant domain CH1, wherein the scFab fragments of the first and second polypeptide chains have specificity for different antigens, and optionally wherein the C-terminus of the first polypeptide chain and/or the second polypeptide chain is operably linked to one or more additional scFab fragments having specificity for further antigens; and (b) an antibody Fc region N-terminally linked to the scFab fragment in (a), wherein the Fc regions of the first and a second polypeptide chains are associated with one another via an interface which has been modified to promote heterodimer formation.

Non-limiting exemplary embodiments of the disclosed engineered antibodies of the disclosure include one or more of the following features. In some embodiments, each additional scFab fragment including, in N-terminal to C-terminal direction, a VL domain, a CL domain, a removable linker, a VH domain, and a CH1 domain. In some embodiments, the removable linker includes one or more proteolytic cleavage sites. In some embodiments, the one or more proteolytic cleavage sites are positioned within the sequence of the removable linker and/or flanking at either end of the removable linker. In some embodiments, the one or more proteolytic cleavage sites can be cleaved by a protease or an endopeptidase. In some embodiments, at least one of the one or more proteolytic cleavage sites can be cleaved by a protease selected from the group consisting of thrombin, PreScission™ protease, and tobacco etch virus (TEV) protease. In some embodiments, the protease is thrombin. In some embodiments, the removable linker includes the polypeptide sequence of SEQ ID NO: 80. In some embodiments, at least one of the one or more proteolytic cleavage sites can be cleaved by an endopeptidase selected from the group consisting of trypsin, chymotrypsin, elastase, thermolysin, pepsin, glutamyl endopeptidase, or neprilysin.

In some embodiments, the removable linker further includes one or more affinity tags. In some embodiments, the one or more affinity tags is selected from the group consisting of polyhistidine (poly-His) tags, Hemagglutinin (HA) tags, AviTag™, protein C tags, FLAG tags, Strep-tag® II, and Twin-Strep-tag®, glutathione —S-transferase (GST), C-myc tag, chitin-binding domain, Streptavidin binding proteins (SBP), maltose binding protein (MBP), cellulose-binding domains, calmodulin-binding peptides, and S-tags. In some embodiments, at least one of the one or more affinity tags includes a poly-His tag or a Twin-Strep-tag®. In some embodiments, the removable linkers of the scFab fragments of the first and second polypeptide chains includes the same affinity tags. In some embodiments, the removable linkers of the scFab fragments of the first and second polypeptide chains includes different affinity tags. In some embodiments, the removable linker further comprises one or more polypeptide dimerization motifs selected from the group consisting of homodimerization motifs, heterodimerization motifs, leucine zipper motifs, and combinations of any thereof.

In some embodiments, the Fc regions of the first and the second polypeptide chains are associated with one another via a modified interface within a constant domain of the Fc regions. In some embodiments, the constant domain is a CH2 domain or a CH3 domain. In some embodiments, the modified interface of the first polypeptide chain includes a protuberance which is positionable in a cavity in the modified interface of the second polypeptide chain. In some embodiments, the amino acid sequence of an original interface has been modified so as to introduce the protuberance and/or cavity into the modified interface such that a greater ratio of heterodimer:homodimer forms than that for a dimer having a non-modified interface. In some embodiments, the cavity includes an amino acid residue substituted into the interface of the second polypeptide, and wherein the substituted amino acid residue is selected from the group consisting of alanine (A), serine (S), threonine (T), and valine (V). In some embodiments, the protuberance includes an amino acid residue substituted into the interface of the first polypeptide, and wherein the substituted amino acid residue is selected from the group consisting of arginine (R), phenylalanine (F), tyrosine (Y), and tryptophan (W). In some embodiments, the amino acid residue is substituted into the interface of the first polypeptide at position 347, 349, 350, 351, 366, 368, 370, 392, 394, 395, 397, 398, 399, 405, 407, or 409 of the CH3 domain of human IgG1. In some embodiments, the protuberance includes a T366W amino acid substitution within the constant domain CH3 of the Fc region of the first polypeptide. In some embodiments, the cavity includes an amino acid substitution selected from the group consisting of S354C, T366S, L368A, and Y407V present within the constant domain CH3 of the Fc region of the second polypeptide.

In some embodiments, at least one the antigens is a cell-surface antigen. In some embodiments, the antigens are selected from the group consisting of CD3, CD4, CD8, CD25, CD28, CD27, T-cell receptors, CD16A, CD38, CD46, CD47, CD56, CD14, CD16b, CD71, CD79, CD68, CCR5, CCL2, SLAM, NKG2D, NKG2A, NKp46, killer-cell immunoglobulin-like receptors (KIRs), CD98, beta 2 microglobulin, CD20, CD22, CD30, CD33, CD123, CD137, CD133, BCMA, CD19, CD1a-c, prostate-specific membrane antigen (PSMA), B7-H3 (CD276), mesothelin, prostate stem cell antigen (PSCA), CEA, CLEC12A, ALPPL2, ALPP, ALPI, GD2, TAG-72, EpCAM, GPC3, GPA33, GPRC5D, Her2, SSTR2 (somatostatin receptor 2), Muc16, Muc1, FLT3, Muc18, MELAN-A, DLL3, CD307, EGFRvIII, EGFR, P-cadherin, N-cadherin, ICAM-1, VLA-4, VCAM, α4/β7 integrin, αv/β8 intergrins, αv/β3 integrins, CD44 and CD44 splicing variants, glycoprotein llb/llla, LFA-1, CD40, OX40, GITR, 41BB, c-Met, inducible T-cell costimulator (ICOS), leucine rich repeat-containing G protein-coupled receptor 5 (LGR5), VEGF, CD80, CD86, CD55, CD59, members of ErbB family, members of insulin receptor family, members of PDGF receptor family, members of VEGF receptors family, members of FGF receptor family, members of CCK receptor family, members of NGF receptor family, members of HGF receptor family, members of Eph receptor family, members of AXL receptor family, members of DDR receptor family, members of RET receptor family, members of ROS receptor family, members of LTK receptor family, members of ROR receptor family, G protein-coupled receptors (GPCRs), PD-1, PD-L1, PD-L2, CTLA-4 (CD152), B7-H3 (CD276), B7-H4 (VTCN1), LAG3, TIM-3, VISTA, SIGLEC7 (CD328), SIGLEC9 (CD329), BTLA (CD272), A2AR, IDO (indoleamine 2,3-dioxygenase), TGFβRI, TGFβRII, and TGFβR3.

In some embodiments, the scFab fragment of the first and/or second polypeptide chains includes the VL, CL, VH, and CH1 domains derived from abciximab, abciximab, adalimumab, aducanumab, alacizumab, alemtuzumab, alirocumab, alirocumab, ascrinvacumab, atezolizumab, atinumab, bapineuzumab, basiliximab, basiliximab, belimumab, bevacizumab, blinatumomab, blosozumab, bococizumab, brentuximab, canakinumab, caplacizumab, capromab, certolizumab, cetuximab, crenezumab, daclizumab, daratumumab, demcizumab, denosumab, denosumab, dinutuximab, ecukinumab, eculizumab, eculizumab, efalizumab, elotuzumab, enoticumab, etaracizumab, evinacumab, evolocumab, evolocumab, fasinumab, fulranumab, gantenerumab, golimumab, ibritumomab, icrucumab, idarucizumab, idarucizumab, inciacumab, infliximab, ipilimumab, mepolizumab, natalizumab, necitumumab, nesvacumab, nivolumab, obinutuzumab, ofatumumab, omalizumab, opicinumab, orticumab, ozanezumab, palivizumab, palivizumab, panitumumab, pembrolizumab, pertuzumab, ponezumab, ralpancizumab, ramucirumab, ramucirumab, ranibizumab, raxibacumab, refanezumab, rinucumab, rituximab, romosozumab, siltuximab, solanezumab, stamulumab, tadocizumab, tanezumab, tocilizumab, trastuzumab, ustekinumab, vedolizumab, or vesencumab. In some embodiments, the scFab fragment of the first polypeptide chain is derived from ipilimumab and the scFab fragment of the second polypeptide chain is derived from daratumumab. In some embodiments, the scFab fragment of the first polypeptide chain is derived from ipilimumab and the scFab fragment of the second polypeptide chain is derived from trastuzumab.

In some embodiments, the one or more additional scFab fragments are operably linked to the first polypeptide chain and/or the second polypeptide chain by a connector. In some embodiments, the connector is a peptide connector. In some embodiments, the additional antigens are selected from the group consisting of CD3, CD4, CD8, CD25, CD28, CD27, T-cell receptors, CD16A, CD38, CD46, CD47, CD56, CD14, CD16b, CD71, CD79, CD68, CCR5, CCL2, SLAM, NKG2D, NKG2A, NKp46, killer-cell immunoglobulin-like receptors (KIRs), CD98, beta 2 microglobulin, CD20, CD22, CD30, CD33, CD123, CD137, CD133, BCMA, CD19, CD1a-c, prostate-specific membrane antigen (PSMA), B7-H3 (CD276), mesothelin, prostate stem cell antigen (PSCA), CEA, CLEC12A, ALPPL2, ALPP, ALPI, GD2, TAG-72, EpCAM, GPC3, GPA33, GPRC5D, Her2, SSTR2 (somatostatin receptor 2), Muc16, Muc1, FLT3, Muc18, MELAN-A, DLL3, CD307, EGFRvIII, EGFR, P-cadherin, N-cadherin, ICAM-1, VLA-4, VCAM, α4/β7 integrin, αv/β8 intergrins, αv/β3 integrins, CD44 and CD44 splicing variants, glycoprotein llb/llla, LFA-1, CD40, OX40, GITR, 41BB, c-Met, inducible T-cell costimulator (ICOS), leucine rich repeat-containing G protein-coupled receptor 5 (LGR5), VEGF, CD80, CD86, CD55, CD59, members of ErbB family, members of insulin receptor family, members of PDGF receptor family, members of VEGF receptors family, members of FGF receptor family, members of CCK receptor family, members of NGF receptor family, members of HGF receptor family, members of Eph receptor family, members of AXL receptor family, members of DDR receptor family, members of RET receptor family, members of ROS receptor family, members of LTK receptor family, members of ROR receptor family, G protein-coupled receptors (GPCRs), PD-1, PD-L1, PD-L2, CTLA-4 (CD152), B7-H3 (CD276), B7-H4 (VTCN1), LAG3, TIM-3, VISTA, SIGLEC7 (CD328), SIGLEC9 (CD329), BTLA (CD272), A2AR, IDO (indoleamine 2,3-dioxygenase), TGFβRI, TGFβRII, and TGFβR3.

In some embodiments, the one or more additional scFab fragment includes the VL, CL, VH, and CH1 domains derived from abciximab, abciximab, adalimumab, aducanumab, alacizumab, alemtuzumab, alirocumab, alirocumab, ascrinvacumab, atezolizumab, atinumab, bapineuzumab, basiliximab, basiliximab, belimumab, bevacizumab, blinatumomab, blosozumab, bococizumab, brentuximab, canakinumab, caplacizumab, capromab, certolizumab, cetuximab, crenezumab, daclizumab, daratumumab, demcizumab, denosumab, denosumab, dinutuximab, ecukinumab, eculizumab, eculizumab, efalizumab, elotuzumab, enoticumab, etaracizumab, evinacumab, evolocumab, evolocumab, fasinumab, fulranumab, gantenerumab, golimumab, ibritumomab, icrucumab, idarucizumab, idarucizumab, inciacumab, infliximab, ipilimumab, mepolizumab, natalizumab, necitumumab, nesvacumab, nivolumab, obinutuzumab, ofatumumab, omalizumab, opicinumab, orticumab, ozanezumab, palivizumab, palivizumab, panitumumab, pembrolizumab, pertuzumab, ponezumab, ralpancizumab, ramucirumab, ramucirumab, ranibizumab, raxibacumab, refanezumab, rinucumab, rituximab, romosozumab, siltuximab, solanezumab, stamulumab, tadocizumab, tanezumab, tocilizumab, trastuzumab, ustekinumab, vedolizumab, or vesencumab. In some embodiments, at least one of the one or more additional scFab fragments includes the VL, CL, VH, and CH1 domains derived from atezolizumab. In some embodiments, at least one of the first and second polypeptide chains comprises an amino acid sequence having at least 80%, 90%, 95%, 96%, 97, 98%, 99% sequence identity to any one of SEQ ID NOS: 1-12.

In another aspect, provided herein are various recombinant nucleic acids including a nucleotide sequence that encodes (a) the first polypeptide chain of an engineered antibody as disclosed herein, or a scFab fragment thereof; (b) the second polypeptide chain of an engineered antibody as disclosed herein, or a scFab fragment thereof; or (c) both (a) and (b) above. In some embodiments, the nucleic acid sequence is incorporated into an expression cassette or a vector.

In another aspect, provided herein are various recombinant cells including the first polypeptide chain of an engineered antibody as disclosed herein, or a scFab fragment thereof, (b) the second polypeptide chain of an engineered antibody as disclosed herein, or a scFab fragment thereof, (c) both (a) and (b) above; (d) an engineered antibody as disclosed herein; and/or (e) a recombinant nucleic acid as disclosed herein. In some embodiments, the recombinant cell is a eukaryotic cell. In some embodiments, the eukaryotic cell is Human Embryonic Kidney 293A (HEK293A) cell, a HEK293 cell, a HEK293T cell, a HEK293F cell, a Chinese Hamster Ovary (CHO) cell, a CHO K1 cells, or a CHO-S cell.

In yet another aspect, provided herein are various methods for preparing an engineered antibody, including: (a)

providing an engineered antibody as disclosed herein; and (b) removing the removable linker to produce an antibody that does not contain the removable linker.

Non-limiting exemplary embodiments of the disclosed methods for preparing an engineered antibody include one or more of the following features. In some embodiments, the providing the engineered antibody includes co-expressing the first and the second polypeptide chains in the same recombinant cell. In some embodiments, the providing the engineered antibody includes culturing a host cell that co-expresses the first and the second polypeptide chains. In some embodiments, the methods further include a process of purifying the engineered antibody prior to and/or after the removal of the linker(s). In some embodiments, the purifying process includes one or more techniques selected from the group consisting of affinity chromatography, ion-exchange chromatography (IEC), anion exchange chromatography (AEX), cation exchange chromatography (CEX), hydroxyapatite chromatography, hydrophobic interaction chromatography (HIC), size-exclusion chromatography (SEC), metal affinity chromatography, and mixed mode chromatography (MMC). In some embodiments, the purifying process includes affinity chromatography. In some embodiments, the affinity chromatography includes protein A affinity chromatography. In some embodiments, the purifying process includes ion-exchange chromatography (IEC). In some embodiments, the produced antibody includes the engineered antibody lacking the removable linker with a purity of greater than 70%, 80%, 90%, or 95%.

In yet another aspect, provided herein are various engineered antibodies produced by a method disclosed herein. In a related aspect, provided herein are various pharmaceutical compositions, including an engineered antibody as disclosed herein, and a pharmaceutically acceptable carrier.

Each of the aspects and embodiments described herein are capable of being used together, unless excluded either explicitly or clearly from the context of the embodiment or aspect.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1A shows an exemplary scheme to produce monoclonal IgG from single-chain IgG with a thrombin cleavable linker. FIG. 1B: After thrombin cleavage, the IgG molecules produced with the thrombin-cleavable linker (Ipili-sc36TMB and Dara-sc36TMB) show molecular weights of approximately 150 kDa and can be separated into heavy chains (about 50 kDa) and light chains (about 25 kDa) with a reducing agent, β-mercaptoethanol (β-ME), a virtually identical pattern compared with the original monoclonal antibody. FIGS. 1C-1D: Ipili-sc36TMB (FIG. 1C) and Dara-sc36TMB (FIG. 1D) bind to their respective ligands in ELISA assays, showing similar binding profiles compared with the original monoclonal antibodies.

FIG. 2A shows an exemplary scheme to produce bispecific antibodies. FIG. 2B: Two bispecific antibodies, Ipili-Dara-KIH and Ipili-Her-KIH, were generated, both of which show a predominant component with a molecular weight of 150 kDa. A small fraction of contamination, likely caused by incorrectly paired homodimers, can be observed at the half size of an antibody (labeled with *). Under reducing condition, separated heavy and light chains, 50 kDa and 25 kDa respectively, were observed. FIGS. 2C-2D: Bispecific antibody Ipili-Dara-KIH binding to CTLA4-Fc (FIG. 2C) and CD38 (FIG. 2D), in comparison to the original monoclonal antibodies. FIGS. 2E-2F: Bispecific antibody Ipili-Her-KIH binding to CTLA4-Fc (FIG. 2E) and ErbB2-Fc (FIG. 2F), in comparison to the original monoclonal antibodies. FIGS. 2G-2L summarize the results of a purity assessment of the bispecific antibodies Ipili-Dara-KIH and Ipili-Her-KIH by analytical hydrophobic interaction chromatography. The main peak of Ipili_Dara_KIH (FIG. 2G) shows an elution time in-between of Ipilimumab (FIG. 211) and Daratumumab (FIG. 2I), representing the desired bispecific product that is estimated by area integration (OpenLab CDS, Agilent) to be 71% of total protein obtained from one-step protein A purification. For the Ipili-Her-KIH antibody, the main peak of Ipili_Her_KIH (FIG. 2J) shows an elution time in-between of Ipilimumab (FIG. 2K) and Herceptin (FIG. 2L), representing the desired bispecific product that is estimated to be 73% of total protein obtained from one-step protein A purification.

FIG. 3A shows an exemplary scheme to produce bispecific antibodies with built-in affinity tags, e.g., 10-His tag and Twin-Strep-Tag® that enables sequential purification of the desired heterodimer by Ni-NTA resin and Strep-Tactin® XT resin. As shown in FIG. 3B, the bispecific product of Ipili-Dara-KIH purified via the dual tags (Ni-NTA and Strep-Tactin® XT) was compared with the same product purified by protein A agarose. The contamination in the bispecific products that could be observed at the half-antibody size (the * band) was eliminated when purified with dual tags. In FIGS. 3C-3D, the purity of bispecific products was assessed by analytical hydrophobic interaction chromatography (HIC). As shown in FIG. 3E, flow cytometry analysis of Jurkat-cell binding by each of the antibodies Ipili-Dara-KIH, Daratumumab, and Ipilimumab at various concentrations (0-200 nM).

FIG. 4B pictorially summarizes the results of an SDS-PAGE analysis where the Tri-N-Fabs showed an approximate molecular weight of 200 kDa and can be separated into polypeptide chains of 50 kDa and 25 kDa under reducing conditions. Small fractions of contamination were observed, marked as (*) and (†), likely caused by homodimers. As shown in FIG. 4C, the purity of the Tri-N-Fabs is assessed by analytical hydrophobic interaction chromatography. As shown in FIGS. 4D, 4E, and 4F, Tri-N-Fabs interacts with the three intended ligands in an ELISA assay. Parental antibodies were included as references.

FIG. 5A shows an exemplary design of Tetra-N-Fabs. Additional Fab domains (III and IV) were appended to the N-terminus of a bispecific antibody described above. For the Tetra-N-Fabs produced, Fabs of Ipilimumab were placed at position I, Daratumumab at position II, Herceptin at position III, and Atezolizumab at position IV. As shown in FIG. 5B, the Tetra-N-Fabs displayed a molecular weight of 250 kDa by non-reducing SDS-PAGE analysis and could be separated into two polypeptide chains of 50 kDa and 25 kDa under reducing conditions. As shown in FIG. 5A, the purity of the Tetra-N-Fabs was estimated to be 95% by analytical HIC. FIGS. 5D, 5E, 5F, and 5G show the binding of the Tetra-N-Fabs to all four ligands with parental antibodies included as references.

FIGS. 6A and 6B are schematic presentations of two exemplary antibodies: Tri-C-Fabs (FIG. 6A; SEQ ID NOS: 4 and 11) and Tetra-C-Fabs (FIG. 6B; SEQ ID NOS: 11 and 12). In these antibodies, scFab domains representing the $3^{rd}$ and $4^{th}$ specificity were appended to the C-terminus of the bispecific antibody. Fabs of Ipilimumab were placed at position I, Daratumumab at position II, Herceptin at position III, and Atezolizumab at position IV (in the case of Tetra-C-Fabs). FIG. 6C pictorially summarizes the results of an SDS-PAGE analysis of Tri-C-Fabs and Tetra-C-Fabs, where the Tri-C-Fabs displayed an approximate molecular weight of 200 kDa and can be separated into polypeptide chains of 75 kDa, 50 kDa, and 25 kDa under reducing conditions. The Tetra-C-Fabs shows an approximate molecular weight of 250 kDa and can be separated into polypeptide chains of 75 kDa and 25 kDa under reducing conditions. FIGS. 6D, 6E, and 6F show that the Tri-C-Fabs binds to all three intended ligands by ELISA, with the parental antibodies included as references. FIGS. 6G, 6H, 6I, and 6J graphically summarize the binding of the Tetra-C-Fabs to all four intended ligands by ELISA, with parental antibodies included as references. FIGS. 6K-6L summarize the results of a purity assessment of tri-specific and tetra-specific antibodies by analytical hydrophobic interaction chromatography. Purities of Tri-C-Fabs (FIG. 6K) and Tetra-CFabs (FIG. 6L) are estimated to be 93% and 79%, respectively.

FIG. 7 depicts the amino acid sequence of the sc36TMB linker (SEQ ID NO: 80). The thrombin cleavage site are indicated with arrows.

DETAILED DESCRIPTION OF THE DISCLOSURE

Figure 1A:
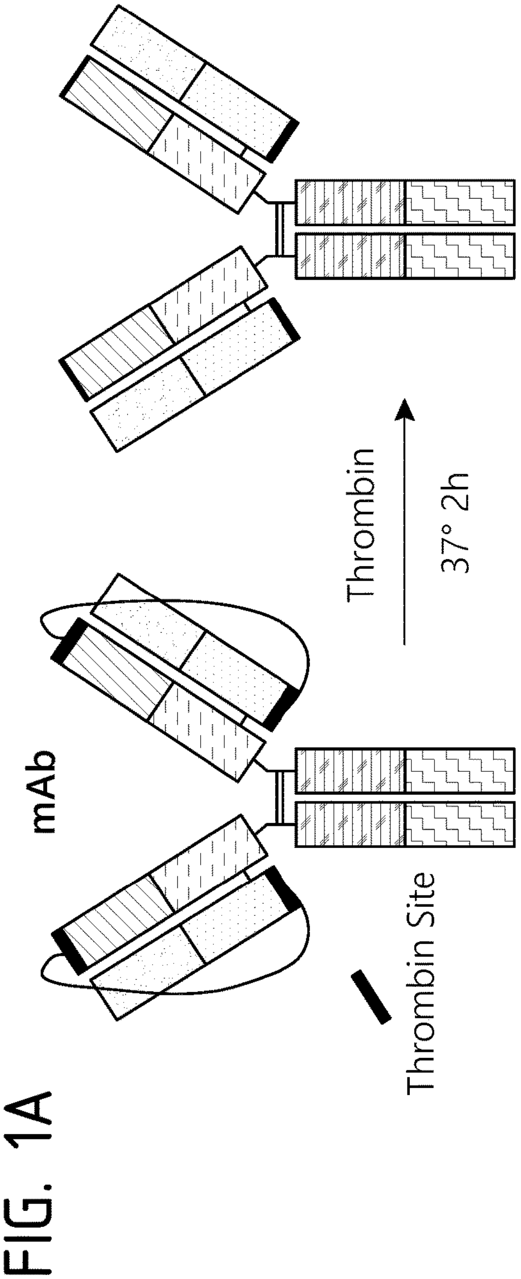
FIGS. 1A-1D graphically summarize the results of experiments performed to illustrate that monoclonal antibodies processed from single-chain IgGs show similar biophysical and binding properties as the original antibodies.
Figure 1B:
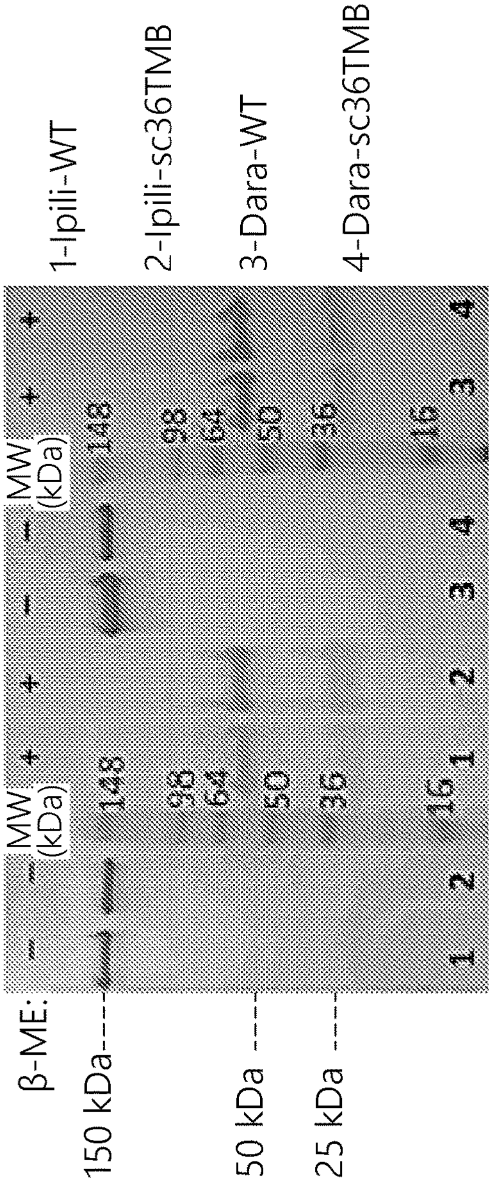

The present disclosure relates generally to the field of antibody engineering and particular concerns multispecific antibodies that specifically bind to two or more different target antigens or epitopes. In particular, provided herein, inter alia, are compositions and methods concerning the production of engineered antibodies having (i) multiple antigen-binding specificities and (ii) Fc regions that have been modified to promote heterodimer formation between heavy chains from two different specificities. More particularly, provided herein are engineered antibodies having (i) two singe-chain antigen binding (scFab) fragments specific for two different epitopes and (ii) Fc regions associated with one another via an interface which has been modified to promote heterodimer formation.

A fundamental problem in multispecific antibody generation is how to properly pair heavy and light chains from antibodies with different specificities. For example, in bispecific antibody construction, although the "knobs-into-holes" (KIH) approach has been used to promote heterodimer formation between heavy chains from two different specificities, the efficiency is less than desired, and homodimer formations are frequently observed. In addition, the light chain pairing problem cannot be solved by the original KIH design. As a variation of the original strategy, KIH technique has been used also for light chain pairing but again the proper pairing efficiency remains an issue. As such, the overall efficiency of bispecific antibody generation is less than desired even with the dual knob-into-hole strategy.

For multispecific antibody generation, there are only a small number of studies that have ventured into this area, due to complexity associated with higher order of specificity. Most of the prior approaches are based on simple joining of multiple scFvs in tandem or appendixing antibody fragments (often scFvs) to the IgG framework. However, the resulting multispecific molecules often have production and stability problems, limiting their use in therapeutic development. As described in greater detail below, various compositions and methods disclosed herein enable facile generation of multispecific antibody and furthermore the resulting multispecific antibodies can use Fab as the basic binding module with robust binding affinity and specificity.

In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

DEFINITIONS

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, comprising mixtures thereof "A and/or B" is used herein to include all of the following alternatives: "A", "B", "A or B", and "A and B".

Certain values and ranges are presented herein with numerical values being preceded by the term "about." The term "about" is used herein to provide literal support for the exact number that it precedes, as well as a number that is near to or approximately the number that the term precedes. Generally, the term "about" has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms, "cell", "cell culture", "cell line", "recombinant cell", "recipient cell" and "host cell" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transfected cell.

As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, e.g., operably linked.

The term "operably linked", as used herein, denotes a physical or functional linkage between two or more elements, e.g., polypeptide sequences or polynucleotide sequences, which permits them to operate in their intended fashion. For example, an operable linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous. In addition, in the context of a polypeptide, "operably linked" refers to a physical linkage (e.g., directly or indirectly linked) between amino acid sequences (e.g., different segments, modules, or domains) to provide for a described activity of the polypeptide. In the present disclosure, various segments, modules, or domains of the engineered multispecific antibodies of the disclosure may be operably linked to retain proper folding, processing, targeting, expression, binding, and other functional properties of the engineered multispecific antibodies in the cell. Unless stated otherwise, various modules, domains, and segments of the engineered multispecific antibodies of the disclosure are operably linked to each other. Operably linked modules, domains, and segments of the engineered multispecific antibodies of the disclosure may be contiguous or non-contiguous (e.g., linked to one another through a linker).

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated using published techniques and widely available computer programs, such as the GCS program package (Devereux et al, *Nucleic Acids Res.* 12:387, 1984), BLASTP, BLASTN, FASTA (Atschul et al., *J Mol Biol* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "recombinant" or "engineered" nucleic acid or polypeptide as used herein, refers to a nucleic acid molecule or polypeptide that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. Other non-limiting examples of recombinant nucleic acids and recombinant polypeptides include engineered multispecific antibodies disclosed herein and the nucleic acids encoding such antibodies.

The term "vector" is used herein to refer to a nucleic acid molecule or sequence capable of transferring or transporting another nucleic acid molecule. The transferred nucleic acid molecule is generally linked to, e.g., inserted into, the vector nucleic acid molecule. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments in vitro and/or in vivo. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In some embodiments, a vector is a gene delivery vector. In some embodiments, a vector is used as a gene delivery vehicle to transfer a gene into a cell.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is understood that aspects and embodiments of the disclosure described herein include "comprising," "consisting," and "consisting essentially of" aspects and embodiments. As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or step.

Headings, e.g., (a), (b), (i) etc., are presented merely for ease of reading the specification and claims. The use of headings in the specification or claims does not require the steps or elements be performed in alphabetical or numerical order or the order in which they are presented.

Multispecific Antibodies

As discussed above, antibodies with multispecificity hold great promise for the next generation of therapeutic drugs against a variety of diseases, including cancers, infections, and immunological disorders. Compared to traditional monospecific antibodies that specifically recognize one ligand, multispecific antibodies can recognize two or more ligands and thus may provide an advantage in co-engaging different cell types, creating synthetic specificity, altering internalization dynamics, synergistically neutralizing virus and toxin, and simultaneously block multiple signaling pathways to maximize therapeutic benefits. In addition, multispecific antibodies can increase sensitivity and breath for recognizing target cells, tissues, or pathogens. Some bispecific antibodies were also designed to possess desirable properties other than recognition, such as enhanced production, extended half-time, or increased tissue penetration.

Production of multispecific antibodies is more complicated than monoclonal antibodies. Many different formats of bi-specific antibodies have been designed, including chemical conjugation of two different antibodies, tandem single-chain variable fragments (scFv) or Fab domains, and scFv or Fab fusion to immunoglobulins or other scaffold proteins. The design of multispecific antibodies is often derived from these bispecific formats but with substantially higher complexity. Each of these designs, and their derivatives, features distinct topology and thus may have non-identical biological functions and different pharmacokinetics, which needs to be tested experimentally. Depending on the molecular form of the building block, some formats suffer from drawbacks, ranging from poor production, low in vivo stability, and immunogenicity. Consequently, new methods and formats to produce bi- or multispecific antibodies are important topics for exploration.

Among the various designs, the IgG-like format has been an area of interest due to its resemblance to natural antibody, which often have good yields, stability, and relatively low immunogenicity. To produce these IgG-like molecules, two major problems have to be addressed: proper pairing of heavy chains from different antibodies, and correct pairing of the light chains to their corresponding heavy chains. The first issue is often addressed by the now classic knobs-into-holes (KIH) Fc mutants that enforce the formation of heavy chain heterodimers. However, the desired heterodimer in such a design is not exclusive, with homodimers still present, likely due to insufficient thermal stability of the CH3 domain and the Fc interface of the KIH heterodimer. In fact, both "knob" and "hole" Fc domains can form homodimers, causing substantial contamination in products that were generated by the KIH approach alone. As the homodimer often shares similar biophysical features as the heterodimer, such as size and isoelectric point, optimization and purification of the KIH bispecific format can be challenging and time-consuming. Additional modifications of the KIH Fc have been previously explored to enhance the formation of heterodimer.

To avoid promiscuous association of light chains to heavy chains in bispecific antibody production, different antibodies (with different ligand binding specificity) using one common light chain were previously selected from phage or yeast display libraries, providing a popular solution to the light chain pairing problem. However, this restriction on light chain reduces the sequence space that can be explored for binding affinity, specificity and downstream developability. In another example, the CrossMab format is an alternative approach for solving the light chain pairing problem, swapping only one pair of the variable or constant domains in one of the Fab fragments, and thus inhibiting chain mismatching between the switched Fab and the un-switched ones. Nonetheless, incorrect pairing of light chains are often observed, resulting in variable levels of product heterogeneity. The issue of immunogenicity of the hybrid variable-constant domain therefore remains to be investigated.

The feasibility of single-chain IgG (scIgG) has been demonstrated by previous studies and can be used to resolve the light chain pairing problem. However, an extended linker between light and heavy chains, varying between 30-60 residues in length, was retained in the final product, limiting its utility. As described herein, a new approach has been developed to produce single-chain IgG with cleavable linkers, allowing for removal of the undesired linkers in vitro, for example through the use of an enzymatic reaction (e.g., proteolytic reaction). As described in greater detail below, a thrombin cleavable linker has been successfully introduced between the light chain and the heavy chain, which can be removed by commercially available enzymes with high efficiency and accuracy. Antibodies produced using this approach show similar yield as the original antibodies, feature intact ligand-binding affinity, and contain only a few linker residues. Compared to an in vivo cleavage system designed in a previous study the cleavage in the disclosed system happens post-translationally and post-purification, ensuring correct pairing of the chains during cleavage. Furthermore, the linkers enable to engineer extra features in each of the two chains, such as different affinity tags, which can be used to facilitate purification of highly pure bispecific IgG molecules. Finally, the disclosed approach is entirely modular and allows facile production of multispecific antibodies, with IgG-like backbone and Fab-based binding modules.

In some embodiments, the compositions and methods disclosed herein employ single-chain IgG containing singe-chain antigen binding (scFab) fragments as a transient intermediate for proper heavy and light chain pairing and further use protease to cleave off removable linkers incorporated in the scFab fragments to generate the bispecific antibodies in an IgG-like configuration. Furthermore, the disclosed technology enables multispecific antibody generation, which has rarely been done or even attempted by other technologies due to the higher order of complexity associated with multispecific antibody generation. Indeed, by employing the compositions and methods described herein, experiments have been performed to readily use the technology disclosed herein to produce tri- and tetra-specific antibodies. Since the disclosed approach for multispecific antibody production is modular (similar to LEGO toy assembly), even higher order of specificities can be generated. Without being bound any particular theory, it is believed that the higher order of specificity enables simultaneous or synergistic recognition of multiple targets, thus maximizing therapeutic effect or creating new therapeutic opportunities.

Compositions of the Disclosure

As described in greater detail below, one aspect of the present disclosure relates to a new class of multispecific antibodies that specifically bind to two or more different target antigens or epitopes. In particular, provided herein, inter alia, are compositions and methods concerning the production of engineered antibodies having (i) multiple antigen-binding specificities and (ii) Fc regions that have been modified to promote heterodimer formation between heavy chains from two different specificities. In some embodiments, provided herein are engineered antibodies having (i) two singe-chain antigen binding (scFab) fragments specific for two different epitopes and (ii) Fc regions associated with one another via an interface which has been modified to promote heterodimer formation. Also provided, in other related aspects of the disclosure, are nucleic acids encoding the multispecific antibodies as disclosed herein, recombinant cells expressing the multispecific antibodies as disclosed herein, pharmaceutical compositions containing the nucleic acids and/or recombinant cells as disclosed herein.

Engineered Antibodies

In one aspect, some embodiments disclosed herein relate to a novel engineered antibodies containing multiple antigen-binding specificities and (ii) Fc regions that have been modified to promote heterodimer formation between heavy chains from two different specificities. In some embodiments, the disclosed engineered antibody includes a first and a second polypeptide chain, each of the first and second polypeptide chains including (a) one or more antigen-binding moieties and (b) an antibody Fc region, wherein the Fc regions of the first and a second polypeptide chains are associated with one another via an interface which has been modified to promote heterodimer formation. In some embodiments, the N-terminus of the first polypeptide chain and/or the second polypeptide chain is operably linked to one or more additional scFab fragments having specificity for additional antigens. In some embodiments, the engineered antibodies of the disclosure, the N-terminus of the first polypeptide chain is operably linked to at least one, e.g., 1, 2, 3, 4, 5, or 6 additional scFab fragments having specificity for additional antigens. In some embodiments, the N-terminus of the second polypeptide chain is operably linked to at least one, e.g., 1, 2, 3, 4, 5, or 6 additional scFab fragments having specificity for additional antigens.

In some embodiments, the C-terminus of the first polypeptide chain and/or the second polypeptide chain is operably linked to one or more additional scFab fragments having specificity for additional antigens. In some embodiments, the engineered antibodies of the disclosure, the C-terminus of the first polypeptide chain is operably linked to at least one, e.g., 1, 2, 3, 4, 5, or 6 additional scFab fragments having specificity for additional antigens. In some embodiments, the C-terminus of the second polypeptide chain is operably linked to at least one, e.g., 1, 2, 3, 4, 5, or 6 additional scFab fragments having specificity for additional antigens.

The scFab fragments of the engineered antibodies disclosed herein can include naturally-occurring amino acid sequences or can be engineered, designed, or modified so as to provide desired and/or improved properties, e.g., binding affinity. Generally, binding affinity can be used as a measure of the strength of a non-covalent interaction between two molecules, e.g., an antibody or portion thereof and an antigen (e.g., CD38, PD-L1, or HER2 antigen). In some cases, binding affinity can be used to describe monovalent interactions (intrinsic activity). Binding affinity between two molecules may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods, and can be computed even for complex mixtures by methods such as those set forth in Caceci et al. (1984, *Byte* 9: 340-362). For example, the $K_D$ may be established using a double-filter nitrocellulose filter binding assay such as that disclosed by Wong & Lohman (1993, *Proc. Natl. Acad. Sci. USA* 90: 5428-5432). Other standard assays to evaluate the binding ability of engineered antibodies of the present disclosure towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA. In some embodiments, the binding affinity of an antibody or an antigen-binding moiety for a target antigen (e.g., CD38, PD-L1, or HER2 antigen) can be calculated by the Scatchard method described by Frankel et al., *Mol. Immunol,* 16: 101-106, 1979. It will be understood that an antigen-binding moiety that "specifically binds" an antigen (such as HER2) is an antigen-binding moiety that does not significantly bind other antigens but binds the target antigen with high affinity, e.g., with an equilibrium constant ($K_D$) of 100 nM or less, such as 60 nM or less, for example, 30 nM or less, such as, 15 nM or less, or 10 nM or less, or 5 nM or less, or 1 nM or less, or 500 pM or less, or 400 pM or less, or 300 pM or less, or 200 pM or less, or 100 pM or less.

In some embodiments, the antigen-binding moiety is selected from the group consisting of an antigen-binding fragment (Fab), a single-chain variable fragment (scFv), a nanobody, a heavy chain variable (VH) domain, a light chain variable (VL) domain, a single domain antibody (dAb), a VNAR domain, and a VHH domain, a diabody, or a functional fragment of any thereof. In some embodiments, the antigen-binding moiety includes a VH domain and a VL domain. In some embodiments, the antigen-binding moiety includes a single-chain antigen-binding (scFab) fragment.

In some embodiments, the disclosed engineered antibody includes a first and a second polypeptide chain, each of the first and second polypeptide chains including: (a) a single-chain antigen-binding (scFab) fragment which includes, in N-terminal to C-terminal direction, (i) a VL domain; (ii) a light chain constant domain (CL); (iii) a removable linker; (iv) a VH domain; and (v) a heavy chain constant domain (CH1), wherein the scFab fragments of the first and second polypeptide chains have specificity for different antigens; and (b) an antibody Fc region N-terminally linked to the scFab fragment in (a), wherein the Fc regions of the first and a second polypeptide chains are associated with one another via an interface which has been modified to promote heterodimer formation.

In some embodiments, the engineered antibody disclosed herein is multivalent, for example, bi-, tri-, or tetravalent (i.e., the engineered antibody includes two, three, or four antigen-binding moieties). In some embodiments, the engineered antibody of the disclosure can be a multivalent antibody (e.g., bivalent antibody, trivalent antibody, or tetravalent) including at least two antigen-binding moieties each having specific binding activity for a target protein. In some embodiments, the at least two antigen-binding moieties having specific binding for at least two different target proteins. Such antibody is multivalent, multispecific antibody (e.g., bispecific, tri-specific, tetra-specific, etc.) Accordingly, in some embodiments, the disclosed engineered antibody can be can be a bivalent, bispecific antibody. In some embodiments, the disclosed engineered antibody can be a trivalent, tri-specific antibody. In some embodiments, the disclosed engineered antibody can be a tetravalent, tetra-specific antibody.

In some embodiments, the at least two antigen-binding moieties have specific binding activity for the same target protein. Such antibody is multivalent, monospecific antibody. Accordingly, in some embodiments, the disclosed engineered antibody can be a bivalent, monospecific antibody. In some embodiments, the disclosed engineered antibody can be a trivalent, monospecific antibody. In some embodiments, the disclosed engineered antibody can be a tetravalent, monospecific antibody. In some embodiments, the engineered antibody disclosed herein is monospecific, e.g. all the scFab fragments bind the same antigen. In some embodiments, all the antigen-binding moieties bind the same epitope(s) of said antigen. In some embodiments, at least two antigen-binding moieties bind different epitopes on the target antigen.

Target Antigens

In principle, there are no particular limitations with regard to suitable target antigens. In particular, the scFab fragments used in this disclosure can be derived from antibodies of any species (e.g. mouse, rat, rabbit, goat, human, etc.) or engineered (e.g., humanized) and having specificity to any given antigen/epitope. For simplicity, only variable domain sequences from four different antibodies are discussed in the Examples below. However, due to the modular design of the disclosed antibody constructs, the skilled artisan will appreciate that regions, domains, and segments of any known antibody may be substituted into the disclosed antibody structures.

Antigens suitable for the compositions and methods disclosed herein include, but are not limited to cell-surface antigens and extracellular antigens (e.g., those are not associated with cell surface). Non-limiting examples of suitable cell-surface target antigens include CD3, CD4, CD8, CD25, CD28, CD27, T-cell receptors, CD16A, CD38, CD47, CD56, CD14, CD16b, CDw17, CD18, CD71, CD79, CD68, CCR5, CCL2, SLAM, NKG2D, NKG2A, NKp46, Killer-cell immunoglobulin-like receptors (KIRs), CD94, CD95, CD98, CD99, CD99R, beta 2 microglobulin, CD20, CD22, CD30, CD33, CD123, CD137, CD133, BCMA, CD19, CD1a-c, CD2, CD2R, CD9, CD10, CD11a, CD11 b, CD11 c, CDw12, CD13, CD14, CD15, CD15s, CD45, CD45A, CD45B, CD99, CD99R, CD100, CDw101, CD102-CD106, CD107a-b, CDw108, CDw109, CD115, CDw116, CD117, CD119, CD120a-b, CD121a-b, CD122, CDw124, CD126, CD127, CD128, CD129, and CD130; prostate-specific membrane antigen (PSMA), B7-H3 (CD276), mesothelin, Prostate stem cell antigen (PSCA), CEA, CLEC12A, ALPPL2, ALPP, ALPI, GD2, TAG-72, EpCAM, GPC3, GPA33, GPRC5D, Her2, SSTR2 (Somatostatin Receptor 2), Muc16, Muc1, FLT3, CD46, CD48, CD5, CD6, Muc18, MELAN-A, DLL3, CD307, EGFRvIII, EGFR, P-cadherin, N-cadherin, ICAM-1, VLA-4, VCAM, α4/β7 integrin, αv/β8 and αv/β3 integrin including either α or β subunits, CD44 and CD44 splicing variants, glycoprotein llb/llla, LFA-1, CD40, 41BB, c-Met, Inducible T-cell COStimulator (ICOS), Leucine Rich Repeat Containing G Protein-Coupled Receptor 5 (LGR5), VEGF, CD80, CD86, CD55, and CD59.

Additional antigens that can be suitably used for the chimeric polypeptides disclosed herein include, but are not limited to members of receptor tyrosine kinase (RTK) family, which includes 20 classes, e.g., RTK class I (EGF receptor family) (ErbB family, e.g., EGFR, HER2, HER3 and HER4); RTK class II (Insulin receptor family, e.g., INSR, IGFR); RTK class III (PDGF receptor family, e.g., PDGFRα, PDGFRβ, M-CSFR, KIT, FLT3L); RTK class IV (VEGF receptors family, e.g., VEGFR1, VEGFR2, VEGFR3); RTK class V (FGF receptor family, e.g., FGFR1, FGFR2, FGFR3, FGFR4); RTK class VI (CCK receptor family, e.g., CCK4); RTK class VII (NGF receptor family, e.g., TRKA, TRKB, TRKC); RTK class VIII (HGF receptor family, e.g., c-MET, RON); RTK class IX (Eph receptor family, e.g., EPHA1, EPHA2, EPHA3, EPHA4, EPHA5, EPHA6, and EPHB1 to 6); RTK class X (AXL receptor family, e.g., AXL, MER, TYRO3); RTK class XI (TIE receptor family, e.g., TIE, TEK); RTK class XII (RYK receptor family, e.g., RYK); RTK class XIII (DDR receptor family, e.g., DDR1, DDR2); RTK class XIV (RET receptor family, e.g., RET); RTK class XV (ROS receptor family, e.g., ROS1); RTK class XVI (LTK receptor family, e.g., LTK, ALK); RTK class XVII (ROR receptor family, e.g., ROR1, ROR2); RTK class XVIII (MuSK receptor family, e.g., MuSK); RTK class XIX (LMR receptor, e.g., AATYK1, AATYK2, AATYK3); RTK class XX (e.g., RTK106).

Also suitable antigens for the chimeric polypeptides disclosed herein include protein-coupled receptors (GPCRs), which include 6 classes, Class A (or 1) Rhodopsin-like; Class B (or 2) Secretin receptor family; Class C (or 3) Metabotropic glutamate/pheromone; Class D (or 4) Fungal mating pheromone receptors; Class E (or 5) Cyclic AMP receptors; and Class F (or 6) Frizzled/Smoothened. Further suitable antigens for the chimeric polypeptides and methods disclosed herein include stimulatory checkpoint molecules and inhibitory checkpoint molecules. Stimulatory checkpoint molecules include members of the tumor necrosis factor (TNF) receptor superfamily—CD27, CD40, OX40, GITR and CD137; members of the B7-CD28 superfamily CD28 itself and ICOS; and the Interleukin-2 receptor beta sub-unit CD122. Inhibitory checkpoint molecules include PD-1 (Programmed Death 1 receptor) and its ligands PD-L1 and PD-L2; CTLA-4 (Cytotoxic T-Lymphocyte-Associated protein 4, aka CD152); B7-H3 (CD276); B7-H4 (VTCN1); LAG3 (Lymphocyte Activation Gene-3); TIM-3 (T-cell Immunoglobulin domain and Mucin domain 3); VISTA (V-domain Ig suppressor of T cell activation); SIGLEC7 (Sialic acid-binding immunoglobulin-type lectin 7, aka CD328) and SIGLEC9 (Sialic acid-binding immunoglobulin-type lectin 9, aka CD329); BTLA (B and T Lymphocyte Attenuator, aka CD272); A2AR (Adenosine A2A receptor); and IDO (Indoleamine 2,3-dioxygenase).

Additional antigens that can be suitably used for the chimeric polypeptides disclosed herein include, but are not limited to receptors for hormones or growth factors, transforming growth factor beta (TGFβ) receptors, which include type I receptors ALK1 (ACVRL1), ALK2 (ACVR1A), ALK3 (BMPR1A), ALK4 (ACVR1B), ALK5 (TGFβR1), ALK6 (BMPR1B), and ALK7 (ACVR1C); and type II receptors TGFβR2, BMPR2, ACVR2A, ACVR2B, and AMHR2 (AMHR); and type III receptor TGFβR3, tumor-associated post-translational modifications, including polysialic acid (polySia), Gb3/CD77, GM3, GD2, GD3, the Thomsen-Friedenreich antigen (Gal-GalNAc), cancer O-glycans (Tn, sTn (sialyl Tn antigen), and T antigen), SLex and SLea (sialyl-Lewis a), altered branching and fucosylation of N-glycans, increased mucins and truncated O-glycans, altered expression of hyaluronan, changes in sulfated glycosaminoglycans, stage-specific embryonic antigen-3 (SSEA-3), SSEA-3 with fucose (Globo H), and SSEA-4.

Suitable antigens for the chimeric polypeptides disclosed herein additionally include secreted molecules such as an interferon such as interferon-alpha, -beta, and -gamma; colony stimulating factors (CSFs), e.g., M-CSF, GM-CSF, and G-CSF; interleukins (ILs), e.g., IL-1 to IL-10; transforming growth factor (TGF) such as TGF-alpha and TGF-beta, including TGF-β1, TGF-β2, TGF-β3, TGF-β4, or TGF-β5; vascular endothelial growth factor (VEGF); RANTES (regulated on activation normally T-cell expressed and secreted); human macrophage inflammatory protein (MIP-1-alpha); platelet-derived growth factor (PDGF); fibroblast growth factor such as aFGF and bFGF; epidermal growth factor (EGF); insulin-like growth factor-I and -II (IGF-I and IGF-II); des(1-3)-IGF-1 (brain IGF-I), insulin-like growth factor binding proteins; biologic toxins and immunotoxins; a growth hormone, including human growth hormone and bovine growth hormone; growth hormone releasing factor; a neurotrophic factor such as bone-derived neurotrophic factor (BDNF), neurotrophin-3, -4, -5, or -6 (NT-3, NT-4, NT-5, or NT-6), or a nerve growth factor such as NGF-β; parathyroid hormone; thyroid stimulating hormone; rheumatoid factors; erythropoietin; osteoinductive factors; a bone morphogenetic protein (BMP); clotting factors such as factor VIIIC, factor IX, tissue factor (TF), and von Willebrands factor; anti-clotting factors such as Protein C; bombesin; thrombin; hemopoietic growth factor; tumor necrosis factor-alpha and -beta; follicle stimulating hormone; calcitonin; luteinizing hormone; glucagon; atrial natriuretic factor; a plasminogen activator, such as urokinase or human urine or tissue-type plasminogen activator (t-PA); enkephalinase; Muellerian-inhibiting substance; relaxin A-chain; relaxin B-chain; prorelaxin; DNase; inhibin; activin; superoxide dismutase; a serum albumin such as human serum albumin; a portion of the virus envelope; and addressins, lipoproteins; alpha-1-antitrypsin; insulin A-chain; insulin B-chain; proinsulin; lung surfactant; obesity (OB) receptor; mouse gonadotropin-associated peptide; a microbial protein, such as beta-lactamase; protein A or D; and IgE.

In some embodiments, the antigens are selected from the group consisting of CD3, CD4, CD8, CD25, CD28, CD27, T-cell receptors, CD16A, CD38, CD46, CD47, CD56, CD14, CD16b, CD71, CD79, CD68, CCR5, CCL2, SLAM, NKG2D, NKG2A, NKp46, killer-cell immunoglobulin-like receptors (KIRs), CD98, beta 2 microglobulin, CD20, CD22, CD30, CD33, CD123, CD137, CD133, BCMA, CD19, CD1a-c, prostate-specific membrane antigen (PSMA), B7-H3 (CD276), mesothelin, prostate stem cell antigen (PSCA), CEA, CLEC12A, ALPPL2, ALPP, ALPI, GD2, TAG-72, EpCAM, GPC3, GPA33, GPRC5D, Her2, SSTR2 (somatostatin receptor 2), Muc16, Muc1, FLT3, Muc18, MELAN-A, DLL3, CD307, EGFRvIII, EGFR, P-cadherin, N-cadherin, ICAM-1, VLA-4, VCAM, α4/β7 integrin, αv/β8 intergrins, αv/β3 integrins, CD44 and CD44 splicing variants, glycoprotein llb/llla, LFA-1, CD40, OX40, GITR, 41BB, c-Met, inducible T-cell costimulator (ICOS), leucine rich repeat-containing G protein-coupled receptor 5 (LGR5), VEGF, CD80, CD86, CD55, CD59, members of ErbB family, members of insulin receptor family, members of PDGF receptor family, members of VEGF receptors family, members of FGF receptor family, members of CCK receptor family, members of NGF receptor family, members of HGF receptor family, members of Eph receptor family, members of AXL receptor family, members of DDR receptor family, members of RET receptor family, members of ROS receptor family, members of LTK receptor family, members of ROR receptor family, G protein-coupled receptors (GPCRs), PD-1, PD-L1, PD-L2, CTLA-4 (CD152), B7-H3 (CD276), B7-H4 (VTCN1), LAG3, TIM-3, VISTA, SIGLEC7 (CD328), SIGLEC9 (CD329), BTLA (CD272), A2AR, IDO (indoleamine 2,3-dioxygenase), TGFβRI, TGFβRII, and TGFβR3.

As discussed above, the approach disclosed herein is highly versatile and applicable to any monoclonal antibody pair or panel, which in turns can expedite evaluation and therapeutic development of multispecific antibodies.

Generally, the scFab fragment of the first and/or second polypeptide chains includes the VL, CL, VH, and CH1 domains derived from any monoclonal antibody known in the art. Non-limiting antibodies suitable for the compositions and methods disclosed herein include abciximab, abciximab, adalimumab, aducanumab, alacizumab, alemtuzumab, alirocumab, alirocumab, ascrinvacumab, atezolizumab, atinumab, bapineuzumab, basiliximab, basiliximab, belimumab, bevacizumab, blinatumomab, blosozumab, bococizumab, brentuximab, canakinumab, caplacizumab, capromab, certolizumab, cetuximab, crenezumab, daclizumab, daratumumab, demcizumab, denosumab, denosumab, dinutuximab. Additional suitable antibodies suitable for the compositions and methods disclosed herein include, but are not limited to, ecukinumab, eculizumab, eculizumab, efalizumab, elotuzumab, enoticumab, etaracizumab, evinacumab, evolocumab, evolocumab, fasinumab, fulranumab, gantenerumab, golimumab, ibritumomab, icrucumab, idarucizumab, idarucizumab, inciacumab, infliximab, ipilimumab, mepolizumab, natalizumab, necitumumab, nesvacumab, nivolumab, obinutuzumab, ofatumumab, omalizumab, opicinumab, orticumab, ozanezumab.

Further antibodies suitable for the compositions and methods disclosed herein include, but are not limited to, palivizumab, palivizumab, panitumumab, pembrolizumab, pertuzumab, ponezumab, ralpancizumab, ramucirumab, ramucirumab, ranibizumab, raxibacumab, refanezumab, rinucumab, rituximab, romosozumab, siltuximab, solanezumab, stamulumab, tadocizumab, tanezumab, tocilizumab, trastuzumab, ustekinumab, vedolizumab, and vesencumab. In some embodiments, the scFab fragment of the first polypeptide chain includes the VL, CL, VH, and CH1 domains derived from ipilimumab and the scFab fragment of the second polypeptide chain includes the VL, CL, VH, and CH1 domains derived from daratumumab. In some embodiments, the scFab fragment of the first polypeptide chain includes the VL, CL, VH, and CH1 domains derived from ipilimumab and the scFab fragment of the second polypeptide chain includes the VL, CL, VH, and CH1 domains derived from trastuzumab.

In some embodiments, the one or more additional scFab fragments are operably linked to the first polypeptide chain and/or the second polypeptide chain, as illustrated in Example 6. In some embodiments, only one of the first and second polypeptide chains is N-terminally linked one or more additional scFab fragments (see, e.g., Example 6 and FIGS. 4A-4F). In some embodiments, the one or more additional scFab fragments are N-terminally linked only to the first polypeptide chain. In some embodiments, the one or more additional scFab fragments are N-terminally linked only to the second polypeptide chain. In some embodiments, both the first polypeptide chain and the second polypeptide chain are N-terminally linked to one or more additional scFab fragments (see, e.g., Example 6 and FIGS. 5A-5G). In some embodiments, only one of the first and second polypeptide chains is N-terminally linked one or more additional scFab fragments (see, e.g., Example 6, and SEQ ID NOS: 4 and 11, and FIG. 6A). In some embodiments, the one or more additional scFab fragments are C-terminally linked only to the first polypeptide chain. In some embodiments, the one or more additional scFab fragments are C-terminally linked only to the second polypeptide chain. In some embodiments, both the first polypeptide chain and the second polypeptide chain are C-terminally linked to one or more additional scFab fragments (see, e.g., Example 6, SEQ ID NOS: 11-12, and FIG. 6B).

Generally, the additional scFab fragments can include the VL, CL, VH, and CH1 domains derived from any monoclonal antibody known in the art. Non-limiting monoclonal antibodies suitable for the compositions and methods disclosed herein include abciximab, abciximab, adalimumab, aducanumab, alacizumab, alemtuzumab, alirocumab, alirocumab, ascrinvacumab, atezolizumab, atinumab, bapineuzumab, basiliximab, basiliximab, belimumab, bevacizumab, blinatumomab, blosozumab, bococizumab, brentuximab, canakinumab, caplacizumab, capromab, certolizumab, cetuximab, crenezumab, daclizumab, daratumumab, demcizumab, denosumab, denosumab, dinutuximab, ecukinumab, eculizumab, eculizumab, efalizumab, elotuzumab, enoticumab, etaracizumab, evinacumab, evolocumab, evolocumab, fasinumab, fulranumab, gantenerumab, golimumab, ibritumomab, icrucumab, idarucizumab, idarucizumab, inciacumab, infliximab, ipilimumab, mepolizumab, natalizumab, necitumumab, nesvacumab, nivolumab, obinutuzumab, ofatumumab, omalizumab, opicinumab, orticumab, ozanezumab, palivizumab, palivizumab, panitumumab, pembrolizumab, pertuzumab, ponezumab, ralpancizumab, ramucirumab, ramucirumab, ranibizumab, raxibacumab, refanezumab, rinucumab, rituximab, romosozumab, siltuximab, solanezumab, stamulumab, tadocizumab, tanezumab, tocilizumab, trastuzumab, ustekinumab, vedolizumab, and vesencumab. In some embodiments, at least one of the additional scFab fragments includes the VL, CL, VH, and CH1 domains derived from atezolizumab.

It will be appreciated that one or more amino acid substitutions, additions and/or deletions may be made to the antibody variable domains, provided by the present disclosure, without significantly altering the ability of the antibody to bind to target antigen and to neutralize activity thereof. The effect of any amino acid substitutions, additions and/or deletions can be readily tested by one skilled in the art, for example by using known in vitro assays, for example a BIAcore assay.

The use of a single chain variable fragment (scFv) to confer specificity to a specific antigen allows for a modular construction of multispecific antibodies. The use of scFv fragment(s) fused to the terminus of IgG heavy chains and/or light chains for construction of multispecific antibodies has been previously described. This format ("IgG-scFv") allows a conventional IgG to be converted into a bispecific antibody wherein a first specificity is encoded in the variable domains of the IgG and a second specificity is encoded in the scFv domains attached through a flexible linker region. Variations of this format include fusing scFv domains at the N- or C-termini of the heavy or light chains; the scFvs may have the same or differing antigen-binding specificities (Spangler, J. B. et al., J. Mol. Biol. 422, 532-544, 2012). In addition, through the use of heavy-chain heterodimers (for example, using knob-hole or similar constructs), scFvs of differing specificities may be attached to the N- or C-terminus of each heavy chain.

Any modifications that could be made to an IgG could also be made to the disclosed structures, including: the addition or deletion of constant region domains; point mutations; and fusion of additional proteins such as cytokines, enzymes or toxins. Specific modifications given as examples herein are the addition of an anchor domain (AD) or dimerization and docking domain (DDD) to convert the fusion protein to a DNL module. The DNL module could then be further enhanced by the conjugation of additional functional groups using the Dock-and-Lock (DNL) method.

The engineered antibodies disclosed herein may be incorporated as naked antibodies, alone or in combination with one or more therapeutic agents. Alternatively, the disclosed engineered antibodies may be utilized as immunoconjugates, attached to one or more therapeutic agents. (For methods of making immunoconjugates, see, e.g., U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.) Exemplary therapeutic agents may be selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide molecule (e.g., an antisense molecule or a gene) or a second antibody or fragment thereof.

Removable Linkers and Connectors

In some embodiments, the CL domain and VH domain of each scFab fragment are operably linked to one another via a linker. In some embodiments, the linker is a synthetic compound linker such as, for example, a chemical cross-linking agent. In some embodiments, the CL domain and VH domain of each scFab fragment are operably linked to one another via a linker polypeptide sequence (e.g., peptidal linkage). In principle, there are no particular limitations to the length and/or amino acid composition of the linker polypeptide sequence. In some embodiments, any arbitrary single-chain peptide comprising about one to 100 amino acid residues (e.g., 2, 3, 4, 5, 6, 7, 8, 9, 10, 11, 12, 13, 14, 15, 16, 17, 18, 19, 20, etc. amino acid residues) can be used as a polypeptide linker. In some embodiments, the linker polypeptide sequence includes about 5 to 50, about 10 to 60, about 20 to 70, about 30 to 80, about 40 to 90, about 50 to 100, about 60 to 80, about 70 to 100, about 30 to 60, about 20 to 80, about 30 to 90 amino acid residues. In some embodiments, the linker polypeptide sequence includes about 1 to 10, about 5 to 15, about 10 to 20, about 15 to 25, about 20 to 40, about 30 to 50, about 40 to 60, about 50 to 70 amino acid residues. In some embodiments, the linker polypeptide sequence includes about 40 to 70, about 50 to 80, about 60 to 80, about 70 to 90, or about 80 to 100 amino acid residues. In some embodiments, the linker polypeptide sequence includes about 1 to 10, about 5 to 15, about 10 to 20, about 15 to 25 amino acid residue.

In some embodiments, the CL domain and VH domain of each scFab fragment are operably linked to one another via a removable linker. In some embodiments, the amino acid sequence of the removable linker includes one or more proteolytic cleavage sites. Generally, any proteolytic cleavage site known in the art can be incorporated into the engineered antibodies of the disclosure and can be, for example, proteolytic cleavage sequences that are cleaved post-production by a protease. Further suitable proteolytic cleavage sites also include proteolytic cleavage sequences that can be cleaved following addition of an external protease.

In some embodiments, at least one of the one or more proteolytic cleavage sites can be cleaved by a protease selected from the group consisting of thrombin, PreScission™ protease, and tobacco etch virus (TEV) protease. In some embodiments, the protease is thrombin. In some embodiments, the removable linker includes a sc36TMB linker. In some embodiments, the removable linker includes the polypeptide sequence of SEQ ID NO: 80.

In some embodiments, at least one of the one or more proteolytic cleavage sites can be cleaved by an endopeptidase, which is sometimes referred to as endoproteinase or proteolytic peptidase that breaks peptide bonds of nonterminal amino acids (i.e., within the molecule), in contrast to exopeptidase, which breaks peptide bonds from end-pieces of terminal amino acids. Endopeptidases suitable for the disclosed antibodies include, but are not limited to, trypsin, chymotrypsin, elastase, thermolysin, pepsin, glutamyl endopeptidase, or neprilysin.

In some embodiments, the one or more additional scFab fragments are operably linked to the C- or N-terminus of the first and/or second polypeptide chain via a connector. In some embodiments, the connector is a synthetic compound linker such as, for example, a chemical cross-linking agent. In some embodiments, one or more additional scFab fragments are operably linked to the C- or N-terminus of the first and/or second polypeptide chain via a peptide connector. In principle, there are no particular limitations to the length and/or amino acid composition of the connector polypeptide sequence. In some embodiments, any arbitrary single-chain peptide comprising about one to 100 amino acid residues (e.g., 2, 3, 4, 5, 6, 7, 8, 9, 10, 11, 12, 13, 14, 15, 16, 17, 18, 19, 20, etc. amino acid residues) can be used as a polypeptide linker. In some embodiments, the linker polypeptide sequence includes about 5 to 50, about 10 to 60, about 20 to 70, about 30 to 80, about 40 to 90, about 50 to 100, about 60 to 80, about 70 to 100, about 30 to 60, about 20 to 80, about 30 to 90 amino acid residues.

In certain embodiments, the peptide connector contains only glycine and/or serine residues (e.g., glycine-serine linker). Examples of such peptide connectors include: Gly, Ser; Gly Ser; Gly Gly Ser; Ser Gly Gly; Gly Gly Gly Ser; Ser Gly Gly Gly; Gly Gly Gly Gly Ser; Ser Gly Gly Gly Gly; Gly Gly Gly Gly Gly Ser; Ser Gly Gly Gly Gly Gly; Gly Gly Gly Gly Gly Gly Ser; Ser Gly Gly Gly Gly Gly Gly; (Gly Gly Gly Gly Ser)n, wherein n is an integer of one or more; and (Ser Gly Gly Gly Gly)n, wherein n is an integer of one or more. In some embodiments, the peptide connectors are modified such that the amino acid sequence GSG (that occurs at the junction of traditional Gly/Ser linker peptide repeats) is not present. For example, in some embodiments, the peptide connector includes an amino acid sequence selected from the group consisting of: (GGGXX)nGGGGS and GGGGS(XGGGS)n, where X is any amino acid that can be inserted into the sequence and not result in a polypeptide comprising the sequence GSG, and n is 0 to 4. In some embodiments, the sequence of a peptide connector is (GGGX1X2)nGGGGS and X1 is P and X2 is S and n is 0 to 4. In some other embodiments, the sequence of a peptide connector is (GGGX1X2)nGGGGS and Xi is G and X2 is Q and n is 0 to 4. In some other embodiments, the sequence of a peptide connector is (GGGX1X2)nGGGGS and X1 is G and X2 is A and n is 0 to 4. In yet some other embodiments, the sequence of a peptide connector is GGGGS(XGGGS)n, and X is P and n is 0 to 4. In some embodiments, a peptide connector of the disclosure comprises or consists of the amino acid sequence $(GGGGA)_2$GGGGS. In some embodiments, the peptide connector comprises or consists of the amino acid sequence $(GGGGQ)_2$GGGGS. In another embodiment, a peptide connector comprises or consists of the amino acid sequence $(GGGPS)_2$GGGGS. In another embodiment, the peptide connector comprises or consists of the amino acid sequence GGGGS$(PGGGS)_2$. In some embodiments, the peptide connector is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In some embodiments, the peptide connector is $(G_4S)_2$. In some embodiments, the connector includes the sequence-GGGSGGGSGGGSG-(SEQ ID NO: 82). In some embodiments, the connector includes the sequence-ASTKGPSGSG-(SEQ ID NO: 81).

Affinity Tags

In some embodiments, the removable linker incorporated in each scFab fragment further includes one or more heterologous affinity tags. In some embodiments, at least one of the one or more heterologous affinity tags is incorporated at a position selected from the group consisting of the N-terminus of removable linker sequence, the C-terminus of removable linker sequence, and internal to the removable linker sequence. In some embodiments, the one or more heterologous affinity tags is selected from the group consisting of polyhistidine (poly-His) tags, Hemagglutinin (HA) tags, AviTag™, Protein C tags, FLAG tags, Strep-tag® II, and Twin-Strep-tag®, glutathione —S-transferase (GST), C-myc tag, Chitin-binding domain, Streptavidin binding proteins (SBP), maltose binding protein (MBP), Cellulose-binding domains, Calmodulin-binding peptides, and S-tags. In some embodiments, at least one of the one or more affinity tags includes a poly-His tag. In some embodiments, at least one of the one or more affinity tags includes a Twin-Strep-tag®. In some embodiments, the removable linkers of the scFab fragments of the first and second polypeptide chains includes the same affinity tags. In some embodiments, the removable linkers of the scFab fragments of the first and second polypeptide chains includes different affinity tags.

In some embodiments, the removable linker further comprises one or more additional polypeptide motifs that promote dimer formation. In some embodiments, the one or more additional polypeptide motifs are selected from the group consisting of homodimerization motifs, heterodimerization motifs, leucine zipper motifs, and combinations of any thereof. In some embodiments, at least one of the additional polypeptide motifs comprises a heterodimerization motif of the constant region of T-cell receptor alpha and/or beta chains.

Heavy-Chain Heterodimerization

As described above, the compositions and methods disclosed herein provide advantageous approaches to improving the efficiency of multispecific antibody production. An approach to circumvent the problem of mispaired byproducts, which is known as "knobs-into-holes" or "protuberance-into-cavity," aims at promoting the pairing of two different antibody heavy chains by introducing mutations into the constant domains to modify their contact interface. For example, in some embodiments, the disclosed compositions and methods involve induction of heavy chain heterodimer formation and inhibition of heavy chain homodimer formation by substituting an amino acid side chain present in a constant region (e.g., CH2 or CH3 region) of one of the heavy chains to a larger side chain to create a "knob," and substituting the amino acid side chain present in the CH3 region of the other heavy chain to a smaller side chain to create a "hole," such that the knob can be positioned into the hole. By combining these two antibody heavy chains (e.g., co-expressing in recombinant cells), high yields of heterodimer formation ("knob-hole") versus homodimer formation ("hole-hole" or "knob-knob") can be achieved. Additional information in this regard can be found in, for example, U.S. Pat. No. 8,216,805. Furthermore, the percentage of heterodimer may be further increased by the introduction of a disulfide bridge to stabilize the heterodimers or by remodeling the interaction surfaces of the two CH3 domains using a phage display approach. Additional approaches for the KIH technology can be found in, e.g. European Patent Publication No. EP 1870459A1.

In some embodiments, the Fc regions of the first and the second polypeptide chains are associated with one another via a modified interface within a constant domain of the Fc regions. In some embodiments, the first and second polypeptide chains each include an antibody constant domain such as the CH2 domain or CH3 domain of a human IgG1. In some embodiments, the first and second polypeptide chains each include a CH2 domain. In some embodiments, the first and second polypeptide chains each include a CH3 domain. In some embodiments, the first and second polypeptide chains each include the interface residues of the CH3 domain of IgG. In some embodiments, the modified interface of the first polypeptide chain includes a protuberance which is positionable in a cavity in the modified interface of the second polypeptide chain. In some embodiments, the amino acid sequence of an original interface has been modified so as to introduce the protuberance and/or cavity into the modified interface such that a greater ratio of heterodimer:homodimer forms than that for a dimer having a non-modified interface.

One skilled in the art will appreciate that the "interface" of the engineered antibodies disclosed herein includes those "contact" amino acid residues in the first polypeptide which interact with one or more "contact" amino acid residues in the interface of the second polypeptide. The interface can be a domain of an immunoglobulin such as a variable domain or constant domain (or regions thereof). In some embodiments, the interface includes the CH2 domain and/or CH3 domain of an immunoglobulin. In some embodiments, the interface includes the CH2 domain and/or CH3 domain of an IgG antibody. In some embodiments, the interface includes the CH2 domain and/or CH3 domain of a human IgG1 antibody.

A "cavity" refers to at least one amino acid side chain which is recessed from the interface of the second polypeptide and therefore accommodates a corresponding protuberance on the adjacent interface of the first polypeptide. A "protuberance" refers to at least one amino acid side chain which projects from the interface of the first polypeptide and is therefore positionable in a compensatory cavity in the adjacent interface (i.e., the interface of the second polypeptide) so as to stabilize the heterodimer, and thereby favor heteromultimer formation over homodimer formation, for example. "Protuberances" are constructed by replacing small amino acid side chains from the interface of the first polypeptide with larger side chains (e.g., tyrosine or tryptophan). Compensatory "cavities" of identical or similar size to the protuberances are optionally created on the interface of the second polypeptide by replacing large amino acid side chains with smaller ones (e.g., alanine or threonine). In instances where a suitably positioned and dimensioned protuberance or cavity already exists at the unmodified interface of either the first or second polypeptide, it is only necessary to engineer a corresponding cavity or protuberance, respectively, at the adjacent interface. Additional information regarding KIH technology can be found in, e.g., U.S. Pat. No. 8,679,785, which is hereby incorporated by referenced.

In some embodiments, the cavity includes an amino acid residue substituted into the interface of the second polypeptide, and wherein the substituted amino acid residue is selected from the group consisting of alanine (A), serine (S), threonine (T), and valine (V). In some embodiments, the protuberance includes an amino acid residue substituted into the interface of the first polypeptide, and wherein the substituted amino acid residue is selected from the group consisting of arginine (R), phenylalanine (F), tyrosine (Y), and tryptophan (W). In some embodiments, the amino acid residue is substituted into the interface of the first polypeptide at a position corresponding to a contact residue of the CH3 domain of human IgG1, as indicated in FIG. 7 of U.S. Pat. No. 8,679,786, which is incorporated herein by reference. In some embodiments, the amino acid residue is substituted into the interface of the first polypeptide at position 347, 349, 350, 351, 366, 368, 370, 392, 394, 395, 397, 398, 399, 405, 407, or 409 of the CH3 domain of human IgG1. In some embodiments, the protuberance includes a T366W amino acid substitution within the constant domain CH3 of the Fc region of the first polypeptide. In some embodiments, the cavity includes an amino acid substitution selected from the group consisting of S354C, T366S, L368A, and Y407V present within the constant domain CH3 of the Fc region of the second polypeptide.

In some embodiments, the engineered antibody or functional fragment thereof as described herein includes a single-chain polypeptide with an amino acid sequence having at least 80% sequence identity to any one of the amino acid sequences disclosed herein. In some embodiments, at least one of the first and second polypeptides includes a single-chain polypeptide with an amino acid sequence having at least 80%, 90%, 95%, 96%, 97, 98%, 99% sequence identity to any one of the amino acid sequences disclosed herein. In some embodiments, at least one of the first and second polypeptides includes an amino acid sequence having at least 80%, 90%, 95%, 96%, 97, 98%, 99% sequence identity to any one of the amino acid sequences identified in the Sequence Listing. In some embodiments, at least one of the first and second polypeptides includes an amino acid sequence having at least 80%, 90%, 95%, 96%, 97, 98%, 99% sequence identity to any one of SEQ ID NOS: 1-12. In some embodiments, at least one of the first and second polypeptides includes an amino acid sequence having at least 80%, 90%, 95%, 96%, 97, 98%, 99% sequence identity to SEQ ID NO: 1. In some embodiments, at least one of the first and second polypeptides includes an amino acid sequence having at least 80%, 90%, 95%, 96%, 97, 98%, 99% sequence identity to SEQ ID NO: 2. In some embodiments, at least one of the first and second polypeptides includes an amino acid sequence having at least 80%, 90%, 95%, 96%, 97, 98%, 99% sequence identity to SEQ ID NO: 3. In some embodiments, at least one of the first and second polypeptides includes an amino acid sequence having at least 80%, 90%, 95%, 96%, 97, 98%, 99% sequence identity to SEQ ID NO: 4. In some embodiments, at least one of the first and second polypeptides includes an amino acid sequence having at least 80%, 90%, 95%, 96%, 97, 98%, 99% sequence identity to SEQ ID NO: 5. In some embodiments, at least one of the first and second polypeptides includes an amino acid sequence having at least 80%, 90%, 95%, 96%, 97, 98%, 99% sequence identity to SEQ ID NO: 6.

In some embodiments, the engineered antibody or functional fragment thereof as described herein includes at least one of the first and second polypeptides with an amino acid sequence having at least 80%, 90%, 95%, 96%, 97, 98%, 99% sequence identity to SEQ ID NO: 7. In some embodiments, at least one of the first and second polypeptides includes an amino acid sequence having at least 80%, 90%, 95%, 96%, 97, 98%, 99% sequence identity to SEQ ID NO: 8. In some embodiments, at least one of the first and second polypeptides includes an amino acid sequence having at least 80%, 90%, 95%, 96%, 97, 98%, 99% sequence identity to SEQ ID NO: 9. In some embodiments, at least one of the first and second polypeptides includes an amino acid sequence having at least 80%, 90%, 95%, 96%, 97, 98%, 99% sequence identity to SEQ ID NO: 10. In some embodiments, at least one of the first and second polypeptides includes an amino acid sequence having at least 80%, 90%, 95%, 96%, 97, 98%, 99% sequence identity to SEQ ID NO: 11. In some embodiments, at least one of the first and second polypeptides includes an amino acid sequence having at least 80%, 90%, 95%, 96%, 97, 98%, 99% sequence identity to SEQ ID NO: 12.

It is also contemplated that alternative methodologies can be used to promote heavy-chain heterodimerization of the first and second polypeptide chains of the engineered antibodies of the disclosure. For example, in some embodiments, the heavy-chain heterodimerization of the first and second polypeptide chains of the engineered antibodies as disclosed herein can be achieved by a controlled Fab arm exchange method as described in Aran F L et al., *Proc. Natl. Acad. Sci. U.S.A, Mar.* 26, 2013, vol. 110, no. 13, 5145-5150, which is hereby incorporated by referenced in its entirety.

Making Antibodies

One skilled in the art will appreciate that the complete amino acid sequence of an antibody can be used to construct a back-translated gene. For example, a DNA oligomer containing a nucleotide sequence coding for a given polypeptide can be synthesized. For example, several small oligonucleotides coding for portions of the desired polypeptide can be synthesized and then ligated. The individual oligonucleotides generally contain 5' or 3' overhangs for complementary assembly. In some cases, the individual oligonucleotides can contain 5' and 3' blunt-ends, which can also be assembled by using, e.g., blunt-end ligases.

In addition to generating polypeptides via expression of nucleic acid molecules that have been assembled by recombinant molecular biological techniques, a subject engineered antibody in accordance with the present disclosure can be chemically synthesized. Chemically synthesized polypeptides are routinely generated by those of skill in the art.

Once assembled (by synthesis, site-directed mutagenesis or another method), the DNA sequences encoding an engineered antibody as disclosed herein can be inserted into an expression vector and operably linked to an expression control sequence appropriate for expression of the engineered antibody in the desired transformed host. Proper assembly can be confirmed by nucleotide sequencing, restriction mapping, and expression of the engineered antibody in a suitable host. As is known in the art, in order to obtain high expression levels of a transfected gene in a host, the gene must be operably linked to transcriptional and translational expression control sequences that are functional in the chosen expression host.

The binding activity of the engineered antibodies of the disclosure can be assayed by any suitable method known in the art. For example, the binding activity of the engineered antibodies of the disclosure can be determined by, e.g., Scatchard analysis (Munsen, et al. 1980 Analyt. Biochem. 107:220-239). Specific binding may be assessed using techniques known in the art including but not limited to competition ELISA, BIACORE® assays and/or KINEXA® assays. An antibody that "preferentially binds" or "specifically binds" (used interchangeably herein) to a target antigen or target epitope is a term well understood in the art, and methods to determine such specific or preferential binding are also known in the art. An antibody is said to exhibit "specific binding" or "preferential binding" if it reacts or associates more frequently, more rapidly, with greater duration and/or with greater affinity with a particular antigen or epitope than it does with alternative antigens or epitopes. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. For example, an antibody that specifically or preferentially binds to a HER2 epitope is an antibody that binds this epitope with greater affinity, avidity, more readily, and/or with greater duration than it binds to other HER2 epitopes or non-HER2 epitopes. It is also understood by reading this definition, for example, that an antibody which specifically or preferentially binds to a first target antigen may or may not specifically or preferentially bind to a second target antigen. As such, "specific binding" or "preferential binding" does not necessarily require (although it can include) exclusive binding.

A variety of assay formats may be used to select an antibody that specifically binds an antigen of interest. For example, solid-phase ELISA immunoassay, immunoprecipitation, Biacore™ (GE Healthcare, Piscataway, NJ), KinExA, fluorescence-activated cell sorting (FACS), Octet™ (ForteBio, Inc., Menlo Park, CA) and Western blot analysis are among many assays that may be used to identify an antibody that specifically reacts with an antigen. Generally, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background.

Nucleic Acids and Recombinant Cells

In one aspect, some embodiments disclosed herein relate to nucleic acid molecules encoding the multispecific antibodies of the disclosure, expression cassettes, and expression vectors containing these nucleic acid molecules operably linked to regulator sequences which allow expression of the multispecific antibodies in a host cell or ex-vivo cell-free expression system.

The terms "nucleic acid molecule" and "polynucleotide" are used interchangeably herein, and refer to both RNA and DNA molecules, including nucleic acid molecules including cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be nucleic acid molecules of any length, including nucleic acid molecules that are generally between about 5 Kb and about 50 Kb, for example between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

In some embodiments, the nucleic acid molecules of the disclosure are recombinant, e.g. nucleic acid molecules that have been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence.

In some embodiments, provided herein are nucleic acid molecules including a nucleotide sequence that encodes the first and/or the second polypeptide chain of an engineered antibody as disclosed herein. In some embodiments, a nucleic acid molecule as disclosed herein encodes at least one of the first and the second polypeptide chain of an engineered antibody as disclosed herein. In some embodiments, a nucleic acid molecule as disclosed herein encodes both the first and the second polypeptide chain of an engineered antibody as disclosed herein.

In some embodiments, the nucleic acid molecules include a nucleotide sequence encoding a single chain polypeptide with an amino acid sequence having at least 80%, 90%, 95%, 96%, 97, 98%, 99% sequence identity to the first or the second polypeptide chain of an engineered antibody as disclosed herein. In some embodiments, the nucleic acid molecules include a nucleotide sequence encoding a single chain polypeptide with an amino acid sequence having at least 80%, 90%, 95%, 96%, 97, 98%, 99% sequence identity to any one of SEQ ID NOS: 1-12 in the Sequence Listing. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 1. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 2. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 3. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 4. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 5. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 6.

In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 7. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 8. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 9. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 10. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 11. In some embodiments, the nucleic acid molecules include a nucleotide sequence encoding a single chain polypeptide with an amino acid sequence having at least 80%, 90%, 95%, 96%, 97, 98%, 99% sequence identity to SEQ ID NO: 12.

Some embodiments disclosed herein relate to vectors or expression cassettes including a recombinant nucleic acid molecule encoding the engineered antibodies as disclosed herein. The term expression cassette generally refers to a construct of genetic material that contains coding sequences and sufficient regulatory information to direct proper transcription and/or translation of the coding sequences in a recipient cell, in vivo and/or ex vivo. The expression cassette may be inserted into a vector for targeting to a desired host cell and/or into a subject. As such, the term expression cassette may be used interchangeably with the term "expression construct." As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, e.g. operably linked.

Also provided herein are vectors, plasmids, or viruses containing one or more of the nucleic acid molecules encoding any of the engineered antibodies disclosed herein. The nucleic acid molecules described above can be contained within a vector that is capable of directing their expression in, for example, a cell that has been transformed/transduced with the vector. Suitable vectors for use in eukaryotic and prokaryotic cells are known in the art and are commercially available or readily prepared by a skilled artisan. Additional vectors can also be found, for example, in Ausubel, F. M., et al., *Current Protocols in Molecular Biology*, New York, NY: Wiley (including supplements through 2014), and Sambrook, J., & Russell, D. W. (2012). *Molecular Cloning: A Laboratory Manual* (4th ed.). Cold Spring Harbor, NY: Cold Spring Harbor Laboratory and Sambrook, J., & Russel, D. W. (2001).

It should be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the engineered antibodies of the present disclosure to be amplified in copy number. Such amplifiable vectors are known in the art.

Accordingly, in some embodiments, the engineered antibodies as described herein, can be expressed from vectors, preferably expression vectors. The vectors are useful for autonomous replication in a host cell or may be integrated into the genome of a host cell upon introduction into the host cell, and thereby are replicated along with the host genome (e.g., non-episomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are also included. Exemplary recombinant expression vectors can include one or more regulatory sequences, selected on the basis of the host cells to be used for expression, operably linked to the nucleic acid sequence to be expressed.

DNA vector can be introduced into prokaryotic or eukaryotic cells via conventional transformation or transfection techniques. Suitable methods for transforming or transfecting host cells can be found in Sambrook et al. (2001, supra) and other standard molecular biology laboratory manuals.

The nucleic acid sequences encoding the engineered antibodies of the disclosure, can be optimized for expression in the host cell of interest. For example, the G-C content of the sequence can be adjusted to levels average for a given cellular host, as calculated by reference to known genes expressed in the host cell. Methods for codon optimization are known in the art. Codon usages within the coding sequence of the engineered antibodies disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria, the pMSXND expression vector for use in mammalian cells, and baculovirus-derived vectors for use in insect cells. In some embodiments, nucleic acid inserts, which encode the engineered antibody in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the subject polypeptide, particularly as regards potential secondary structures. Hosts should be selected by consideration of their compatibility with the chosen vector, the toxicity of the product coded for by the DNA sequences of this disclosure, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The choice of expression control sequence and expression vector, in some embodiments, will depend upon the choice of host. A wide variety of expression host/vector combinations can be employed. Non-limiting examples of useful expression vectors for eukaryotic hosts, include, for example, vectors with expression control sequences from SV40, bovine papilloma virus, adenovirus and cytomegalovirus. Non-limiting examples of useful expression vectors for bacterial hosts include known bacterial plasmids, such as plasmids from *E. coli*, including col El, pCRI, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Non-limiting examples of useful expression vectors for yeast cells include the 2μ plasmid and derivatives thereof. Non-limiting examples of useful vectors for insect cells include pVL 941 and pFastBac™ 1.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

In one aspect of the disclosure, recombinant prokaryotic or eukaryotic cells that contain an engineered antibody as disclosed herein, and/or contain and express a nucleic acid molecule that encodes any one of the engineered antibody disclosed herein are also features of the disclosure. In some embodiments, provided herein are recombinant cells including the first polypeptide chain of an engineered antibody as disclosed herein, or a scFab fragment thereof. In some embodiments, provided herein are recombinant cells including the second polypeptide chain of an engineered antibody as disclosed herein, or a scFab fragment thereof. In some embodiments, provided herein are recombinant cells including both the first and second polypeptide chains of an engineered antibody as disclosed herein. In some embodiments, the recombinant cells include a recombinant nucleic acid as disclosed herein.

In some embodiments, a recombinant cell of the disclosure is a transfected cell, e. g., a cell into which a nucleic acid molecule, for example a nucleic acid molecule encoding an engineered antibody disclosed herein, has been introduced by means of recombinant methodologies and techniques. The progeny of such a cell are also considered within the scope of the disclosure. In some embodiments, the recombinant cell is a prokaryotic cell or a eukaryotic cell. In some embodiments, the eukaryotic cell is a HEK293A cell, a Jurkat cell, or an MCF7 cell.

Cell cultures containing at least one recombinant cell as disclosed herein are also within the scope of the present disclosure. The terms, "cell", "cell culture", "cell line", "recombinant host cell", "recipient cell" and "host cell" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

The precise components of the expression system are not critical. For example, an engineered antibody as disclosed herein can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, care should be taken to ensure that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed antibody can be purified from the expression system using routine biochemical procedures, and can be used, e.g., as therapeutic agents, as described herein.

In some embodiments, engineered antibodies obtained will be glycosylated or unglycosylated depending on the host organism used to produce the engineered antibodies. If bacteria are chosen as the host then the engineered antibodies produced will be unglycosylated. Eukaryotic cells, on the other hand, will glycosylate the engineered antibodies, although perhaps not in the same way as native polypeptides is glycosylated. The recombinant antibodies produced by the transformed host can be purified according to any suitable methods known in the art. Produced recombinant antibodies can be isolated from inclusion bodies generated in bacteria such as *E. coli*, or from conditioned medium from either mammalian or yeast cultures producing an engineered antibody of the disclosure using cation exchange, gel filtration, and or reverse phase liquid chromatography.

In addition or alternatively, another exemplary method of constructing a DNA sequence encoding the engineered antibodies of the disclosure is by chemical synthesis. This includes direct synthesis of a peptide by chemical means of the amino acid sequence encoding for an engineered antibody exhibiting the properties described. This method can incorporate both natural and unnatural amino acids at positions that affect the binding affinity of the engineered antibodies with a target protein. Alternatively, a gene which encodes the desired engineered antibodies can be synthesized by chemical means using an oligonucleotide synthesizer. Such oligonucleotides are designed based on the amino acid sequence of the desired engineered antibodies, and preferably selecting those codons that are favored in the host cell in which the engineered antibody of the disclosure will be produced. In this regard, it is well recognized in the art that the genetic code is degenerate such that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated by those skilled in the art that for a given DNA sequence encoding a particular engineered antibody, there will be many DNA degenerate sequences that will code for that engineered antibody. For example, it will be appreciated that in addition to the DNA sequences for engineered antibodies provided herein, there will be many degenerate DNA sequences that code for the engineered antibodies disclosed herein. These degenerate DNA sequences are considered within the scope of this disclosure. Therefore, "degenerate variants thereof" in the context of this disclosure means all DNA sequences that code for and thereby enable expression of a particular engineered antibody.

The DNA sequence encoding the subject engineered antibody, whether prepared by site directed mutagenesis, chemical synthesis or other methods, can also include DNA sequences that encode a signal sequence. Such signal sequence, if present, should be one recognized by the cell chosen for expression of the engineered antibody. It can be prokaryotic, eukaryotic or a combination of the two. In general, the inclusion of a signal sequence depends on whether it is desired to secrete the engineered antibody as disclosed herein from the recombinant cells in which it is made. If the chosen cells are prokaryotic, it generally is preferred that the DNA sequence not encode a signal sequence. If the chosen cells are eukaryotic, it generally is preferred that a signal sequence be included.

The nucleic acid molecules provided can contain naturally occurring sequences, or sequences that differ from those that occur naturally, but, due to the degeneracy of the genetic code, encode the same polypeptide, e.g., antibody. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

The nucleic acid molecules are not limited to sequences that encode polypeptides (e.g., antibodies); some or all of the non-coding sequences that lie upstream or downstream from a coding sequence (e.g., the coding sequence of an engineered antibody) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding an engineered antibody disclosed herein) is incorporated into a vector (e.g., a plasmid or viral vector) or into the genome of a heterologous cell (or the genome of a homologous cell, at a position other than the natural chromosomal location).

Pharmaceutical Compositions

In some embodiments, the engineered antibodies of the disclosure, and/or nucleic acids as described herein, can be incorporated into compositions, including pharmaceutical compositions. Such compositions generally include the engineered antibodies and/or nucleic acids of the disclosure and, optionally, a pharmaceutically acceptable carrier. As used herein, the term “pharmaceutically acceptable carrier” includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound (e.g., engineered antibodies, and/or nucleic acid molecules of the disclosure) can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches, and the like, can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, the subject engineered antibodies of the disclosure are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the subject engineered antibodies of the disclosure can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the engineered antibodies of the disclosure can also be prepared in the form of suppositories (e.g., with conventional suppository bases such as cocoa butter and other glycerides) or retention enemas for rectal delivery.

In some embodiments, the engineered antibodies of the disclosure can also be administered by transfection or infection using methods known in the art, including but not limited to the methods described in McCaffrey et al. (Nature 418:6893, 2002), Xia et al. (Nature Biotechnol. 20: 1006-1010, 2002), or Putnam (Am. J. Health Syst. Pharm. 53: 151-160, 1996, erratum at Am. J. Health Syst. Pharm. 53:325, 1996).

In one embodiment, the subject engineered antibodies of the disclosure are prepared with carriers that will protect the engineered antibodies against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, the engineered antibodies of the disclosure can be further modified to prolong their half-life in vivo and/or ex vivo. Non-limiting examples of known strategies and methodologies suitable for modifying the engineered antibodies of the disclosure include (1) chemical modification of an engineered antibody described herein with highly soluble macromolecules such as polyethylene glycol ("PEG") which prevents the engineered antibody from contacting with proteases; and (2) covalently linking or conjugating an engineered antibody described herein with a stable protein such as, for example, albumin. Accordingly, in some embodiments, the engineered antibodies of the disclosure can be fused to a stable protein, such as, albumin. For example, human albumin is known as one of the most effective proteins for enhancing the stability of polypeptides fused thereto and there are many such fusion proteins reported.

In some embodiments, the engineered antibodies of the disclosure are chemically modified with one or more polyethylene glycol moieties, e.g., PEGylated; or with similar modifications, e.g. PASylated. In some embodiments, the PEG molecule or PAS molecule is conjugated to one or more amino acid side chains of the interferon. In some embodiments, the PEGylated or PASylated antibody contains a PEG or PAS moiety on only one amino acid. In other embodiments, the PEGylated or PASylated antibody contains a PEG or PAS moiety on two or more amino acids, e.g., attached to two or more, five or more, ten or more, fifteen or more, or twenty or more different amino acid residues. In some embodiments, the PEG or PAS chain is 2000, greater than 2000, 5000, greater than 5,000, 10,000, greater than 10,000, greater than 10,000, 20,000, greater than 20,000, and 30,000 Da. The engineered antibodies may be coupled directly to PEG or PAS (e.g., without a linking group) through an amino group, a sulfhydryl group, a hydroxyl group, or a carboxyl group.

In some embodiments, the pharmaceutical compositions of the disclosure includes one or more pegylation reagent. As used herein, the term "PEGylation" means and refers to modifying a protein by covalently attaching polyethylene glycol (PEG) to the protein, with "PEGylated" referring to a protein having a PEG attached. A range of PEG, or PEG derivative sizes with optional ranges of from about 10,000 Daltons to about 40,000 Daltons may be attached to the engineered antibodies of the disclosure using a variety of chemistries. In some embodiments, the pegylation reagent is selected from methoxy polyethylene glycol-succinimidyl propionate (mPEG-SPA), mPEG-succinimidyl butyrate (mPEG-SBA), mPEG-succinimidyl succinate (mPEG-SS), mPEG-succinimidyl carbonate (mPEG-SC), mPEG-Succinimidyl Glutarate (mPEG-SG), mPEG-N-hydroxyl-succinimide (mPEG-NHS), mPEG-tresylate and mPEG-aldehyde. In some embodiments, the pegylation reagent is methoxy polyethylene glycol-succinimidyl propionate; preferably said pegylation reagent is methoxy polyethylene glycol-succinimidyl propionate 5000 with an average molecular weight of 5,000 Daltons.

Methods of the Disclosure

Methods for Preparing Engineered Antibodies

As described above, multispecific antibodies are capable of recognizing multiple ligands simultaneously or synergistically, creating complex biological interactions not achievable by monoclonal antibodies, thus expanding opportunities for novel therapy development. With the large number of monoclonal antibodies either approved or under clinical development, there are numerous opportunities to combine their specificities to further improve therapeutic potential. Although seemingly simple in concept, clinical development of multispecific antibodies face several challenges, chief of which is how to efficiently and reliably produce bispecific and multispecific antibodies with expected specificity and desired biophysical properties. Some embodiments of the disclosure provide a modular approach that uses temporary linkers to enforce proper chain pairing and proteases such as thrombin to remove those linkers from the final product. When combined with the "knob-into-hole" design, IgG-like, multispecific antibodies can be generated from any pre-existing monoclonal antibodies. The approach disclosed herein is highly versatile and applicable to any monoclonal antibody pair or panel, expediting evaluation and therapeutic development of multispecific antibodies.

In some embodiments, the present disclosure describes a technology that enables modular construction of multispecific antibodies. An exemplary production scheme involves the use of a protease sensitive linker to connect the cognate heavy and light chains to re-enforce the correct pairing, which is then removed by protease such as thrombin. As discussed above, affinity tags can also be built into the linker for further purification of the desired heterodimer before protease cutting. The technology allows facile production of IgG-like bispecific as well as multispecific antibodies with Fab as the binding unit. The technology is modular in nature, analogous to building LEGO toys. Hence, the multispecific antibodies generated by this technology are termed "Lego-Bodies".

As described in greater detail herein, an advantageous and modular platform has been developed to generate bispecific and multispecific antibodies from any pre-existing monoclonal antibody. The use of thrombin-removable linkers enforces correct pairing of light and heavy chains and enables efficient in vitro removal of these linkers following purification. Comparing other bispecific formats, such as the CrossMAb or common light chain IgG molecules, the disclosed format requires minimal efforts in design and optimization, imposes no restrictions on the underlying monoclonal antibody (the building block), and can be used as tools to readily generate and evaluate bispecific antibodies from any two monoclonal antibodies of interest. The linker employed herein to enforce proper chain paring is very malleable and can be used to introduce versatile features to aid purification. As an exemplification, different affinity tags have been designed into the linker, and demonstrated that sequential purification by affinity chromatography can effectively eliminate homodimer contaminations. Other features such as asymmetric length or charge (isoelectric point) can be incorporated into the linker to customize the purification scheme.

The disclosed approach, which is modular in nature and permits Lego-like assembly, has been expanded to multispecific antibody generation. As described in Examples 6, two classes of tri-specific and tetra-specific antibodies have been generated by appending additional Fab domains to either the N-terminus of the light chain or the C-terminus of the heavy chain in the starting bispecific molecule. The added Fab domains also use thrombin-removable linkers to enforce correct heavy and light chain pairing. Several tri- and tetra-specific molecules have been successfully generated and their binding verified to corresponding ligands. Given the modular nature of the process, the approach disclosed herein should be applicable to the generation of even higher order of specificities. Given the explosion of information on the molecular mechanism of human diseases and the rapid expansion of the list of potential targets, multispecific antibodies are likely to become an expanding class of novel therapeutics due to their unique ability to generate synergistic or synthetic interactions among targets, thus uncovering new biology and targeting opportunities.

In one aspect, provided herein are various methods for preparing an engineered antibody, including: (a) providing an engineered antibody as disclosed herein; and (b) removing the removable linker to produce an antibody product that does not contain the removable linker.

Non-limiting exemplary embodiments of the disclosed methods for preparing an engineered antibody include one or more of the following features. In some embodiments, the engineered antibody is provided by culturing a host cell that co-expresses the first and the second polypeptide chains of the engineered antibody. In some embodiments, the engineered antibody is provided by co-expressing the first and the second polypeptide chains in the same recombinant cell. Alternatively, in some embodiments, the first and the second polypeptide chains are individually expressed from different recombinant cells, and subsequently combined, ex vivo or in vitro, to generate a fully assembled antibody having the first and the second polypeptide chains associated with one another.

In some embodiments, the methods for preparing an engineered antibody further include a purification process. The purification process can be carried out by essentially separating the engineered antibody from undesirable impurities present in the expression/processing system, such as host cell debris, aggregated unfolded polypeptides, homodimers, and/or incorrectly folded polypeptides which should not be present in the intermediate or final product. The term "impurity" as used herein, in the broadest sense, to refer to any substance which differs from the engineered antibody such that the engineered antibody is not pure. The impurity can include host cell substances such as nucleic acids, lipids, polysaccharides, proteins, etc.; culture medium, and additives which are used in the preparation and processing of the engineered antibody. In some embodiments, the impurity can include one or more of the following substances: monomeric scIgG, incorrectly folded molecules of scIgG, mispaired byproducts (e.g., "hole-hole" or "knob-knob" homodimers), antibodies with incomplete removal of the linker, and host cell proteins.

The purity of the multispecific antibody products can be assessed by using any suitable analytical techniques known in the art, such as SDS-PAGE, hydrophobic interaction chromatography (HIC), or HIC-HPLC as described in Examples 2 and 4-5 and illustrated in FIGS. 2-3.

In some embodiments, the antibody produced by the disclosed methods includes the engineered antibody with a purity of greater than about 70%. In some embodiments, the antibody produced by the disclosed methods includes the engineered antibody with a purity of greater than about 70%, about 75%, about 80%, about 85%, about 90%, or about 95%. In some embodiments, the antibody produced by the disclosed methods includes the engineered antibody with a purity ranging from about 70% to about 100%, from about 80% to about 95%, from about 90% to about 99%, from about 75% to about 95%, from about 85% to about 100%, or from about 95% to about 100%. In some embodiments, the antibody produced by the disclosed methods includes the engineered antibody lacking the removable linker with a purity of greater than about 70%. In some embodiments, the antibody produced by the disclosed methods includes the engineered antibody lacking the removable linker with a purity of greater than about 70%, about 75%, about 80%, about 85%, about 90%, or about 95%. In some embodiments, the antibody produced by the disclosed methods includes the engineered antibody lacking the removable linker with a purity ranging from about 70% to about 100%, from about 80% to about 95%, from about 90% to about 99%, from about 75% to about 95%, from about 85% to about 100%, or from about 95% to about 100%.

In some embodiments, the first and the second polypeptide chains are individually expressed from different recombinant cells and purified before they are subsequently combined, ex vivo or in vitro, to generate a fully assembled antibody having the first and the second polypeptide chains are associated with one another. In some embodiments, the engineered antibody is further purified before the removal of the removable linker originally embedded within the scFab fragments. In some embodiments, the engineered antibody is purified after the removal of the removable linker originally embedded within the scFab fragments. In some embodiments, various purification processed can be performed both prior to and after removal of the removable linker(s).

In some embodiments, the purifying process includes one or more techniques selected from the group consisting of affinity chromatography, ion-exchange chromatography (IEC), anion exchange chromatography (AEX), cation exchange chromatography (CEX), hydroxyapatite chromatography, hydrophobic interaction chromatography (HIC), metal affinity chromatography, and mixed mode chromatography (MMC).

In some embodiments, the purifying process includes affinity chromatography, e.g., subjecting a sample containing the engineered antibody to a suitable affinity chromatographic support. Non-limiting examples of such chromatographic supports include, but are not limited to Protein A resin, Protein G resin, affinity supports comprising an antigen against which the antibody of interest was raised, and affinity supports comprising an Fc binding protein. In some embodiments, the affinity chromatography includes protein A affinity chromatography.

In some embodiments, the purifying process can be carried out using ion-exchange chromatography (IEC) in order to remove other contaminants. In principle, cation exchange chromatography (CEX) and/or anion exchange chromatography (AEX) can be suitably used. Generally, the AEX chromatography can be performed by using any one of functional groups known for AEX chromatography of proteins. These groups include diethylaminoethyl (DEAE), trimethylaminoethyl (TMAE), quaterny aminomethyl (Q), and quaterny aminoethyl (QAE). These are commonly used functional anion exchange groups for biochromatographic processes. Suitable functional groups used for CEX chromatography include, but are not limited to, carboxymethyl (CM), sulfonate (S), sulfopropyl (SP) and sulfoethyl (SE). These are commonly used cation exchange functional groups for biochromatographic processes.

Throughout this specification, various patents, patent applications and other types of publications (e.g., journal articles, electronic database entries, etc.) are referenced. The disclosure of all patents, patent applications, and other publications cited herein are hereby incorporated by reference in their entirety to the same extent as if each individual publication or patent application was specifically and individually indicated to be incorporated by reference.

No admission is made that any reference cited herein constitutes prior art. The discussion of the references states what their authors assert, and Applicant reserves the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Additional embodiments are disclosed in further detail in the following examples, which are provided by way of illustration and are not in any way intended to limit the scope of this disclosure or the claims.

EXAMPLES

Example 1

General Experimental Procedures

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* (4th ed.). Cold Spring Harbor, NY: Cold Spring Harbor Laboratory and Sambrook, J., & Russel, D. W. (2001). *Molecular Cloning: A Laboratory Manual* (3rd ed.). Cold Spring Harbor, NY: Cold Spring Harbor Laboratory (jointly referred to herein as "Sambrook"); Ausubel, F. M. (1987). *Current Protocols in Molecular Biology*. New York, NY: Wiley (including supplements through 2014); Bollag, D. M. et al. (1996). *Protein Methods*. New York, NY: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, CA: Academic Press; Lefkovits, I. (1997). *The Immunology Methods Manual: The Comprehensive Sourcebook of Techniques*. San Diego, CA: Academic Press; Doyle, A. et al. (1998). *Cell and Tissue Culture: Laboratory Procedures in Biotechnology*. New York, NY: Wiley; Mullis, K. B., Ferré, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, NY: Cold Spring Harbor Laboratory Press; Beaucage, S. L. et al. (2000). *Current Protocols in Nucleic Acid Chemistry*. New York, NY: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference.

Example 2

Additional Experimental Procedures

Monoclonal Antibody Expression and Purification

Genes encoding antibody variable domains were synthesized by gBlock® (Integrated DNA Technologies). Plasmids for the heavy and light chains for each antibody were separately cloned in the Abvec vector as previously described (Lee N K et al. Scientific Reports 2018; 8:766, and Smith K. et al. Nat Protoc 2009; 4:372-84). Generally, antibodies were produced by co-transfecting plasmids expressing the heavy and light chains at a 1:1 ratio in HEK293A cells for 6-8 days, followed by purification of culture supernatant on protein A agarose (Pierce/Thermo Scientific).

Monoclonal Single-Chain IgG Expression and Purification

The sc36TMB linker (SEQ ID NO: 80) and the heavy chain variable domains were fused by PCR reaction. The resultant DNA fragment was subcloned into Ig-γ Abvec vector (NovoPro) and subsequently fused with the heavy chain constant domain and Fc fragment to generate the complete single-chain IgG (scIgG) (see, e.g., SEQ ID NOs: 1-2 and FIGS. 1A-1D). The resulting plasmid was transfected into HEK293A cells and scIgG molecules were purified from culture supernatant by protein A agarose (Pierce—Thermo Scientific).

Thrombin Cleavage and Removal of the Enzyme

To remove the sc36TMB linker, the scIgG prepared as described above was mixed with thrombin at the ratio of 50-100 μg antibody per unit of thrombin (Millipore, 605160), and the mixture was incubated at 37° C. for 2 hours. The processed IgG molecule was re-purified by protein A agarose to remove the enzyme. The conversion of the scIgG to IgG was verified by SDS-PAGE with reducing agent added to the sample.

Bispecific Antibody Expression and Purification

The "knob" Fc (T366W) or "hole" Fc (T366S/L368A/Y407V) fragments[41,42] were introduced to the Ig-γ chain by site-directed mutagenesis. The fused gene encoding the complete light chain, sc36TMB linker, and heavy chain variable domain was subcloned into either the "knob" or "hole" vector as described in greater detail below, for example in Examples 3-6, SEQ ID NOS: 3-5, and FIGS. 2A-2L. To produce the scIgG bispecific antibody, a pair of the "knob" and "hole" vectors, each encoding one scIgG antibody chain, were co-transfected into HEK293A cells at a 1:1 ratio. After culturing for 6-8 days, the bispecific scIgG was purified from culture supernatant by protein A agarose. The sc36TMB linkers in the bispecific scIgG were then removed by thrombin cleavage as described above, yielding the bispecific IgG. Detailed information for various exemplary single-chain polypeptides of the disclosure can be found in Table 1 below.

TABLE 1

This table provides a brief description for each of the single-chain polypeptides, their corresponding components, as well as corresponding sequence identifiers as set forth in the Sequence Listing. Atez: Atezolizumab; Dara: Daratumumab; Her: Herceptin; Ipil: Ipilimumab.

| Description | Sequence SEQ ID NO |
|---|---|
| Light chain (Ipil)-sc36TMB linker-Heavy chain (Ipil)-Fc region | 1 |
| Light chain (Dara)-sc36TMB linker-Heavy chain (Dara)-Fc region | 2 |
| Light chain (Ipil)-sc36TMB linker-Heavy chain (Ipil)-Fc region (Hole) | 3 |
| Light chain (Dara)-sc36TMB linker- Heavy chain (Dara)-Fc region (Knob) | 4 |
| Light chain (Her)-sc36TMB linker-Heavy chain (Her)-Fc (Knob) | 5 |
| Light chain (Ipil)-sc36TMB linker Twin Strep tag-Heavy chain (Ipil)-Fc (Hole) | 6 |
| Light chain (Dara)-sc36TMB linker 10xHisTag-Heavy chain (Dara)-Fc (Knob) | 7 |
| Light chain (Her)-sc36TMB linker 10xHisTag-Heavy chain (Her)-Fc (Knob) | 8 |
| Light chain (Her)-sc36TMB linker-heavy chain(Her)-N-linker-Light chain (Ipil)-sc36TMB linker-Heavy chain (Ipil)-Fc region (Hole) | 9 |
| Light chain (Atez)-sc36TMB linker-heavy chain(Atez)-N-linker-Light chain (Dara)-sc36TMB linker-Heavy chain (Dara)-Fc region (Knob) | 10 |
| Light chain (Ipil)-sc36TMB linker-heavy chain (ipil)-Fc region (Hole)-C-linker- Light chain (Her)-sc36TMB linker-Heavy chain (Her) | 11 |
| Light chain (Dara)-sc36TMB linker-Heavy chain (Dara)-Fc region (Knob) - C-linker - Light chain (Atez)-sc36TMB linker-Heavy chain (Atez) | 12 |

Tri-Specific and Tetra-Specific Antibody Expression and Purification

The AgeI restriction site between the sequences encoding the signal peptide and N-terminus of the antibody gene in the Abvec vector was retrained in the construct for scIgG with either the "knob" or "hole" Fc fragment. This AgeI site was used to introduce an additional Fab gene (with a thrombin removable linker in-between the light and heavy chain) and the N-linker (-ASTKGPSGSG-; SEQ ID NO: 81) by a ligase independent cloning technique. To produce the tri- and tetra-specific antibodies, the pair of "knob" and "hole" vector were co-transfected into HEK293A cells. Supernatant collected after 6-8 days was purified on protein A agarose, and the sc36TMB linkers were removed by thrombin treatment.

For producing the tri-specific antibody, the tandem Fab (Ipilimumab and Herceptin) with the "hole" Fc vector was paired the single-chain Daratumumab vector with "knob" Fc fragment (see, e.g., FIGS. 4A-4F). The resulting tri-specific antibody was termed Tri-N-Fab antibody. For the tetra-specific, the tandem Fab (Ipilimumab and Herceptin) with the "hole" Fc vector was paired the tandem Fab (Daratumumab and Atezolizumab) with "knob" Fc vector (see, e.g., FIGS. 5A-5G). The resulting tetra-specific antibody was termed Tetra-N-Fab antibody. Both Tri-N-Fabs and Tetra-N-Fabs molecules were submitted for ion-exchange chromatography for additional purification.

Alternatively, a HindIII restriction site located at the C-terminus of the antibody gene was used to introduce the C-linker (-GGGSGGGSGGGSG-; SEQ ID NO: 82) and an extra Fab domain to the "knob" or "hole" vector (see, e.g., FIGS. 6A-6J). To produce the Tri-C-Fabs molecule, the "hole" vector with two Fab modules (Ipilimumab at N-terminus and Herceptin at C-terminus) was co-expressed with the "knob" Fc vector for the single-chain Daratumumab Fab in HEK293A cells (see, e.g., FIG. 6A). To produce the Tetra-C-Fabs molecule, the above "hole" vector was co-expressed with the "knob" Fc vector with two Fab modules (Daratumumab at N-terminus and Atezolizumab at C-terminus) in HEK293A cells (see, e.g., FIG. 6B). Following purification by protein A agarose, the linkers were removed by thrombin treatment. Ion-exchange chromatography was applied to improve the purity.

Purification by Ion-Exchange Chromatography

The tri-specific and tetra-specific molecules were further purified by ion-exchange chromatography after the removal of intra-Fab linkers. In brief, the molecules were applied to a Mono S™ 5/50 GL column (GE Healthcare) on ÄKTA (GE Healthcare). The following buffers were used: mobile phase buffer A: 20 mM MES (2-morpholin-4-ylethanesulfonic acid), pH 6.0; and mobile phase buffer B: 20 mM MES, 1 M NaCl, pH 6.0. After loading and washing the samples with buffer A, gradient elution with 10% to 50% B were used for fractionation. Fractions were collected and analyzed by SDS-PAGE.

Ligand and Preparation and Biotinylation

Extracellular domain Fc fusions for human CTLA-4 (CTLA4-Fc) and ErbB2 (ErbB2-Fc) were purchased from Abcam (ab180054 and ab168896). These ligands were then biotinylated by the EZ-link® Sulfo-NHS-LC-Biotin according to the manufacturer's protocol (Thermo Scientific). Excessive biotin was removed by buffer-exchange into PBS, and biotinylated ligands were concentrated and stored at −80° C. The recombinant extracellular domain of CD38 and PD-L1 was produced as a 6-His and AviTag™ fusion in HEK293 cells and purified by Ni-NTA followed by in vitro biotinylation by BirA biotin ligase (Avidity).

ELISA and $EC_{50}$ Estimation

To accommodate the differences in valency between monoclonal and bi-, tri-, or tetra-specific antibodies, an ELISA assay was performed by immobilizing the antibody on a microtiter plate and testing binding to ligands in solution. The antibodies were diluted to 1 μg/ml in PBS and 100 μl of this diluted solution per well were applied to the Nunc MaxiSorp ELISA plate (Thermo Fisher) for coating overnight. The plate was washed three times with PBS, blocked with 4% BSA at RT for 1 hour, and incubated with corresponding biotinylated ligands at various concentrations at RT for 1 hour, each condition in triplicates. The plate was then washed five times with the washing buffer (0.05% Tween-20 in PBS), incubated with 0.1 μg/ml HRP-conjugated streptavidin (Pierce-Thermo Fisher) at RT for 30 minutes, washed 3 times with the washing buffer, and incubated with the peroxidase substrate solution (Sure-Blue®, Seracare) at RT for 3-5 min before the reaction was terminated by adding equal volume of 1 M HCl. The absorbance at 450 nm of each well was detected by a microtiter plate reader (Synergy BioTek® instrument). The absorbance value as a function of the ligand concentrations was analyzed to obtain the $EC_{50}$ value by curve fit (Prism, GraphPad).

Purity Assessment by Analytical Hydrophobic Interaction Chromatography

Purified antibodies were analyzed by HIC-HPLC with the infinity 1220 LC System (Agilent). Mobile phase A consisted of 25 mM phosphate and 1.5 M ammonium sulfate, pH 7.0. Mobile phase B consisted of 25% (v/v) isopropanol in 25 mM phosphate, pH 7.0. Antibody samples were loaded onto a TSK gel HIC column (Tosoh Bioscience) and operated at 0.5 m/min with a gradient from 10% to 100% B.

Absorbance was detected at 280 nm. Purity was estimated by area integration using OpenLab CDS software (Agilent).

Cell Binding Analysis by Flow Cytometry

Jurkat and MCF7 cell lines obtained from American Type Culture Collection (ATCC) were cultured in Dulbecco's Modified Eagle Medium (DMEM) with 10% fetal calf serum and 100 μg/ml penicillin-streptomycin in humidified atmosphere of 95% air and 5% $CO_2$ at 37° C. For flow cytometry analysis, approximately 50,000 cells were incubated with different monoclonal, bispecific or multispecific antibodies (the highest concentration of 200 nM with serial 4-fold dilutions) at RT for 1 hour, washed 3 times with PBS and further incubated with the secondary antibody solution (Alexa Fluor 647®-conjugated goat anti-human IgG, final concentration of 1 μg/ml) at RT for 1 hour, washed 3 times with PBS and analyzed by flow cytometry (Accuri™ C6, BD Biosciences). The median fluorescence intensity (MFI) values were analyzed by Prism (GraphPad) to obtain $EC_{50}$ values by curve fitting.

$K_d$ Determination by Bio-Layer Interferometry

A Gator instrument (Probe Life) was used to determine $K_d$ of antibody-ligand interactions by bio-layer interferometry. Biotinylated ligands were diluted to 5-10 μg/ml in the provided kinetics buffer (Probe Life) and immobilized onto streptavidin-coated biosensors. The sensors were sequentially incubated with antibodies (200 nM) and kinetics buffers for 180 seconds to assess rates of association and disassociation. $K_d$ values were analyzed by the Gator software (Probe Life).

Example 3

Monoclonal Antibodies Produced from Thrombin-Removable Single-Chain IgGs Show Similar Biochemical Features as Native IgGs This Example describes experiments performed to develop an efficient system for removing peptide linker to obtain a true IgG-like molecule. This is because single-chain IgGs using peptide linkers to join the light chain and heavy chain have been investigated previously for production and ligand binding.

In these experiments, several commercially available proteases were tested and determined that thrombin is a suitable enzyme because of its efficiency, accuracy, and compatibility with non-reducing environments. Two clinically established antibodies, Ipilimumab (Ipili) and Daratumumab (Dara), were selected as the study antibodies to generate scIgGs of Ipili and Dara with a linker positioned between the light chain and heavy chain. The linker, sc36TMB, is a flexible 36-residue peptide adapted from a previous study, with additional thrombin cleavage sites on both the N- and C-terminus (FIG. 7). As shown in Table 2 below, the engineered scIgG displayed similar yield as the original antibodies. In these experiments, antibodies were purified by protein A affinity capture from culture supernatant collected from cell culture dish (100 mm in diameter) 4 days following transient transfection of HEK293A cells.

TABLE 2

| General production | HEK293A/100 mm dish/4-day expression |
|---|---|
| Ipilimumab | 26 μg |
| Ipili- sc36TMB | 28 μg |
| Daratumumab | 32 μg |
| Dara-sc36TMB | 36 μg |

Figure 1C:
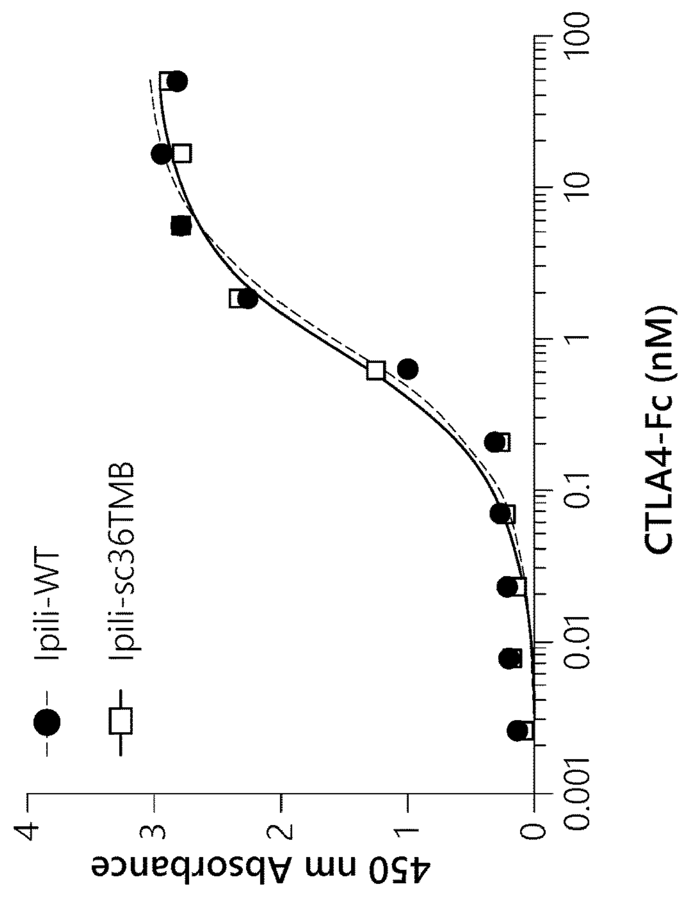
Figure 1D:
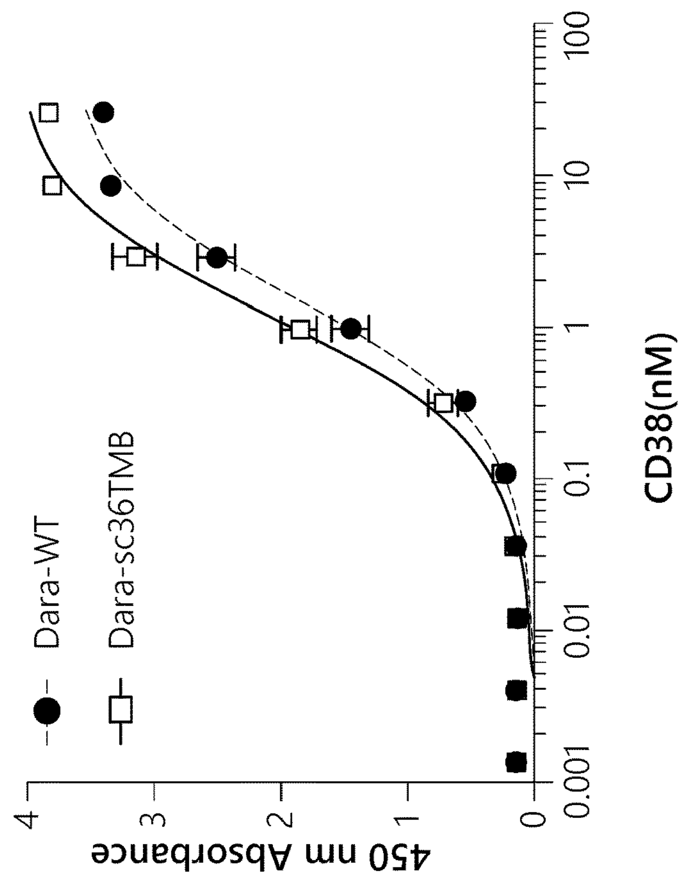

Furthermore, the linker was successfully removed by thrombin cleavage, yielding a ~150 kDa antibody product formed by disulfide-bonded light (~25 kDa) and heavy chains (~50 kDa), same as the natural antibody (Table 2). Following thrombin cleavage, a 5-mer peptide (-GLVPR, SEQ ID NO: 83) remained at the C-terminus of the light chain, as well as two residues (-GS) at the N-terminus of the heavy chain (see, e.g., FIG. 7). To evaluate if the processed IgG molecule possesses an intact paratope, the ligand binding was tested by ELISA (FIGS. 1C-1D). Ipilimumab was found to bind to the CTLA4-Fc with an $EC_{50}$ of approximately 0.99±0.13 nM, while the $EC_{50}$ of the cleaved Ipili-sc36TMB was estimated to be about 0.83±0.11 nM (FIG. 1C). Likewise, Daratumumab was found to bind its ligand, CD38, with $EC_{50}$ of approximately 1.56±0.11 nM, and the cleaved Dara-sc36TMB had an $EC_{50}$ of 1.24±0.09 nM (FIG. 1D). The similar $EC_{50}$ values between the processed scIgGs and the original antibodies indicate that the engineered linker and the cleavage process did not interfere with the formation of the antibody or the integrity of its paratope.

Example 4

Bispecific Antibodies Produced from Thrombin-Cleavable Single-Chain IgGs with the "Knobs-into-Holes" Fc Heterodimer This Example describe experiments performed to expand the study from monoclonal to bispecific antibody generation. The "knobs-into-holes" (KIH) design features critically paired mutations in the "knob" Fc (T366W) and "hole" Fc (T366S/L368A/Y407V), which enforces pairing of the KIH Fc heterodimer. However, this KIH design does not enforce proper light chain pairing.

Figure 2A:
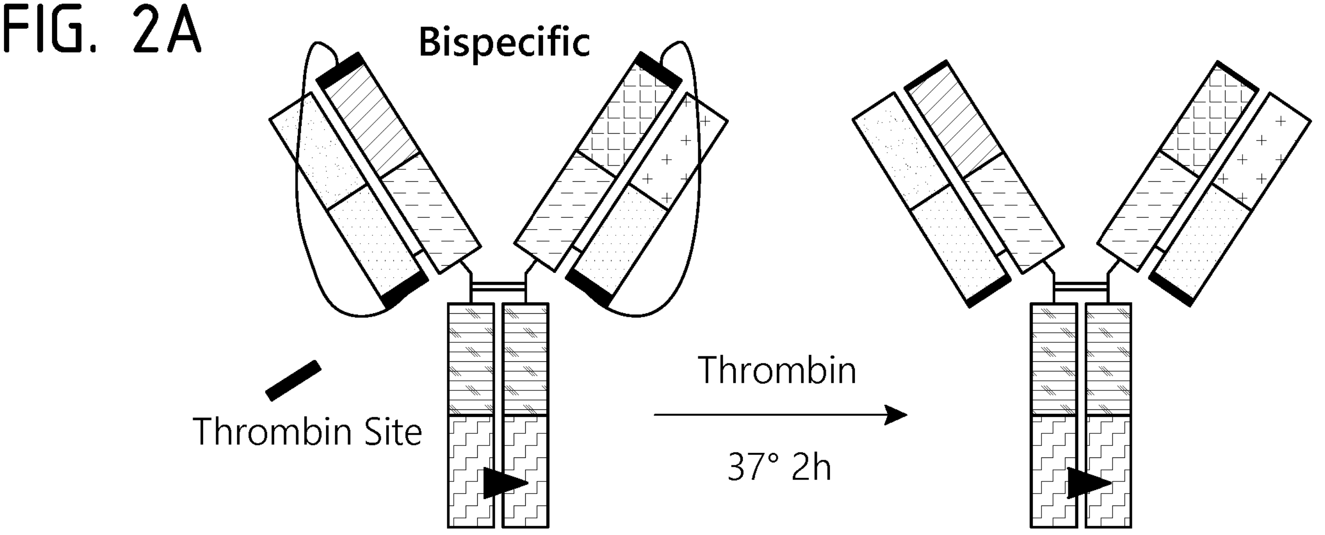
FIGS. 2A-2L graphically summarize the results of experiments performed to illustrate the production of bispecific antibodies with thrombin-cleavable linkers and "knobs-into-holes" (KIH) Fc domains.

The successful production and thrombin-cleavage of the scIgGs to IgG molecules provides a plausible solution for enforcing correct pairing between light and heavy chains. The experiments described herein were performed to generate bispecific antibodies using the KIH Fc system in conjunction with a thrombin-removable linker. Two sets of antibodies, Ipilimumab pairing with Daratumumab, and Ipilimumab pairing with Herceptin, were selected as the test samples. The scheme to produce bispecific antibodies is shown in FIG. 2A. In brief, the light chain of each antibody is fused with the corresponding heavy chain via a thrombin-removable linker. The Fc region used for Ipilimumab was the "hole" Fc region, while the Fc for either Daratumumab or Herceptin was the "knob" Fc region. Bispecific antibodies were produced by co-transfecting HEK293A cells with the "knob" and "hole" scIgG constructs at a 1:1 ratio, and purified from culture supernatant by protein A agarose, and processed by thrombin to remove the linker.

Figure 2B:
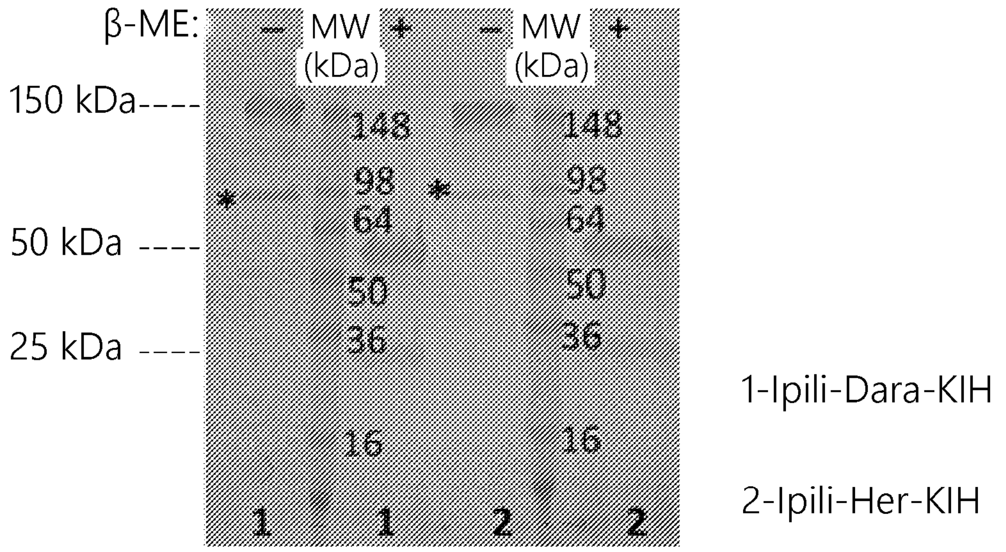
Figure 2D:
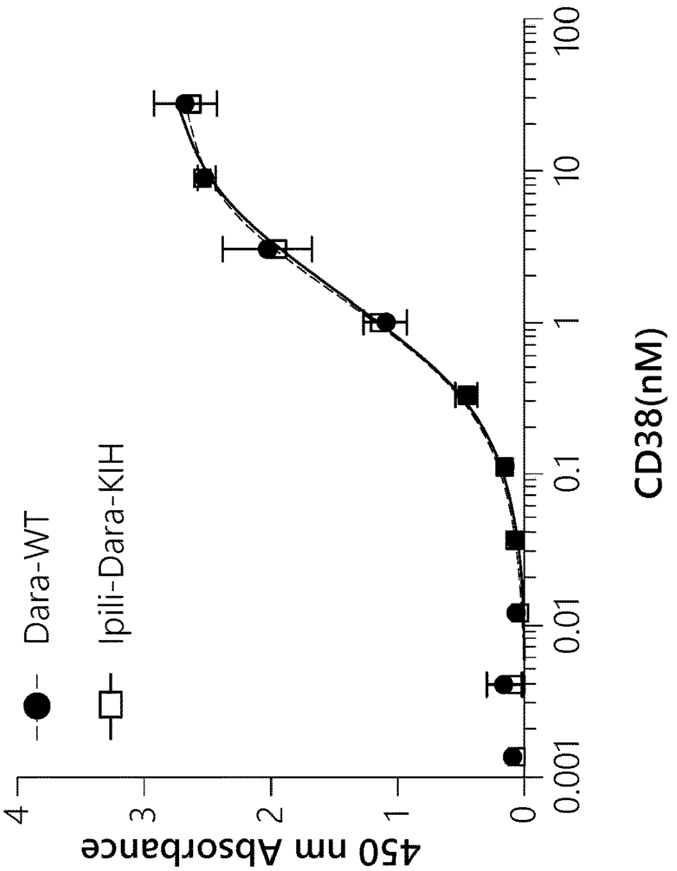
Figure 2C:
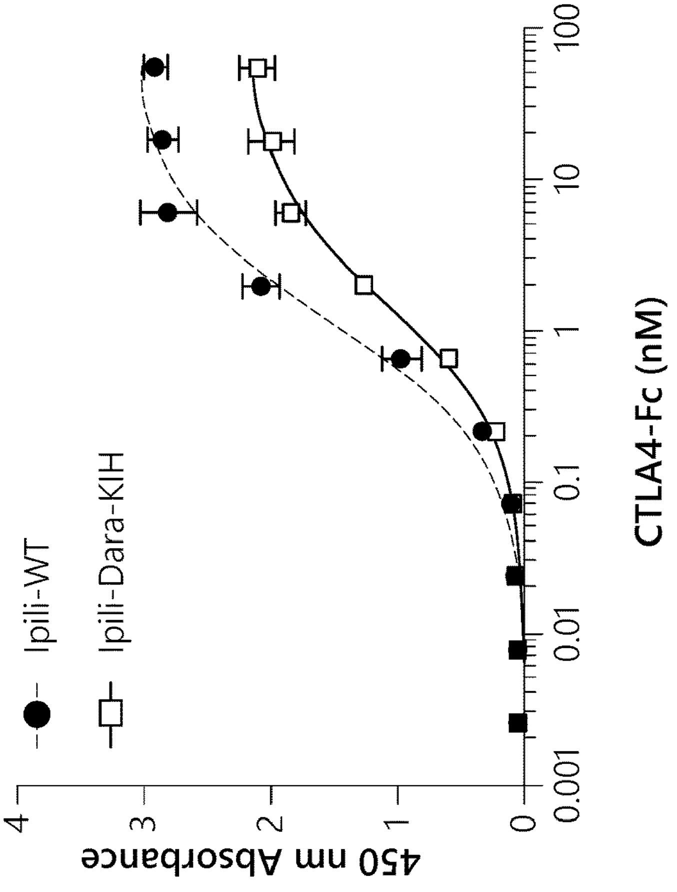
Figure 2F:
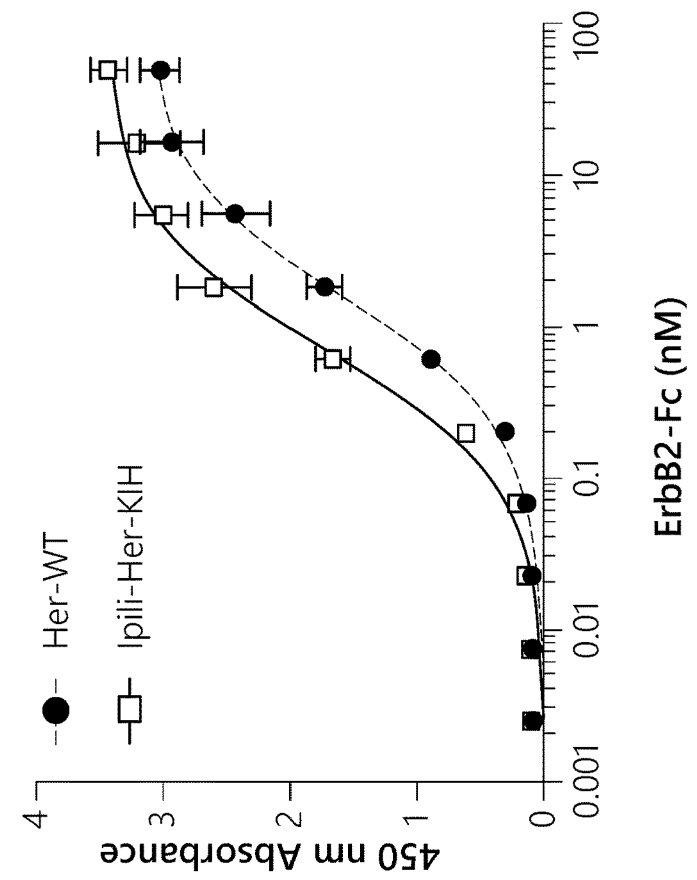
Figure 2E:
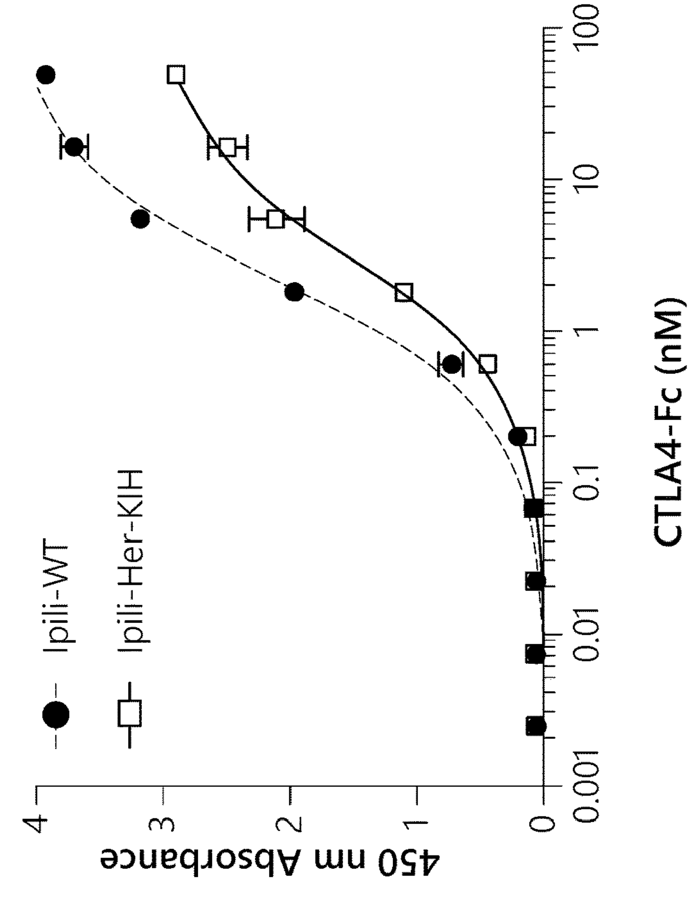
Figure 2G:
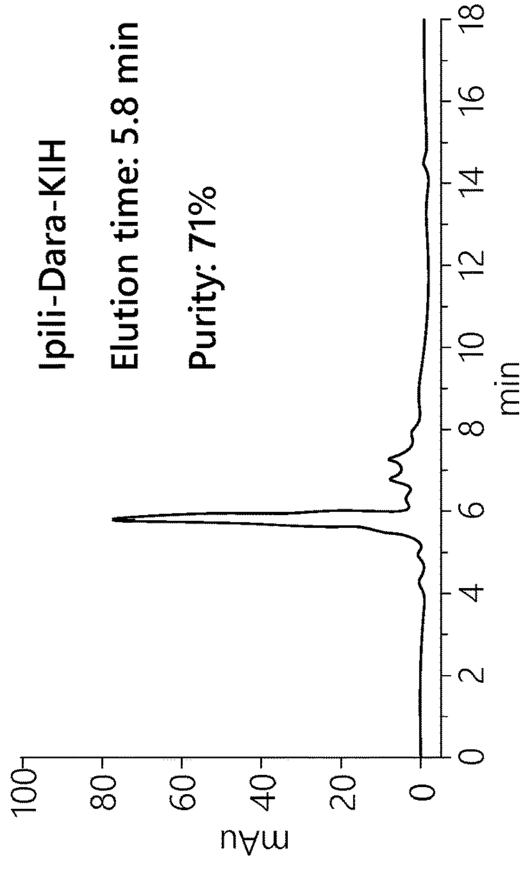
Figure 2H:
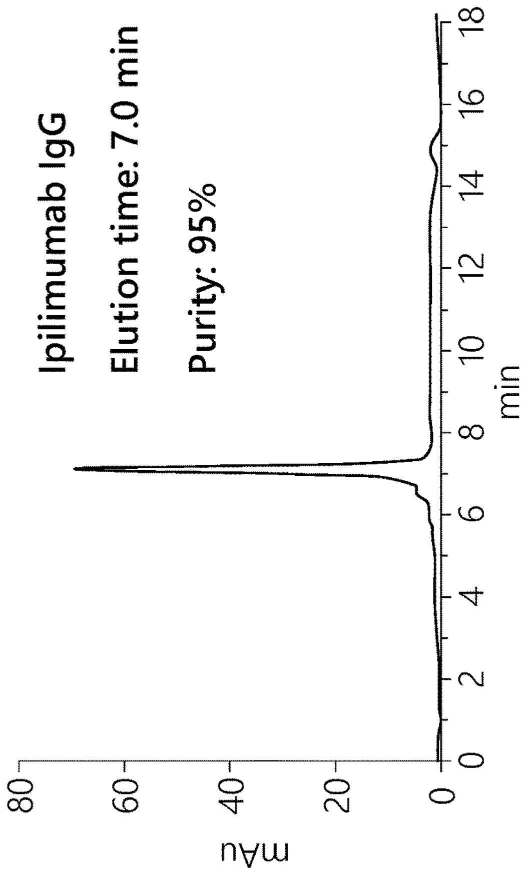
Figure 2J:
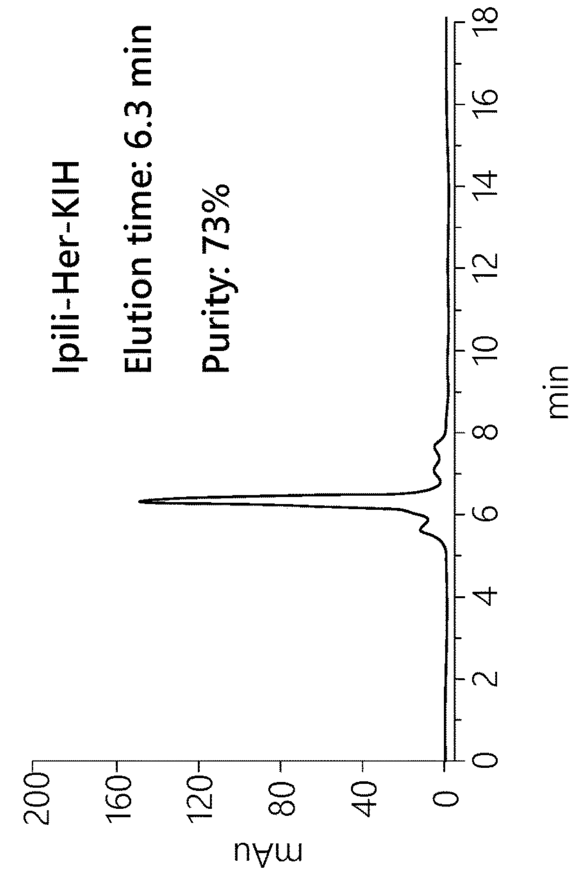
Figure 2I:
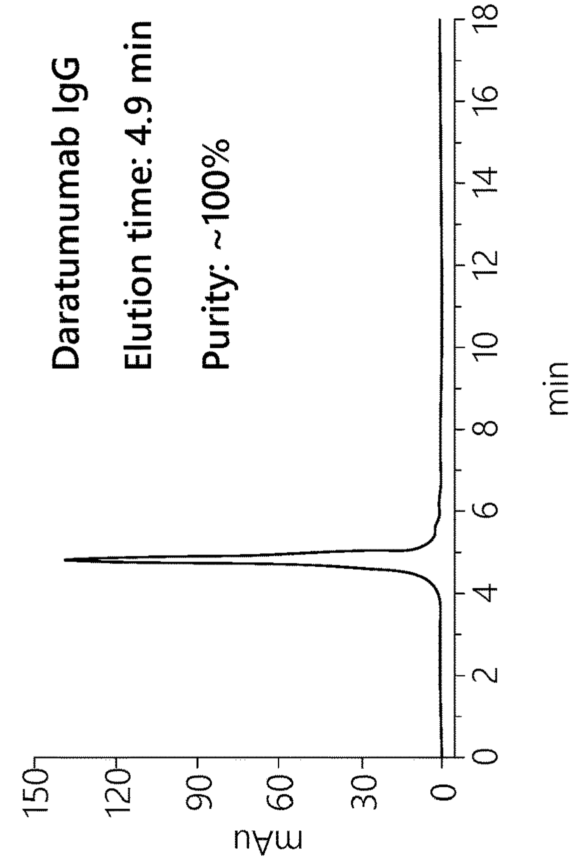
Figure 2K:
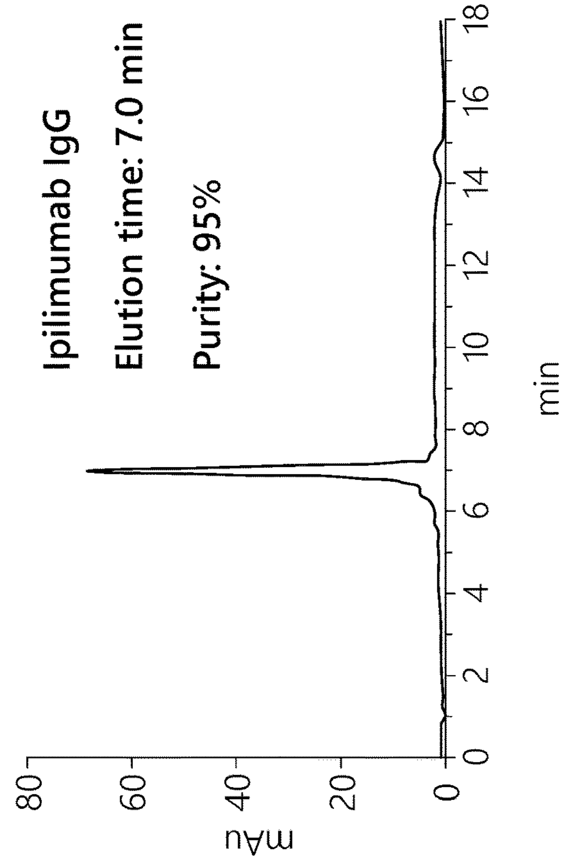
Figure 2L:
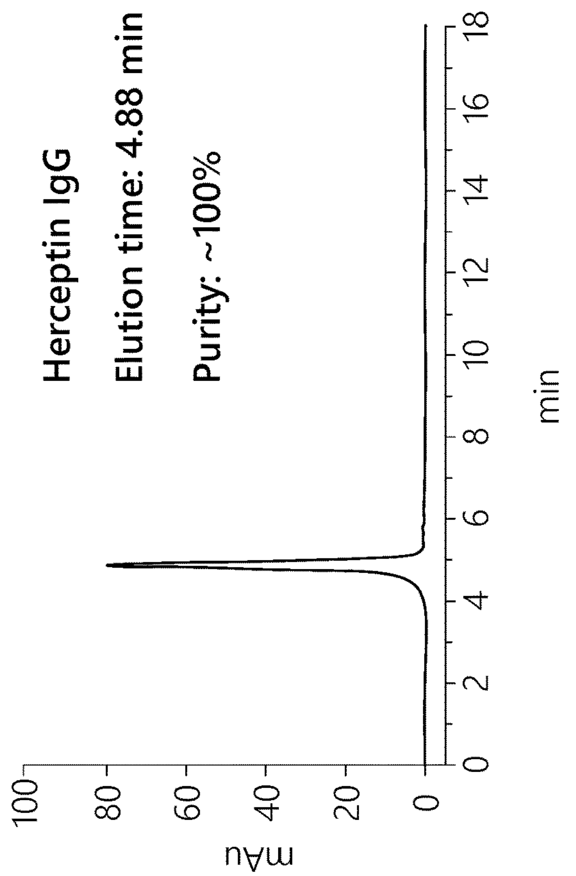

Using this system, experiments described herein have illustrated that it was obtain relatively pure IgG-like molecules for both bispecific antibodies with estimated molecular weights of ~150 kDa under non-reducing condition. As shown in FIG. 2B, the KIH product could be separated into light chain (~25 kDa) and heavy chain (~50 kDa) by reduction with 3-mercaptoethanol (β-ME). The purity of the KIH product was assessed using analytical hydrophobic interaction chromatography (HIC). Both Ipili-Dara-KIH and Ipili-Her-KIH antibodies displayed a dominant bispecific component, comprising 71% and 73% of the total product, respectively. FIGS. 2G-2L summarize the results of a purity assessment of the bi-specific antibodies Ipili-Dara-KIH and Ipili-Her-KIH by analytical hydrophobic interaction chromatography. The main peak of Ipili_Dara_KIH (FIG. 2G)

shows an elution time in-between of Ipilimumab (FIG. 211) and Daratumumab (FIG. 2I), representing the desired bispecific product that is estimated by area integration (OpenLab CDS, Agilent) to be 71% of total protein obtained from one-step protein A purification. For the Ipili-Her-KIH antibody, the main peak of Ipili_Her_KIH (FIG. 2J) shows an elution time in-between of Ipilimumab (FIG. 2K) and Herceptin (FIG. 2L), representing the desired bispecific product that is estimated to be 73% of total protein obtained from one-step protein A purification. The integrity of the paratopes of each Fab in the bispecific antibody was also investigated by ELISA. Unlike an IgG molecule that binds bivalently to one ligand, the binding of the IgG-like bispecific antibody to each of its two ligands is monovalent. To minimize the influence of valency in the ELISA assay, the antibodies were mobilized on plates and the binding to ligands was assessed in solution. As shown in FIGS. 2C-2D, and Table 3 below, the Ipili-Dara-KIH was capable of binding to both CTLA4 and CD38, in manners similar to the parental monoclonal antibodies (Ipilimumab and Daratumumab), indicating that the bispecific antibodies possessed intact paratopes. Similar results were observed for the bispecific Ipili-Her-KIH (FIGS. 2E-2F, and Table 4).

TABLE 3

| Estimated $EC_{50}$ | | |
|---|---|---|
| Ipilimumab | $EC_{50}$ to CTLA4-Fc | $EC_{50}$ to CD38 |
| Ipilimumab | 1.10 ± 0.10 nM | — |
| Ipili-Dara-KIH | 1.43 ± 0.11 nM | 1.44 ± 0.08 nM |
| Daratumumab | — | 1.48 ± 0.18 nM |

TABLE 4

| Estimated $EC_{50}$ | | |
|---|---|---|
| Ipilimumab | $EC_{50}$ to CTLA4-Fc | $EC_{50}$ to CD38 |
| Ipilimumab | 2.21 ± 0.13 nM | — |
| Ipili-Her-KIH | 3.11 ± 0.24 nM | 0.72 ± 0.06 nM |
| Herceptin | — | 1.58 ± 0.12 nM |

Example 5

Use of Linker-Embedded Affinity Tags for Further Purification of Bispecific Antibodies This Example describes the use of linker-embedded affinity tags for further purification of bispecific antibodies described above. Contamination in bispecific antibodies produced by the KIH approach has been observed previously, which primarily arises from "hole-hole" or "knob-knob" homodimers. Common procedures for antibody purification, such as protein A or G affinity chromatography, reply on recognition of the Fc domain and thus cannot effectively distinguish the bispecific KIH heterodimer from contaminating homodimers. Prior approaches to enhance the efficiency of correct pairing of the KIH heterodimer or eliminate the non-bispecific contamination often involve introducing additional mutations and additional steps in purification.

Figure 3A:
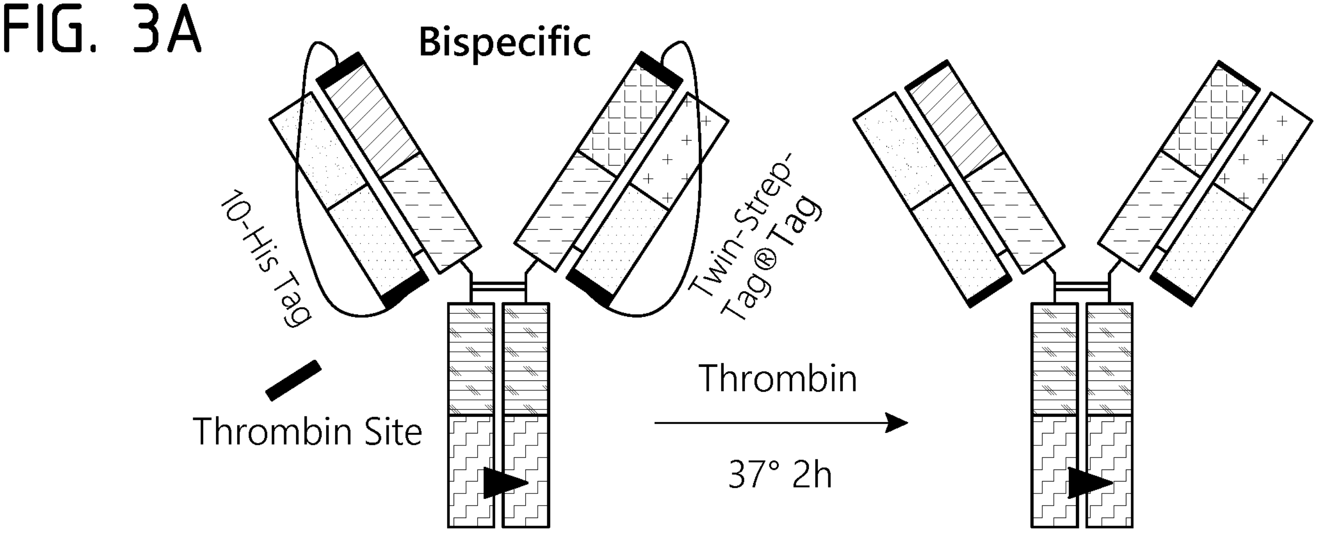
FIGS. 3A-3E graphically summarize the results of experiments performed to illustrate the production of bispecific antibody with high purity using a pair of thrombin-cleavable dual-tagged affinity linkers.
Figure 3B:
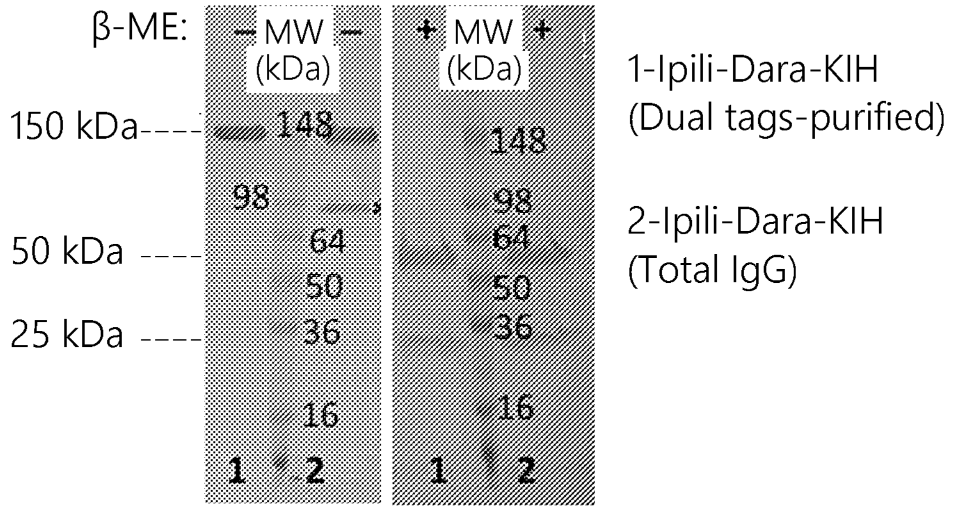
Figure 3C:
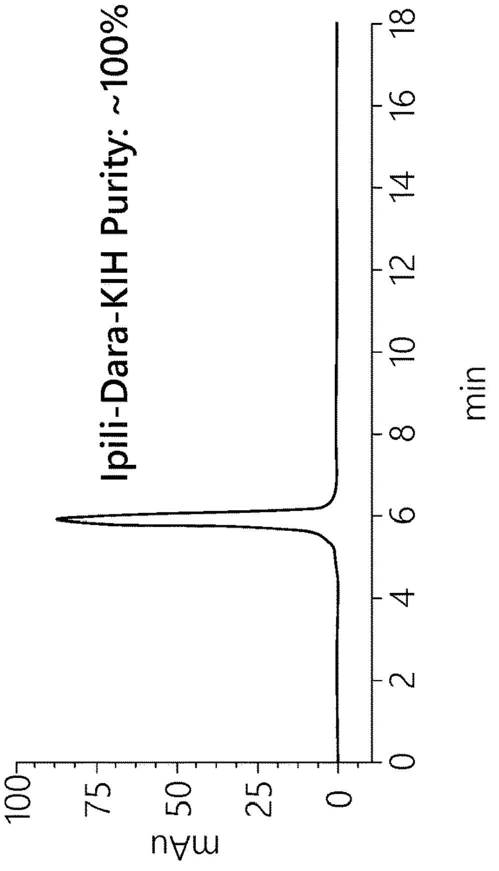
Figure 3D:
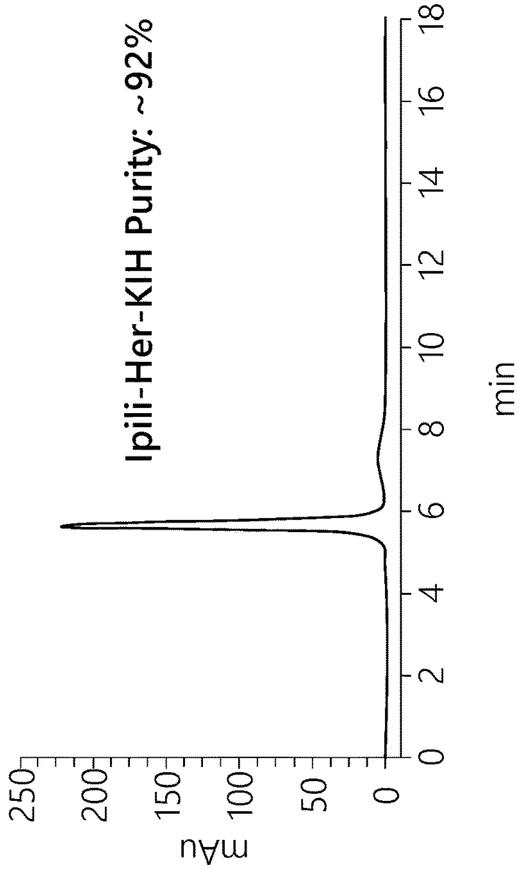

Some experiments described herein took advantage of the removable nature of the linker and embedded a pair of affinity tags, the 10-His tag and Twin-Strep-Tag®, into the linkers to enable the purification of the bispecific product (see, e.g., FIG. 3A and SEQ ID NOS: 6-7). The KIH heterodimer would possess both affinity tags and thus be readily distinguished from homodimers. Two following plasmids have been constructed: the first plasmid expressing Ipilimumab with a Twin-Strep-Tag® linker and the "hole" Fc mutant region, and the second plasmid expressing Daratumumab or Herceptin with a 10-His tag linker and the "knob" Fc mutant region. The resulting plasmids were co-transfected HEK293A cells to generate bispecific antibodies, i.e., Ipili-Dara-KIH and Ipili-Her-KIH. The supernatant was sequentially purified using Ni-NTA and Strep-Tactin® XT resin to obtain antibody products with both tags and thus both specificities. The linkers were removed by thrombin cleavage to generate the final product. As shown in FIG. 3B, SDS-PAGE results showed that bispecific antibodies produced in this manner contained substantially lower amounts of containments (labeled with *). In addition, HIC-HPLC analysis showed that the purities of the Ipili-Dara-KIH and Ipili-Her-KIH were nearly 100% and about 92%, respectively (FIGS. 3C-3D).

Figure 3E:
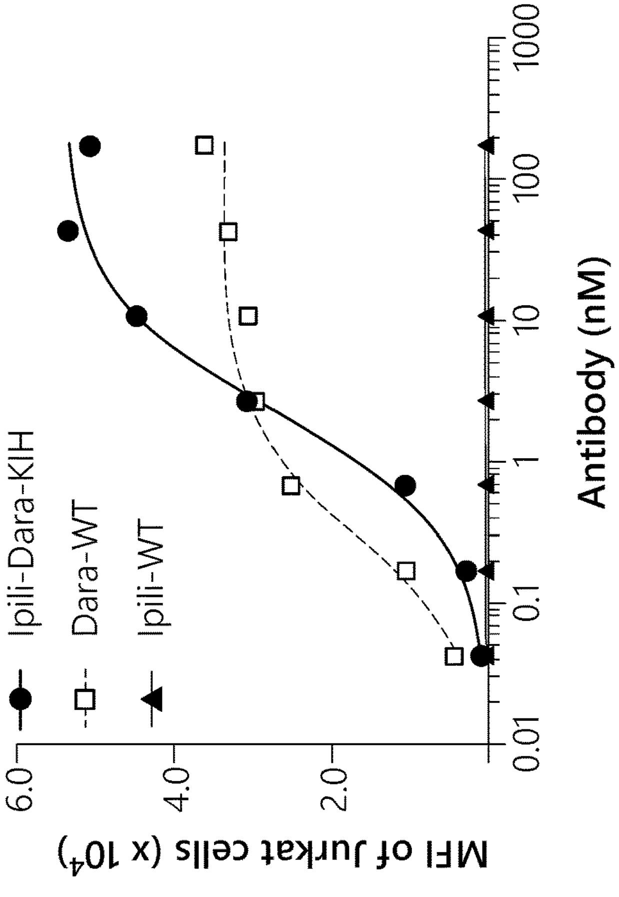
Figure 3F:
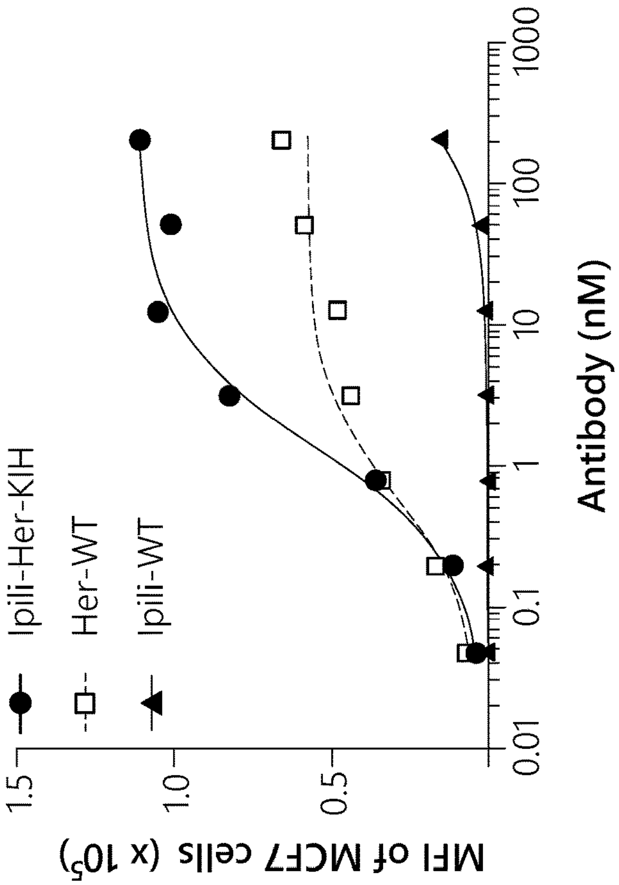
FIG. 3F shows flow cytometry analysis of MCF7-cell binding by each of the antibodies Ipili-Her-KIH, Herceptin, and Ipilimumab at various concentrations (0-200 nM).

Subsequent experiments were performed to investigate how bispecific antibodies recognized cells expressing target antigens. The Jurkat cell line has been previously used to study CD38 binding. In the experiments described herein, it was found that indeed Jurkat cells express CD38 were bound by Daratumumab (FIG. 3E). However, little to no expression of CTLA4 was detected by Ipilimumab (FIG. 3E). Thus Jurkat cells are useful mainly for assessing the CD38 binding arm. As shown in Table 5 below, the bispecific antibody, Ipili-Dara-KIH, which is monovalent in each specificity, was found to bind to Jurkat cells with $EC_{50}$ of 2.26±0.26 nM. Daratumumab, a bivalent IgG, bound to Jurkat cells with $EC_{50}$ of 0.31±0.05 nM. The bispecific Ipili-Dara-KIH bound to Jurkat cells with a higher median fluorescence intensity (MFI) value compared with Daratumumab, consistent with its monovalent binding mode.

TABLE 5

Binding to CD38 and ErbB2 was tested on Jurkat cells and MCF7 cells, respectively. The apparent Kd values were obtained by curve fitting MFI values (Prism, GraphPad). Apparent $K_d$ for antigen binding to antigen-expressing cells

| Antibody | EC50 to Jurkat cells | EC50 to MCF7 cells |
|---|---|---|
| Daratumumab | 0.31 ± 0.14 nM | — |
| Ipilimumab | — | weak |
| Ipili-Dara-KIH | 2.26 ± 0.26 nM | — |
| Herceptin | — | 0.60 ± 0.18 nM |
| Ipili-Her-KIH | — | 1.39 ± 0.21 nM |

Similarly, additional experiments were performed to investigate how the bispecific Ipili-Her-KIH antibody binds to the breast cancer cell line MCF7 that has been reported to express both ErbB2 (Her2) and CTLA4. It was observed that a high staining signal by flow cytometry on MCF7 by Herceptin, but a rather low signal by Ipilimumab. Thus, MCF7 cells were used to evaluate the Her2-binding arm only. The bispecific Ipili-Her-KIH binds to MCF7 (FIG. 3F) with $EC_{50}$ of 1.39±0.21 nM (Table 5). Herceptin, a bivalent IgG, binds to MCF7 (FIG. 3F) with $EC_{50}$ of 0.60±0.18 nM (Table 5). The total MFI for the bispecific Ipili-Her-KIH is higher than Herceptin, consistent with its monovalent binding mode.

To evaluate binding of bispecific antibodies to CTLA4 on cell surface, HEK293A cells were transiently transfected with a construct expressing the human CTLA4 gene. After culturing for 18 hours, the cells were harvest and analyzed by flow cytometry for binding by Ipilimumab IgG, Ipilimumab Fab, Ipili-Dara-KIH, and Ipili-Her-KIH. Like Ipilimumab, it was observed that both bispecific antibodies were able to bind to the CTLA4-transfected cells (data not shown), confirming that the anti-CTLA-4 arm is functional. As shown in Table 6 below, the apparent binding affinities of the bispecific antibodies were lower than that of the bivalent Ipilimumab IgG, an expected result given the valency difference, but higher than the Ipilimumab Fab that is also monovalent. MFI values at saturation binding were higher for the bispecific (and the Ipilimumab Fab) than the Ipilimumab IgG, again consistent with the monovalent vs. bivalent binding mode.

TABLE 6

The apparent Kd values were obtained by curve fitting MFI values (Prism, GraphPad). Apparent $K_d$ for binding to CTLA4-expressing HEK293A cells

| | |
|---|---|
| Ipilimumab IgG | 9.23 ± 3.48 nM |
| Ipilimumab Fab | 101.30 ± 20.16 nM |
| Ipili-Dara-KIH | 47.10 ± 3.77 nM |
| Ipili-Her-KIH | 33.55 ± 3.06 nM |

Example 6

Facile Generation of Multispecific Antibodies Using Thrombin-Removable Linkers This Example describes experiments performed taking advantage of the modular nature of the linker-enforced chain assembly to generate multispecific antibodies using the enzymatically cleavable linker. The generation and application of antibodies with even higher order of specificity and complexity are challenging tasks that have only been attempted a limited number of times. In general, as the complexity of the molecule grows, the difficulty grows disproportionally or exponentially in proper assembly of six, eight, or more chains into one antibody. As described in greater detail below, multispecific antibodies were designed based on the IgG-like bispecific with additional specificities introduced by appending Fab domains to either the N-terminus (FIGS. 4-5, tandem Fabs) or C-terminus (FIG. 6) of the bispecific molecule.

Figure 4A:
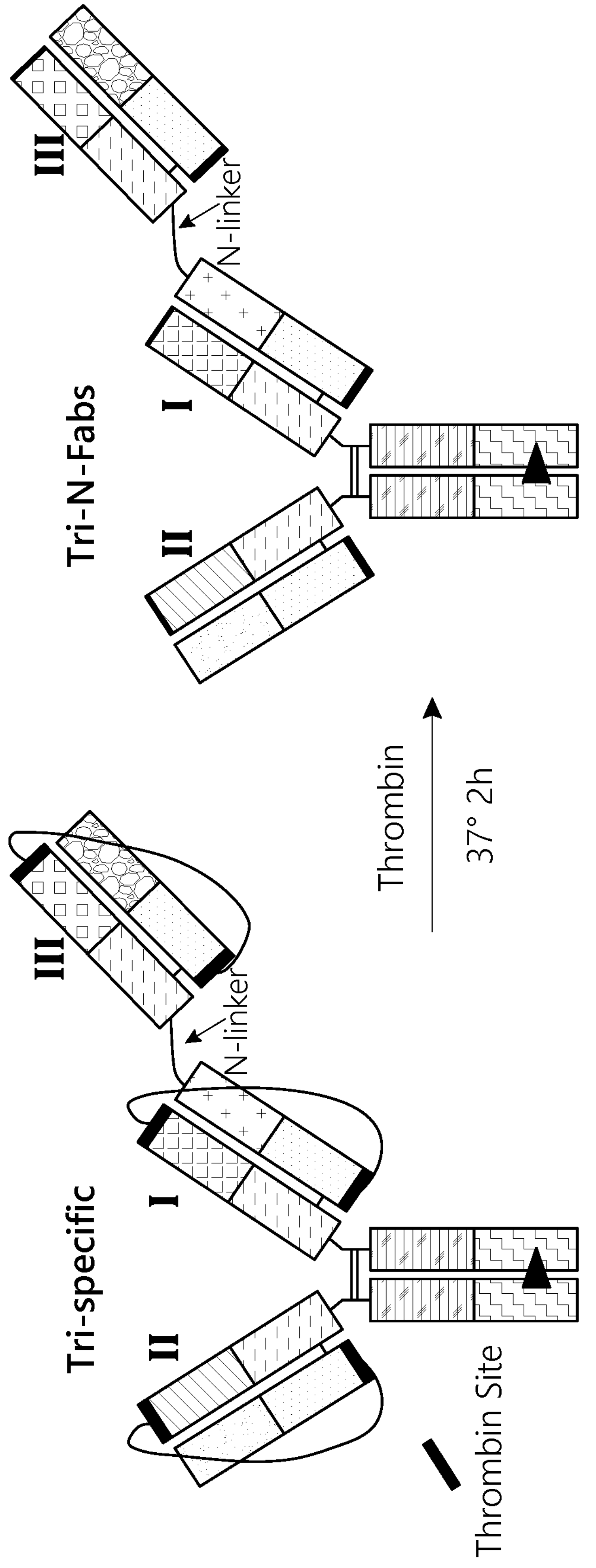
FIGS. 4A-4E graphically summarize the results of experiments illustrating the design of Tri-N-Fabs as a new format for tri-specific antibodies produced with thrombin-removable linkers and KIH Fe heterodimers. An exemplary production scheme and final structure of the Tri-N-Fabs is presented in FIG. 4A. The extra Fab domain (III) is appended to the N-terminus of the bispecific antibody. For the Tri-N-Fabs produced, Fabs of Ipilimumab were placed at position I, Daratumumab at position II, and Herceptin at position III.

In the case of tandem Fab constructs shown in FIG. 4 (tri-specific) and FIG. 5 (tetra-specific), the four different chains (two heavy and two light chains) of two antibodies (I, III) were genetically fused into one polypeptide in the following configuration:

Light chain-sc36TMB linker-heavy chain-N-linker-light chain (I)-sc36TMB linker-heavy chain (I) and "hole" Fc mutant region (as illustrated in FIG. 4A, SEQ ID NO: 9).

Figure 5A:
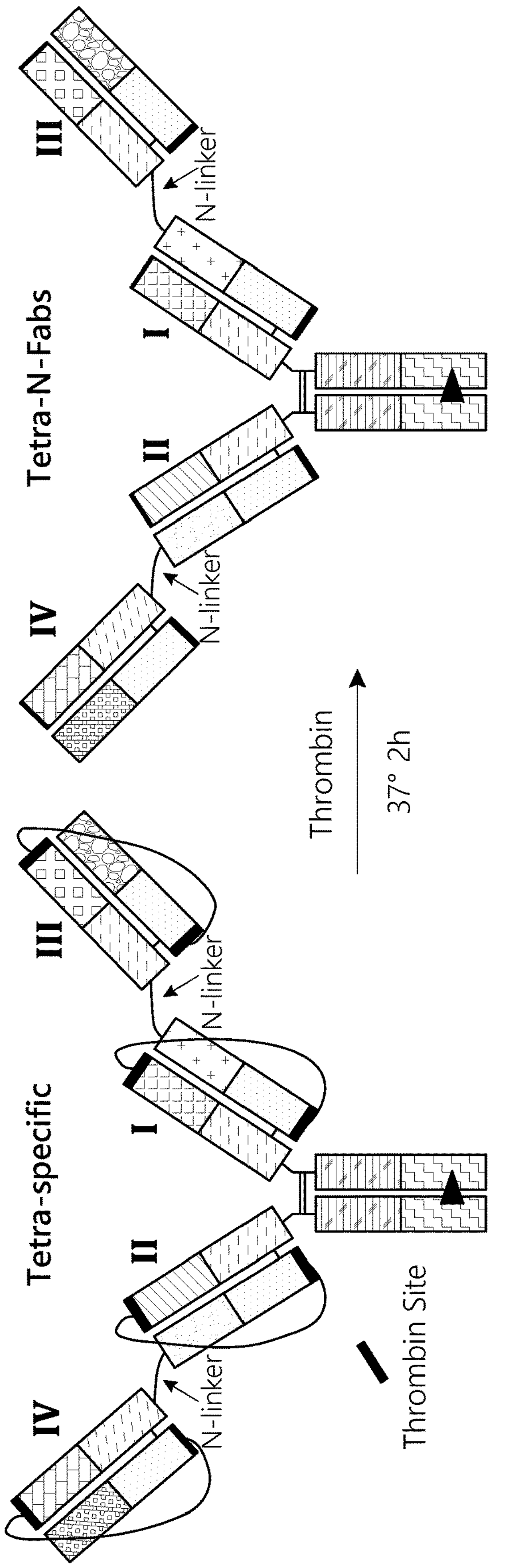
FIGS. 5A-5G graphically summarize the results of experiments performed to illustrate the production of tetra-N-Fabs, a new format for tetra-specific antibodies, with thrombin-removable linkers and KIH Fc heterodimers.

This tandem Fab construct was paired with an antibody construct (position II) with the "knob" Fc mutant to produce the tri-specific antibodies (FIG. 4A, SEQ ID NO: 4 and 9). To produce a tetra-specific molecule, two other antibodies (II, IV) were constructed in a second tandem Fab construct with the "knob" mutant in a configuration similar to that of the "hole" Fc mutant (FIG. 5A, and SEQ ID NO: 9-10).

Co-expression of resulting constructs produced the precursors for either tri-specific (FIG. 4A, SEQ ID NO: 4 and 9) or tetra-specific (FIG. 5A, and SEQ ID NO: 9-10) molecules, which were then processed by thrombin cleavage to remove the linker scaffold within each Fab unit. In this way, the following antibodies were generated: the asymmetric tri-specific antibody (Tri-N-Fabs) and the symmetric tetra-specific antibody (Tetra-N-Fabs), with Ipilimumab in position I, Daratumumab in position II, Herceptin in position III, and Atezolizumab in position IV (in the case of Tetra-N-Fabs).

Figure 4B:
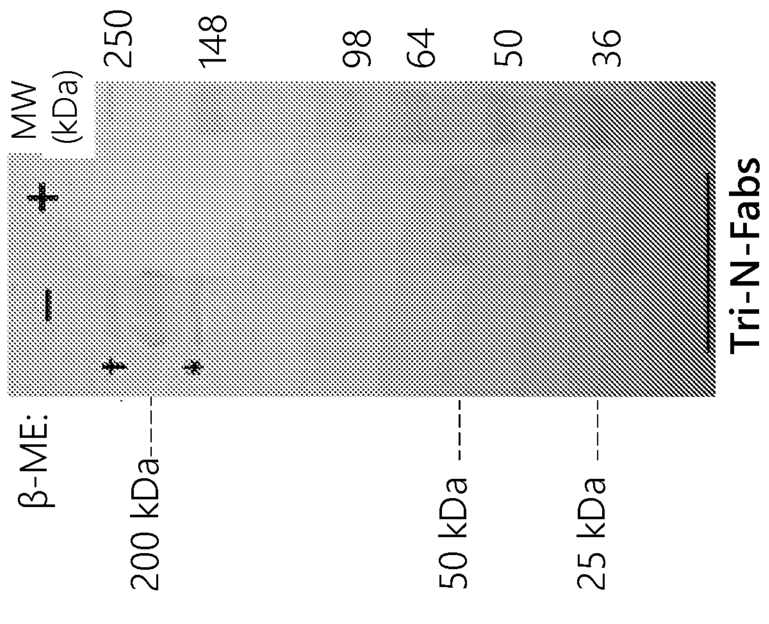
Figure 4C:
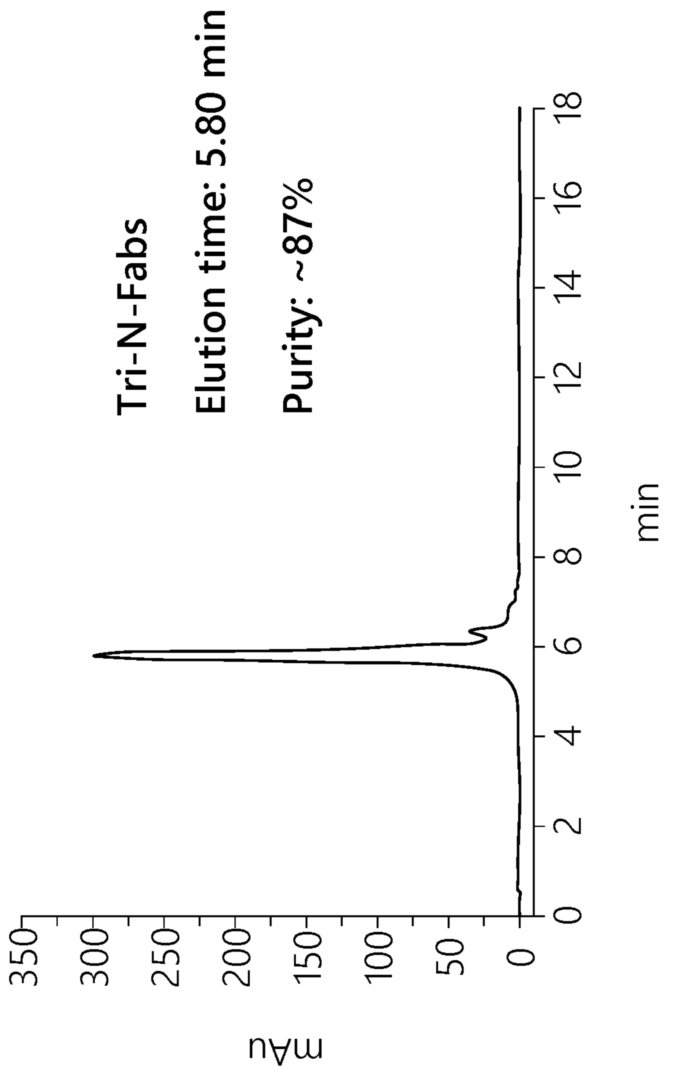
Figure 4D:
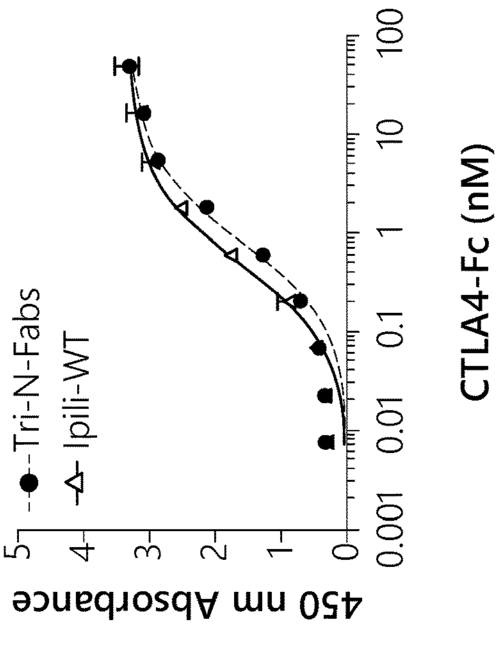
Figure 4E:
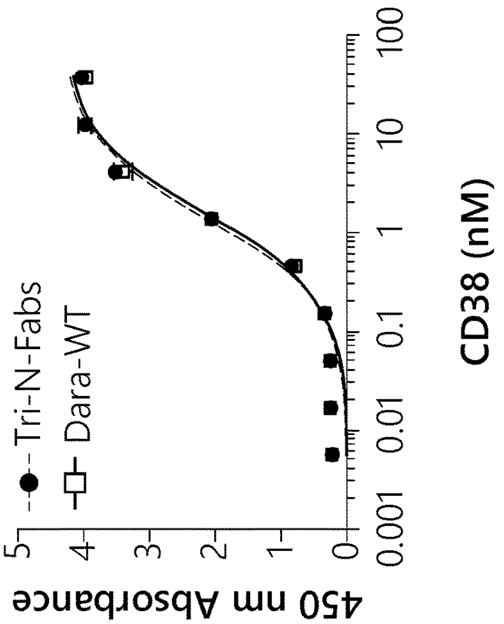
Figure 4F:
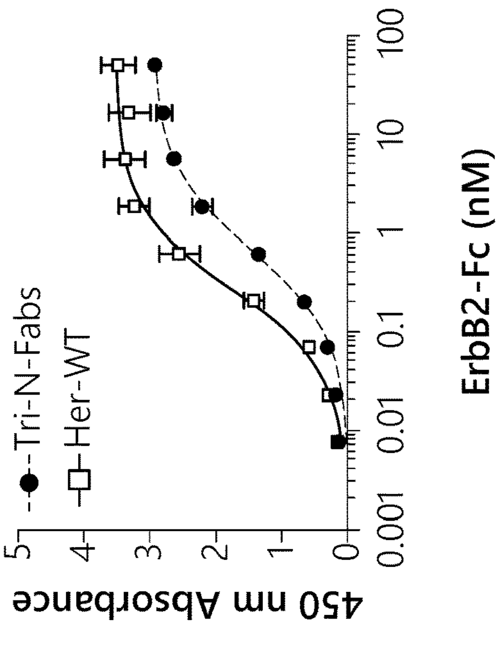
Figure 5B:
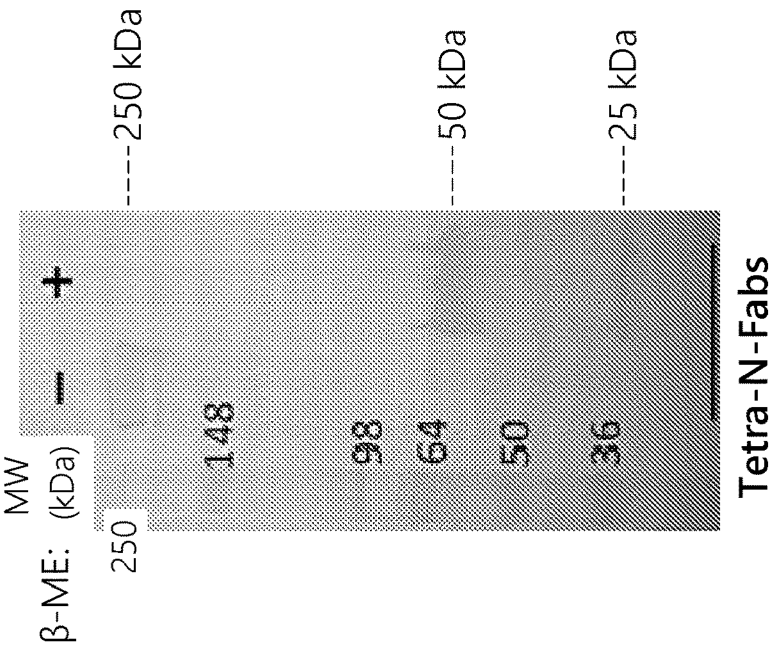
Figure 5C:
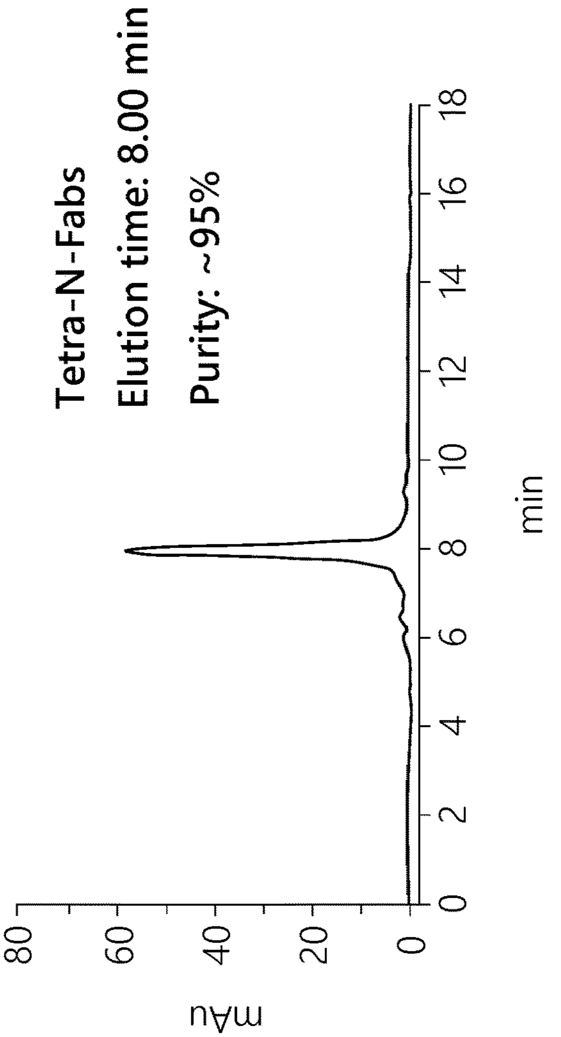
Figure 5E:
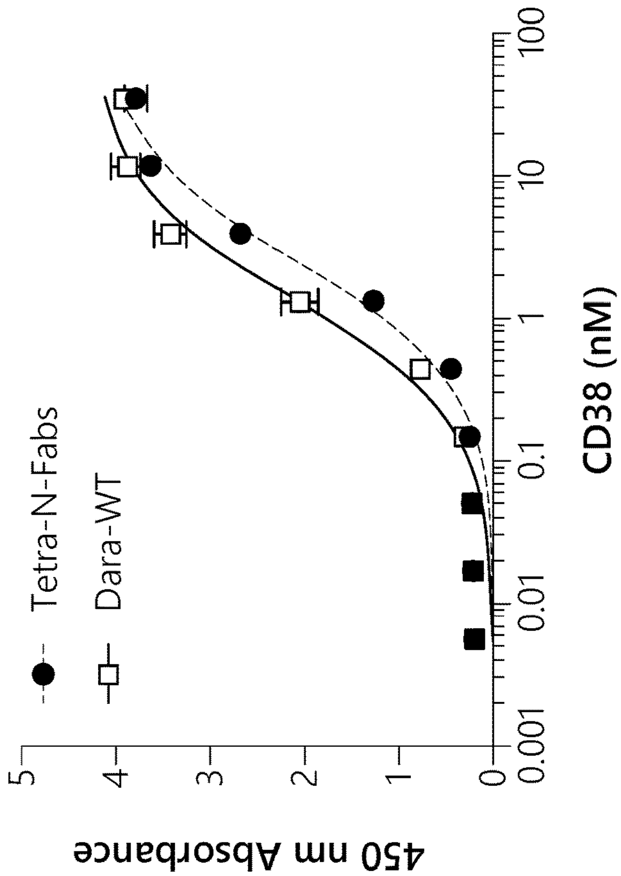
Figure 5D:
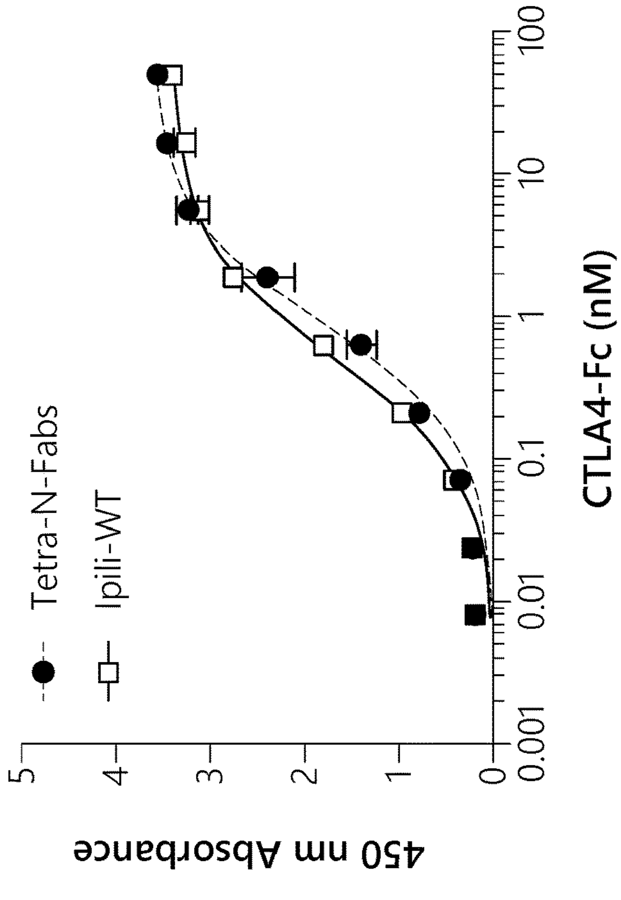
Figure 5G:
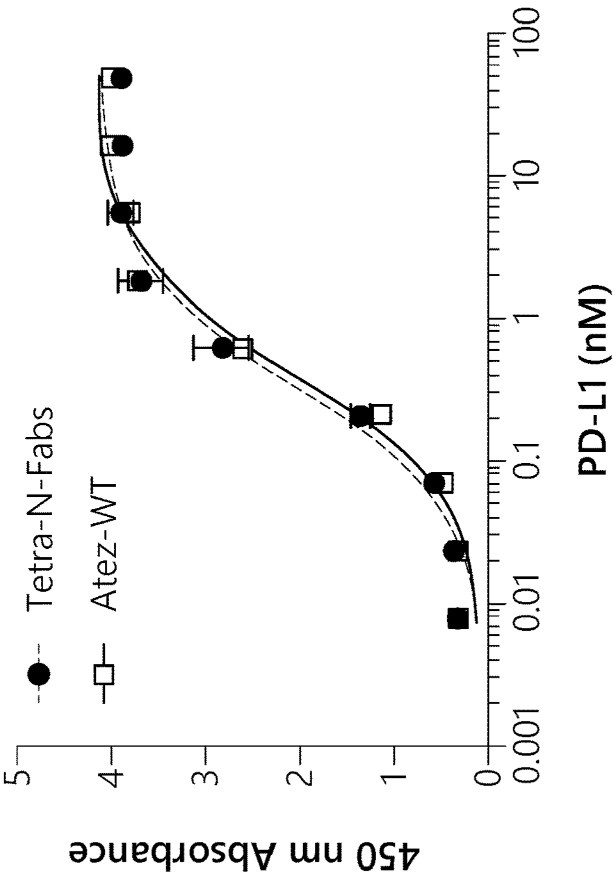
Figure 5F:
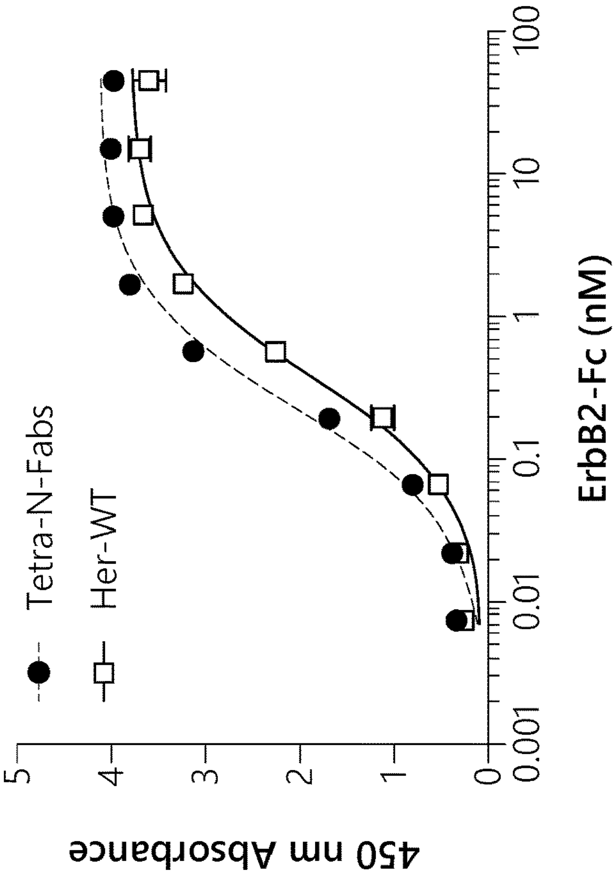

By SDS-PAGE analysis, it was found that purified Tri-N-Fabs and Tetra-N-Fabs displayed correct molecular weights, estimated to be 200 kDa and 250 kDa respectively, under non-reducing conditions and were separated into polypeptides with molecular weights of approximately 50 kDa and 25 kDa under reducing conditions (FIGS. 4B, 5B). Purity of the final products was assessed by analytical HIC-HPLC and found to be approximately 87% for Tri-N-Fabs (FIG. 4C) and 95% for Tetra-N-Fabs (FIG. 5C). Antigen binding was evaluated by ELISA, where the antibody was immobilized on plate, and tested for binding to biotinylated ligands in solution (CTLA4-Fc, CD38, ErbB2-Fc, and PD-L1). Both the Tri-N-Fabs and the Tetra-N-Fabs showed binding to all corresponding ligands with apparent affinity similar to that of the parental antibodies (see, FIGS. 4D-4F and Table 7 for Tri-N-Fabs; FIGS. 5D-5G and Table 8 for Tetra-N-Fabs). In these experiments, estimated EC50 values of ligand binding by Tri-N-Fabs along with the parental antibodies were analyzed by ELISA. $OD_{450}$ values were curve-fit (Prism, GraphPad) to obtain $EC_{50}$ values. These results indicate that the Tri-N-Fabs and the Tetra-N-Fabs possess the designed paratopes that are functional.

TABLE 7

Assessment of ligand binding of tri-specific Tri-N-Fabs antibodies. Estimated $EC_{50}$

| Antibody | CTLA4-Fc | CD38 | ErbB2-Fc |
|---|---|---|---|
| Tri-N-Fabs | 0.85 ± 0.11 nM | 1.45 ± 0.13 nM | 0.67 ± 0.05 nM |
| Ipilimumab | 0.50 ± 0.06 nM | — | — |
| Daratumumab | — | 1.49 ± 0.13 nM | — |
| Herceptin | — | — | 0.27 ± 0.07 nM |

TABLE 8

Assessment of ligand binding of tetra-specific Tetra-N-Fabs antibodies. Estimated $EC_{50}$

| Antibody | CTLA4-Fc | CD38 | ErbB2-Fc | PD-L1 |
|---|---|---|---|---|
| Tetra-N-Fabs | 0.86 ± 0.07 nM | 2.71 ± 0.26 nM | 0.25 ± 0.02 nM | 0.33 ± 0.03 nM |
| Ipilimumab | 0.49 ± 0.03 nM | — | — | — |
| Daratumumab | — | 1.47 ± 0.14 nM | — | — |
| Herceptin | — | — | 0.41 ± 0.03 nM | 0.40 ± 0.04 nM |

Figure 6A:
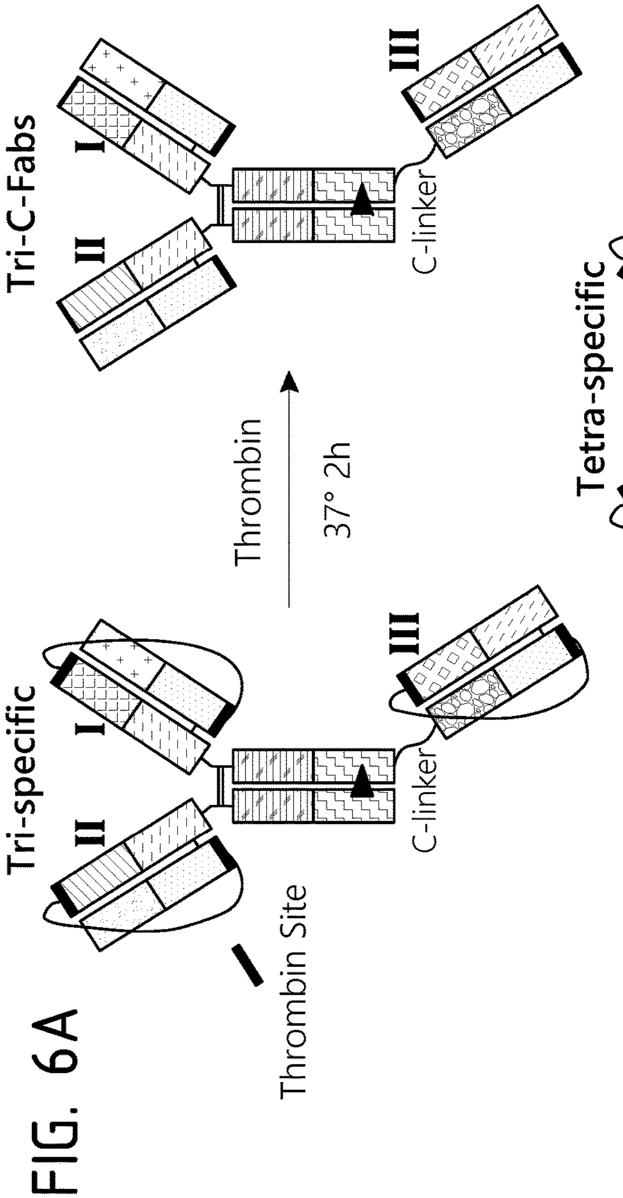
FIGS. 6A-6L graphically summarize the results of experiments performed to illustrate the production of Tri-C-Fabs and Tetra-C-Fabs as alternative formats for tri- and tetra-specific antibodies using the thrombin-removable linker and KIH Fc heterodimer.
Figure 6B:
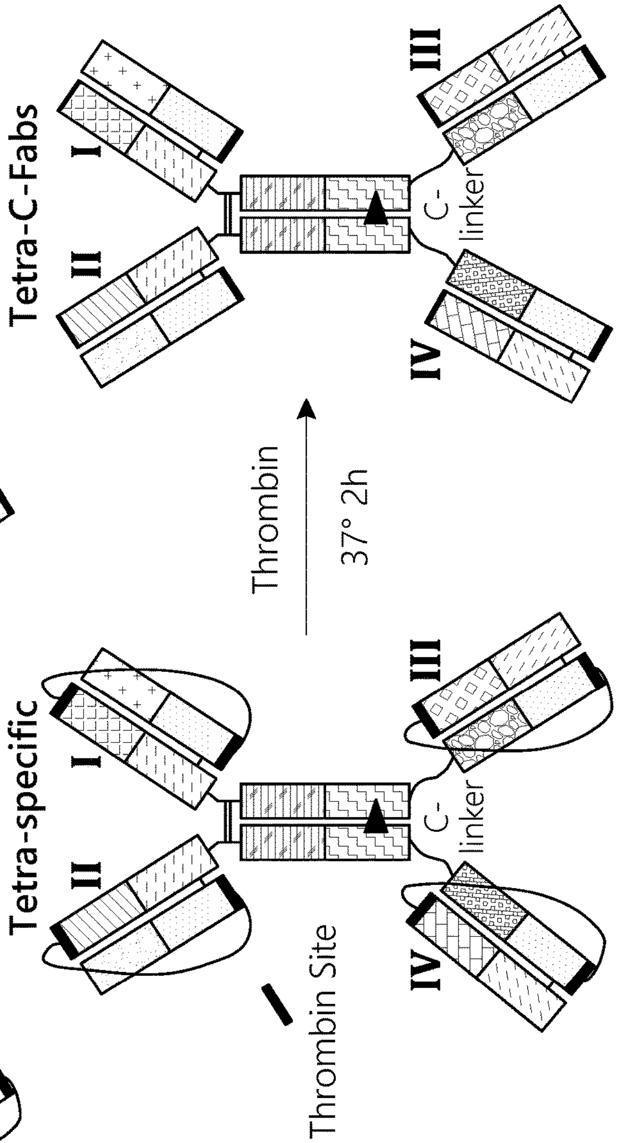
Figure 6D:
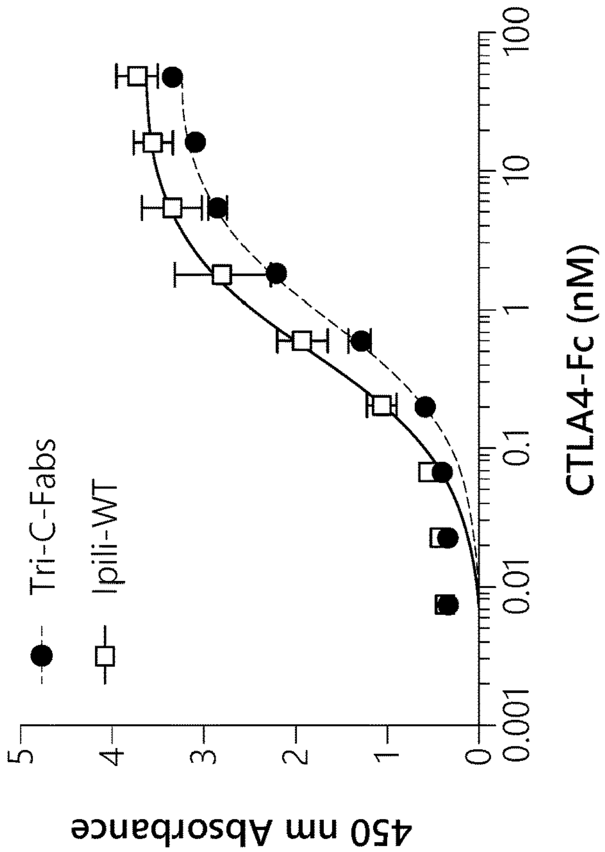

Experimental data presented in FIGS. 6A-6J illustrates an alternative way to arrange the different Fab modules in a tri- or tetra-specific antibody is to append the extra Fabs to the C-terminus of the Fe domain (FIG. 6A for the tri-specific, Tri-C-Fabs; and FIG. 6B for the tetra-specific, Tetra-C-Fabs). For the asymmetric Tri-C-Fabs, the two chains were in the following configuration:

Light chain (I)-sc36TMB linker-Fab heavy chain (I)-"hole" Fc mutant-[C-linker]-light chain (III)-sc36TMB linker-Fab heavy chain (III); and light chain (II)-sc36TMB linker-Fab heavy chain (II)-"knob" Fc mutant (FIG. 6A and SEQ ID NOS: 4 and 11).

The C-linker was designed as a 13-residue long Gly-Ser peptide as shown in SEQ ID NO: 82 of the Sequence Listing.

For the symmetric Tetra-C-Fabs, the two chains were in the following configuration:

Light chain (I/II)-sc36TMB linker-Fab heavy chain (I/II)-"hole"/"knob" Fc mutant-C-linker-light chain (III/IV)-sc36TMB linker-Fab heavy chain (III/IV) (FIG. 6B; SEQ ID NOS: 11 and 12).

These multispecific antibodies were produced by co-transfecting cells with plasmids expressing the corresponding polypeptide chains followed by purification on protein A agarose. The linkers positioned between light and heavy chains were removed by thrombin cleavage prior to analysis.

Figure 6C:
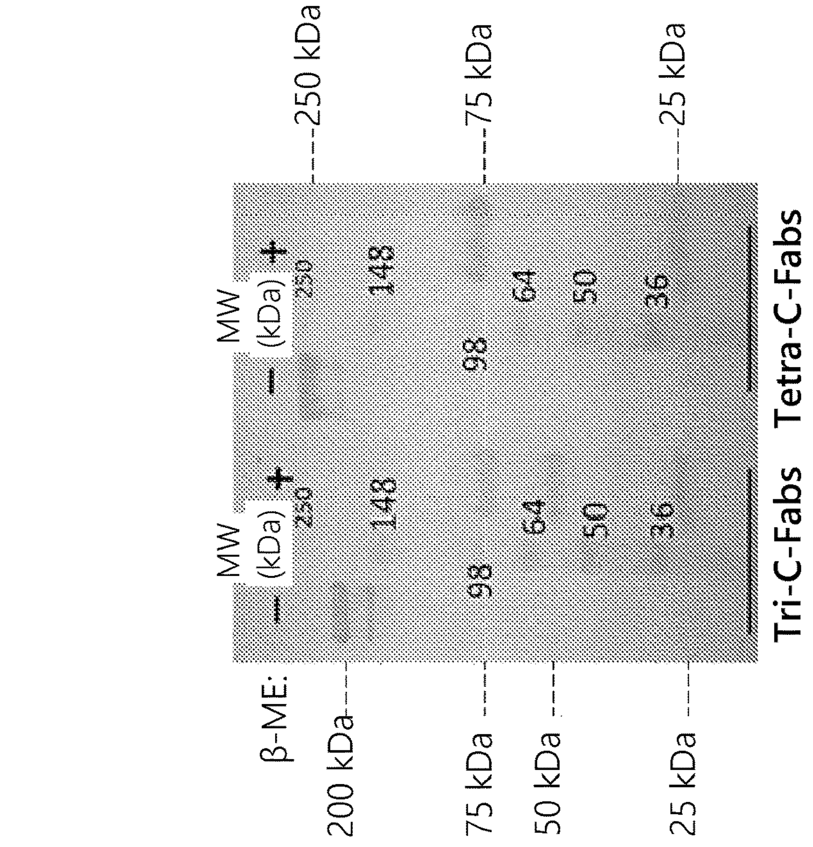
Figure 6F:
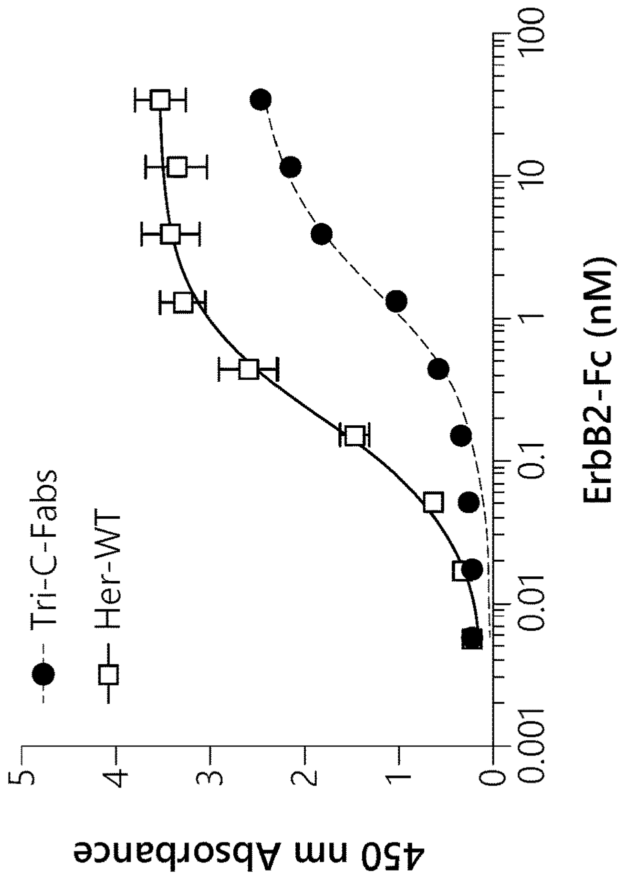
Figure 6E:
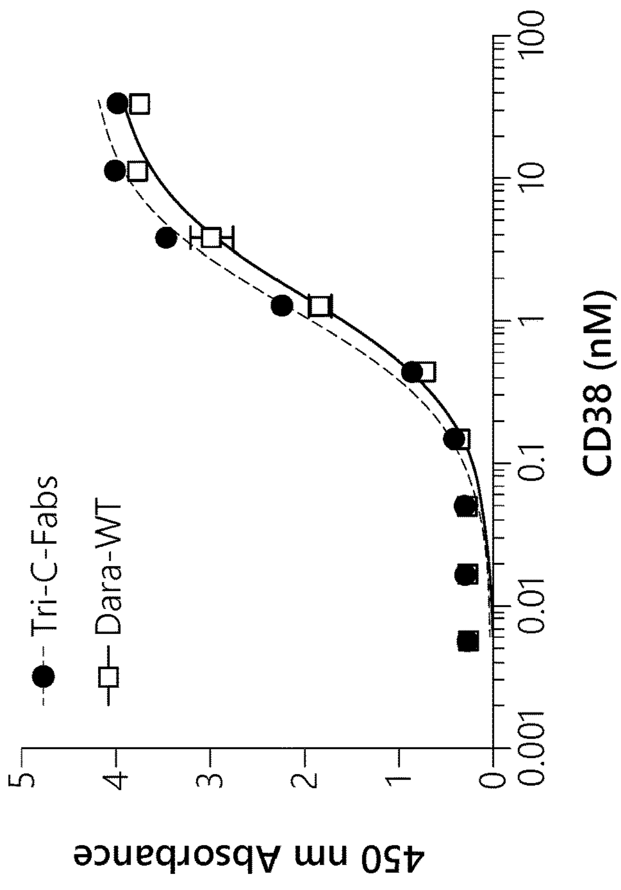
Figure 6H:
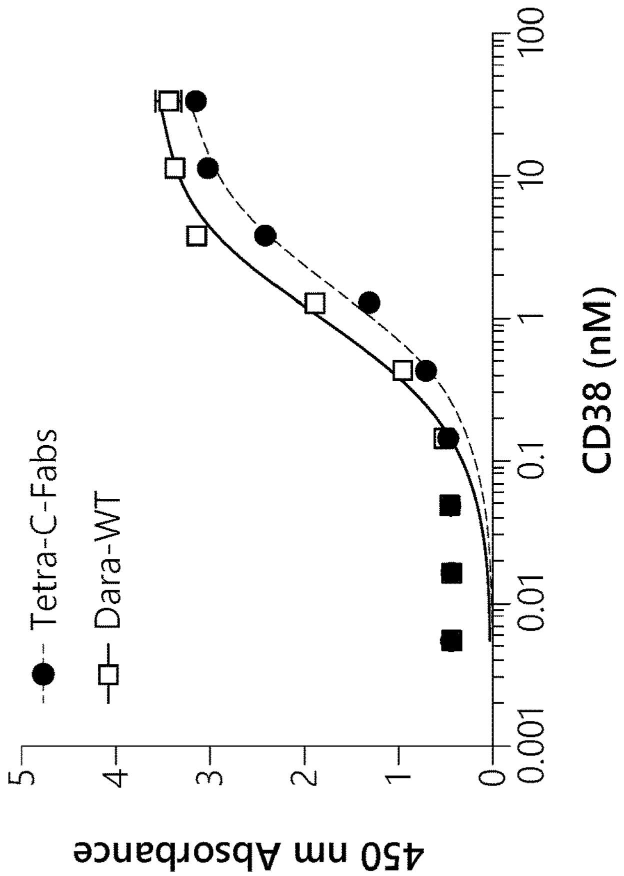
Figure 6G:
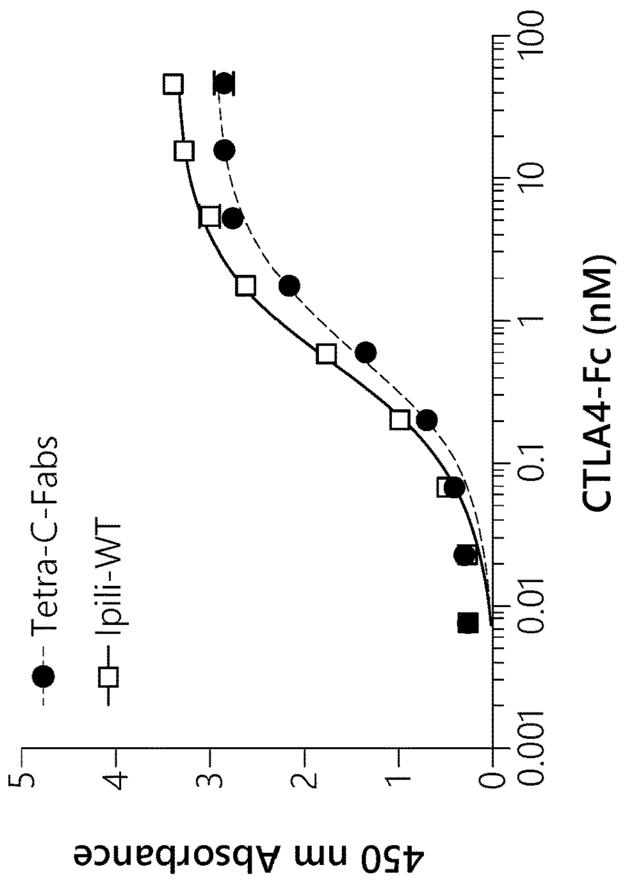
Figure 6J:
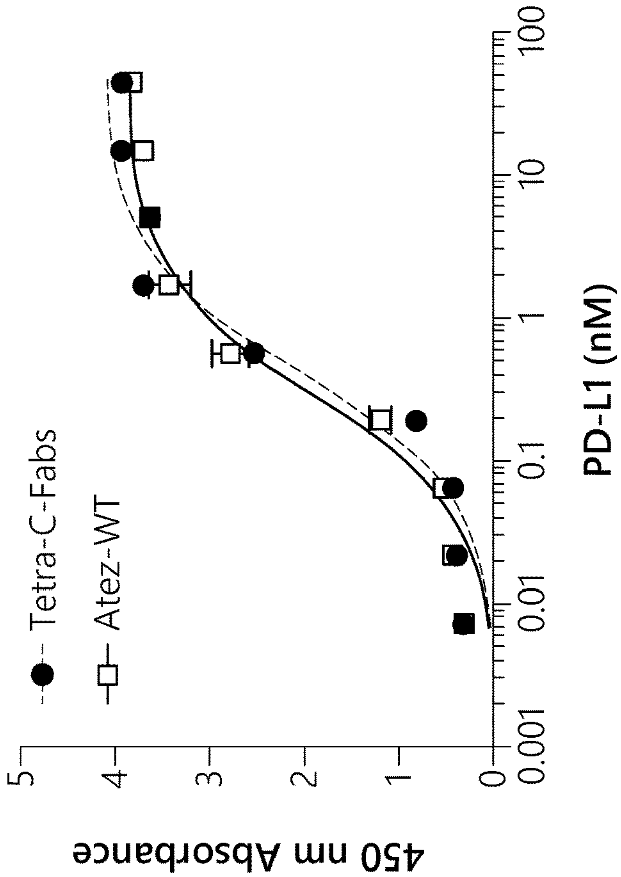
Figure 6I:
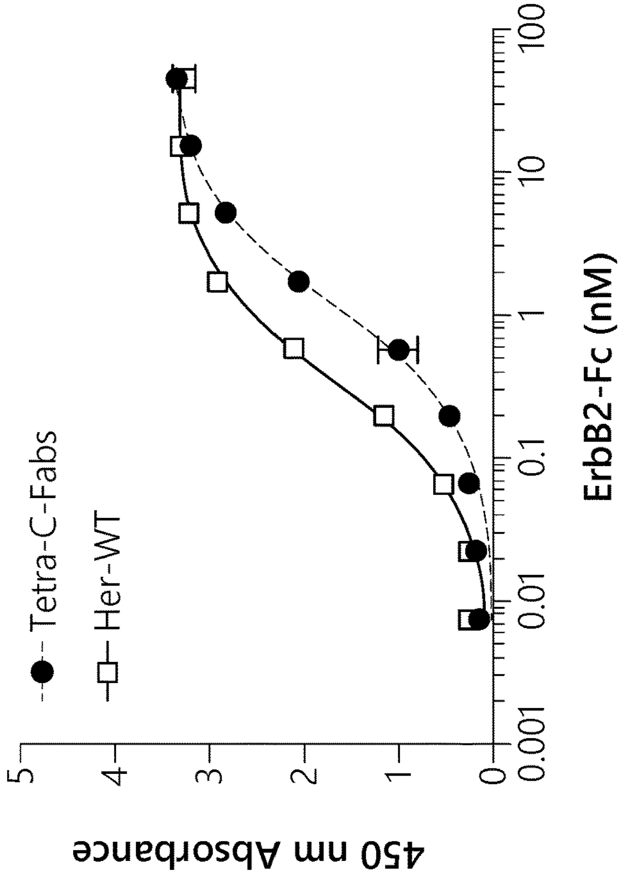
Figure 6K:
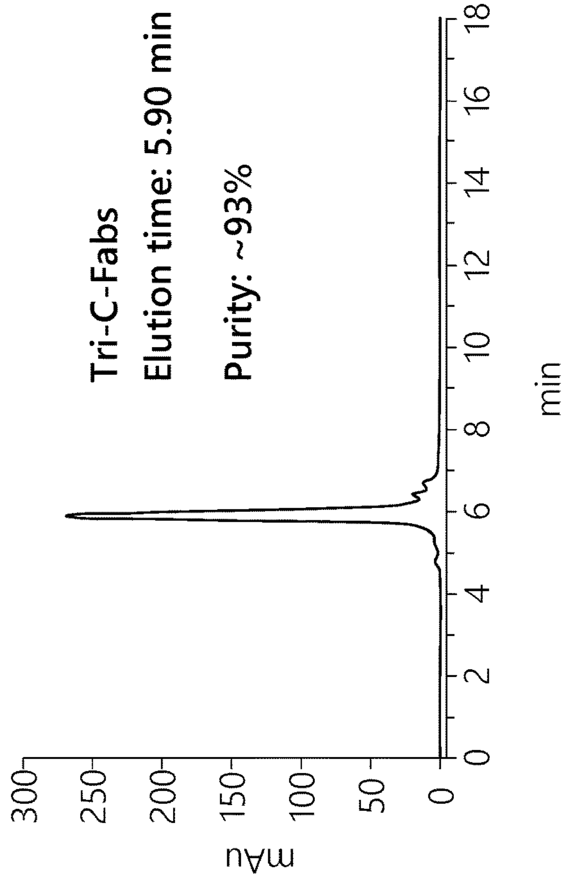
Figure 6L:
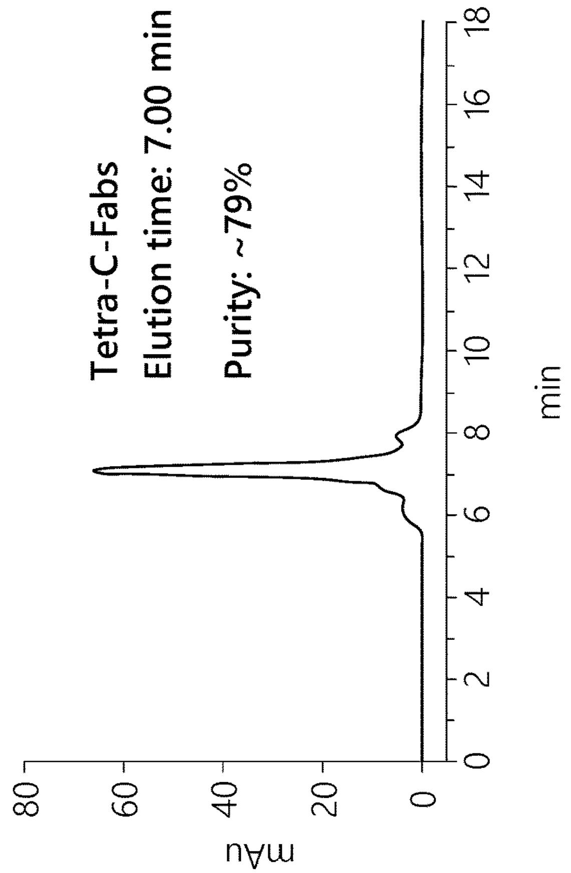

As shown in FIGS. 6A-6J, the following antibodies were successfully produced: a tri-specific antibody (Tri-C-Fabs) with Ipilimumab Fab at position I, Daratumumab Fab at II, and Herceptin Fab at III; and a tetra-specific antibody (Tetra-C-Fabs) with the addition of Atezolizumab Fab at position IV. The main products for both Tri-C-Fabs and Tetra-C-Fabs displayed the correct molecular weights by SDS-PAGE analysis (FIG. 6C). FIGS. 6K-6L summarize the results of a purity assessment of tri-specific and tetra-specific antibodies by analytical hydrophobic interaction chromatography. Purities of Tri-C-Fabs (FIG. 6K) and Tetra-CFabs (FIG. 6L) are estimated to be 93% and 79%, respectively. Both Tri-C-Fabs and Tetra-C-Fabs were able to bind their intended ligands by ELISA, with $EC_{50}$ similar to that of the parental antibodies, i.e., Ipilimumab, Daratumumab, and Atezolizumab (see, FIGS. 6D-6J, and Tables 9-10). In these experiments, estimated EC50 values of ligand binding by Tri-N-Fabs along with the parental antibodies were analyzed by ELISA. $OD_{450}$ values were curve-fit (Prism, GraphPad) to obtain $EC_{50}$ values. It was observed that there was a reduction in target binding by the Herceptin Fab in these multispecific products. With regard to ErbB2 binding, the Tri-C-Fabs and Tetra-C-Fabs display approximately 9- and 3- fold higher $EC_{50}$ values compared to the parental antibody Herceptin. However, the effect seems to be unique to the Herceptin Fab as the Atezolizumab Fab in a similar position in Tetra-C-Fabs was not affected (FIG. 6J).

TABLE 9

Assessment of ligand binding of tri-specific Tri-C-Fabs antibodies. Estimated $EC_{50}$

| Antibody | CTLA4-Fc | CD38 | ErbB2-Fc |
|---|---|---|---|
| Tri-C-Fabs | 0.86 ± 0.11 nM | 1.36 ± 0.13 nM | 2.40 ± 0.26 nM |
| Ipilimumab | 0.50 ± 0.07 nM | — | — |
| Daratumumab | — | 1.68 ± 0.17 nM | — |
| Herceptin | — | — | 0.27 ± 0.03 nM |

TABLE 10

Assessment of ligand binding of tetra-specific Tetra-C-Fabs antibodies. Estimated $EC_{50}$

| Antibody | CTLA4-Fc | CD38 | ErbB2-Fc | PD-L1 |
|---|---|---|---|---|
| Tetra-C-Fabs | 0.64 ± 0.07 nM | 1.73 ± 0.31 nM | 1.30 ± 0.08 nM | 0.45 ± 0.06 nM |
| Ipilimumab | 0.50 ± 0.04 nM | — | — | — |
| Daratumumab | — | 1.08 ± 0.17 nM | — | — |
| Herceptin | — | — | 0.36 ± 0.02 nM | 0.32 ± 0.03 nM |

The binding kinetics of the bispecific or multispecific antibodies to corresponding ligands was also evaluated by biolayer-interferometry (BLI). In these experiments, the biotinylated ligands were immobilized on the streptavidin-coated sensor and measured antibody binding. It was found that the bispecific and multispecific antibodies bind to their ligands in manners expected from their monovalent binding mode Tables 11-12). The parent monoclonal IgGs showed lower Kd values due to avidity (bivalent vs. monovalent), but the parent monovalent Fab (Ipilimumab Fab) showed similar Kd as the bispecific and multispecific antibodies.

TABLE 11

Evaluation of antibody binding kinetics ($K_d$) by biolayer-interferometry. Estimated $K_d$ values by biolayer-interferometry

| Antibody | CTLA4-Fc | CD38 | ErbB2 | PD-L1 |
|---|---|---|---|---|
| Ipilimumab | 3.17E−09 | — | — | — |
| Ipilimumab-Fab | 1.77E−08 | — | — | — |
| Daratumumab | — | 6.9E−10 | — | — |
| Herceptin | — | — | 9.95E−10 | — |
| Atezolizumab | — | — | — | 1.13E−09 |
| Ipili-Dara-KIH | 1.24E−08 | 5.59E−10 | — | — |
| Ipili-Her-KIH | 8.07E−09 | — | 1.28E−09 | — |
| Tri-N-Fabs | 1.06E−08 | 1.71E−08 | 3.26E−09 | — |
| Tri-C-Fabs | 1.17E−08 | 1.40E−08 | 8.49E−09 | — |
| Tetra-N-Fabs | 6.74E−09 | 7.95E−09 | 2.65E−09 | 3.08E−09 |
| Tetra-C-Fabs | 1.46E−08 | 2.76E−09 | 1.29E−08 | 7.14E−09 |

TABLE 12

Evaluation of antibody binding kinetics ($K_{off}$) by biolayer-interferometry. Estimated $K_{off}$ values by biolayer-interferometry

| Antibody | CTLA4-Fc | CD38 | ErbB2 | PD-L1 |
|---|---|---|---|---|
| Ipilimumab | 6.25E−04 | — | — | — |
| Ipilimumab-Fab | 1.77E−03 | — | — | — |
| Daratumumab | — | 1.03E−04 | — | — |
| Herceptin | — | — | 1.55E−04 | — |
| Atezolizumab | — | — | — | 2.75E−04 |
| Ipili-Dara-KIH | 1.58E−03 | 1.21E−04 | — | — |
| Ipili-Her-KIH | 1.20E−03 | — | 1.98E−04 | — |

TABLE 12-continued

Evaluation of antibody binding kinetics ($K_{off}$) by biolayer-interferometry. Estimated $K_{off}$ values by biolayer-interferometry

| Antibody | CTLA4-Fc | CD38 | ErbB2 | PD-L1 |
|---|---|---|---|---|
| Tri-N-Fabs | 1.44E−03 | 1.25E−03 | 3.74E−04 | — |
| Tri-C-Fabs | 2.04E−03 | 1.16E−03 | 6.81E−04 | — |
| Tetra-N-Fabs | 1.53E−03 | 5.75E−03 | 6.87E−04 | 4.22E−04 |
| Tetra-C-Fabs | 1.64E−03 | 2.63E−03 | 6.81E−04 | 5.21E−04 |

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

REFERENCES

1. Schetelig J, Link C S, Stuhler G, Wagner E M, Hanel M, Kobbe G, et al. Anti-CD20 immunotherapy as a bridge to tolerance, after allogeneic stem cell transplantation for patients with chronic lymphocytic leukaemia: results of the CLLX4 trial. Br J Haematol 2019; 184:833-6.
2. Qi J, Li X, Peng H, Cook E M, Dadashian E L, Wiestner A, et al. Potent and selective antitumor activity of a T cell-engaging bispecific antibody targeting a membrane-proximal epitope of ROR1. Proc Natl Acad Sci USA 2018; 115:E5467-E76.
3. Dreier T, Baeuerle P A, Fichtner I, Grun M, Schlereth B, Lorenczewski G, et al. T cell costimulus-independent and very efficacious inhibition of tumor growth in mice bearing subcutaneous or leukemic human B cell lymphoma xenografts by a CD19-/CD3- bispecific single-chain antibody construct. J Immunol 2003; 170:4397-402.
4. Sun L L, Ellerman D, Mathieu M, Hristopoulos M, Chen X, Li Y, et al. Anti-CD20/CD3 T cell-dependent bispecific antibody for the treatment of B cell malignancies. Sci Transl Med 2015; 7:287ra70.
5. Lee N K, Zhang Y, Su Y, Bidlingmaier S, Sherbenou D W, Ha K D, et al. Cell-type specific potent Wnt signaling blockade by bispecific antibody. Scientific reports 2018; 8:766.
6. Lee N K, Su Y, Bidlingmaier S, Liu B. Manipulation of cell-type selective antibody internalization by a guide-effector bispecific design. Molecular cancer therapeutics 2019.
7. de Goeij B E, Vink T, Ten Napel H, Breij E C, Satijn D, Wubbolts R, et al. Efficient Payload Delivery by a Bispecific Antibody-Drug Conjugate Targeting HER2 and CD63. Molecular cancer therapeutics 2016; 15:2688-97.
8. Laursen N S, Friesen R H E, Zhu X, Jongeneelen M, Blokland S, Vermond J, et al. Universal protection against influenza infection by a multidomain antibody to influenza hemagglutinin. Science 2018; 362:598-602.
9. Huang Y, Yu J, Lanzi A, Yao X, Andrews C D, Tsai L, et al. Engineered Bispecific Antibodies with Exquisite HIV-1-Neutralizing Activity. Cell 2016; 165:1621-31.
10. Wagner E K, Wang X, Bui A, Maynard J A. Synergistic Neutralization of Pertussis Toxin by a Bispecific Antibody In vitro and In vivo. Clinical and vaccine immunology: CVI 2016; 23:851-62.
11. Kontermann R E. Dual targeting strategies with bispecific antibodies. MAbs 2012; 4:182-97.
12. Kipriyanov S M, Cochlovius B, Schafer H J, Moldenhauer G, Bahre A, Le Gall F, et al. Synergistic antitumor effect of bispecific CD19×CD3 and CD19×CD16 diabodies in a preclinical model of non-Hodgkin's lymphoma. J Immunol 2002; 169:137-44.
13. Qu Z, Goldenberg D M, Cardillo T M, Shi V, Hansen H J, Chang C H. Bispecific anti-CD20/22 antibodies inhibit B-cell lymphoma proliferation by a unique mechanism of action. Blood 2008; 111:2211-9.
14. Friedman M, Lindstrom S, Ekerljung L, Andersson-Svahn H, Carlsson J, Brismar H, et al. Engineering and characterization of a bispecific HER2×EGFR-binding affibody molecule. Biotechnol Appl Biochem 2009; 54:121-31.
15. Wu C, Ying H, Bose S, Miller R, Medina L, Santora L, et al. Molecular construction and optimization of anti-human IL-1alpha/beta dual variable domain immunoglobulin (DVD-Ig) molecules. MAbs 2009; 1:339-47.
16. Wu C, Ying H, Grinnell C, Bryant S, Miller R, Clabbers A, et al. Simultaneous targeting of multiple disease mediators by a dual-variable-domain immunoglobulin. Nat Biotechnol 2007; 25:1290-7.
17. Schaefer W, Regula J T, Bahner M, Schanzer J, Croasdale R, Durr H, et al. Immunoglobulin domain crossover as a generic approach for the production of bispecific IgG antibodies. Proc Natl Acad Sci USA 2011; 108:11187-92.
18. Sedykh S E, Prinz V V, Buneva V N, Nevinsky G A. Bispecific antibodies: design, therapy, perspectives. Drug Des Devel Ther 2018; 12:195-208.
19. Krishnamurthy A, Jimeno A. Bispecific antibodies for cancer therapy: A review. Pharmacology & therapeutics 2018; 185:122-34.
20. Montefiori D C. Bispecific Antibodies Against HIV. Cell 2016; 165:1563-4.
21. Kontermann R E. Strategies for extended serum half-life of protein therapeutics. Curr Opin Biotechnol 2011; 22:868-76.
22. Niewoehner J, Bohrmann B, Collin L, Urich E, Sade H, Maier P, et al. Increased brain penetration and potency of a therapeutic antibody using a monovalent molecular shuttle. Neuron 2014; 81:49-60.
23. Brinkmann U, Kontermann R E. The making of bispecific antibodies. MAbs 2017; 9:182-212.
24. Thakur A, Lum L G. "NextGen" Biologics: Bispecific Antibodies and Emerging Clinical Results. Expert Opin Biol Ther 2016; 16:675-88.
25. Brennan M, Davison P F, Paulus H. Preparation of bispecific antibodies by chemical recombination of monoclonal immunoglobulin G1 fragments. Science 1985; 229: 81-3.
26. Staerz U D, Kanagawa O, Bevan M J. Hybrid antibodies can target sites for attack by T cells. Nature 1985; 314:628-31.
27. Hayden M S, Linsley P S, Gayle M A, Bajorath J, Brady W A, Norris N A, et al. Single-chain mono- and bispecific antibody derivatives with novel biological properties and antitumour activity from a COS cell transient expression system. Ther Immunol 1994; 1:3-15.
28. Mallender W D, Voss E W, Jr. Construction, expression, and activity of a bivalent bispecific single-chain antibody. J Biol Chem 1994; 269:199-206.
29. Holliger P, Prospero T, Winter G. "Diabodies": small bivalent and bispecific antibody fragments. Proc Natl Acad Sci USA 1993; 90:6444-8.
30. Schoonjans R, Willems A, Schoonooghe S, Fiers W, Grooten J, Mertens N. Fab chains as an efficient heterodimerization scaffold for the production of recombinant bispecific and trispecific antibody derivatives. J Immunol 2000; 165:7050-7.

31. Schoonjans R, Willems A, Schoonooghe S, Leoen J, Grooten J, Mertens N. A new model for intermediate molecular weight recombinant bispecific and trispecific antibodies by efficient heterodimerization of single chain variable domains through fusion to a Fab-chain. Biomol Eng 2001; 17:193-202.

32. Lu D, Jimenez X, Zhang H, Bohlen P, Witte L, Zhu Z. Fab-scFv fusion protein: an efficient approach to production of bispecific antibody fragments. J Immunol Methods 2002; 267:213-26.

33. Chang C H, Rossi E A, Goldenberg D M. The dock and lock method: a novel platform technology for building multivalent, multifunctional structures of defined composition with retained bioactivity. Clinical cancer research: an official journal of the American Association for Cancer Research 2007; 13:5586s-91s.

34. Klein C, Sustmann C, Thomas M, Stubenrauch K, Croasdale R, Schanzer J, et al. Progress in overcoming the chain association issue in bispecific heterodimeric IgG antibodies. MAbs 2012; 4:653-63.

35. Castoldi R, Schanzer J, Panke C, Jucknischke U, Neubert N J, Croasdale R, et al. TetraMabs: simultaneous targeting of four oncogenic receptor tyrosine kinases for tumor growth inhibition in heterogeneous tumor cell populations. Protein Eng Des Sel 2016; 29:467-75.

36. Schmidt D J, Beamer G, Tremblay J M, Steele J A, Kim H B, Wang Y, et al. A Tetraspecific VHH-Based Neutralizing Antibody Modifies Disease Outcome in Three Animal Models of *Clostridium difficile* Infection. Clin Vaccine Immunol 2016; 23:774-84.

37. Hu S, Fu W, Xu W, Yang Y, Cruz M, Berezov S D, et al. Four-in-one antibodies have superior cancer inhibitory activity against EGFR, HER2, HER3, and VEGF through disruption of HER/MET crosstalk. Cancer Res 2015; 75:159-70.

38. Klinger M, Brandl C, Zugmaier G, Hijazi Y, Bargou R C, Topp M S, et al. Immunopharmacologic response of patients with B-lineage acute lymphoblastic leukemia to continuous infusion of T cell-engaging CD19/CD3-bispecific BiTE antibody blinatumomab. Blood 2012; 119:6226-33.

39. Jain T, Sun T, Durand S, Hall A, Houston N R, Nett J H, et al. Biophysical properties of the clinical-stage antibody landscape. Proc Natl Acad Sci USA 2017; 114:944-9.

40. Orcutt $K_D$, Ackerman M E, Cieslewicz M, Quiroz E, Slusarczyk A L, Frangioni J V, et al. A modular IgG-scFv bispecific antibody topology. Protein Eng Des Sel 2010; 23:221-8.

41. Ridgway J B, Presta L G, Carter P. ‘Knobs-into-holes’ engineering of antibody CH3 domains for heavy chain heterodimerization. Protein Eng 1996; 9:617-21.

42. Atwell S, Ridgway J B, Wells J A, Carter P. Stable heterodimers from remodeling the domain interface of a homodimer using a phage display library. J Mol Biol 1997; 270:26-35.

43. Dall’Acqua W, Simon A L, Mulkerrin M G, Carter P. Contribution of domain interface residues to the stability of antibody CH3 domain homodimers. Biochemistry 1998; 37:9266-73.

44. Yin Y, Han G, Zhou J, Dillon M, McCarty L, Gavino L, et al. Precise quantification of mixtures of bispecific IgG produced in single host cells by liquid chromatography-Orbitrap high-resolution mass spectrometry. MAbs 2016; 8:1467-76.

45. Von Kreudenstein T S, Escobar-Carbrera E, Lario P I, D’Angelo I, Brault K, Kelly J, et al. Improving biophysical properties of a bispecific antibody scaffold to aid developability: quality by molecular design. MAbs 2013; 5:646-54.

46. Merchant A M, Zhu Z, Yuan J Q, Goddard A, Adams C W, Presta L G, et al. An efficient route to human bispecific IgG. Nat Biotechnol 1998; 16:677-81.

47. Elliott J M, Ultsch M, Lee J, Tong R, Takeda K, Spiess C, et al. Antiparallel conformation of knob and hole aglycosylated half-antibody homodimers is mediated by a CH2-CH3 hydrophobic interaction. J Mol Biol 2014; 426:1947-57.

48. Wei H, Cai H, Jin Y, Wang P, Zhang Q, Lin Y, et al. Structural basis of a novel heterodimeric Fc for bispecific antibody production. Oncotarget 2017; 8:51037-49.

49. Zhu Z, Presta L G, Zapata G, Carter P. Remodeling domain interfaces to enhance heterodimer formation. Protein Sci 1997; 6:781-8.

50. Carter P. Bispecific human IgG by design. J Immunol Methods 2001; 248:7-15.

51. Van Blarcom T, Lindquist K, Melton Z, Cheung W L, Wagstrom C, McDonough D, et al. Productive common light chain libraries yield diverse panels of high affinity bispecific antibodies. mAbs 2018; 10:256-68.

52. Krah S, Schroter C, Eller C, Rhiel L, Rasche N, Beck J, et al. Generation of human bispecific common light chain antibodies by combining animal immunization and yeast display. Protein Eng Des Sel 2017; 30:291-301.

53. Klein C, Schaefer W, Regula J T. The use of CrossMAb technology for the generation of bi- and multispecific antibodies. MAbs 2016; 8:1010-20.

54. Steinwand M, Droste P, Frenzel A, Hust M, Dubel S, Schirrmann T. The influence of antibody fragment format on phage display based affinity maturation of IgG. MAbs 2014; 6:204-18.

55. Schirrmann T, Menzel C, Hust M, Prilop J, Jostock T, Dubel S. Oligomeric forms of single chain immunoglobulin (scIgG). mAbs 2010; 2:73-6.

56. Koerber J T, Hornsby M J, Wells J A. An improved single-chain Fab platform for efficient display and recombinant expression. J Mol Biol 2015; 427:576-86.

57. Wranik B J, Christensen E L, Schaefer G, Jackman J K, Vendel A C, Eaton D. LUZ-Y, a novel platform for the mammalian cell production of full-length IgG-bispecific antibodies. J Biol Chem 2012; 287:43331-9.

58. Funaro A, Reinis M, Trubiani O, Santi S, Di Primio R, Malavasi F. CD38 functions are regulated through an internalization step. J Immunol 1998; 160:2238-47.

59. Yamamoto K, Ichijo H, Korsmeyer S J. BCL-2 is phosphorylated and inactivated by an ASK1/Jun N-terminal protein kinase pathway normally activated at G(2)/M. Mol Cell Biol 1999; 19:8469-78.

60. Contardi E, Palmisano G L, Tazzari P L, Martelli A M, Fala F, Fabbi M, et al. CTLA-4 is constitutively expressed on tumor cells and can trigger apoptosis upon ligand interaction. Int J Cancer 2005; 117:538-50.

61. Smith K, Garman L, Wrammert J, Zheng N Y, Capra J D, Ahmed R, et al. Rapid generation of fully human monoclonal antibodies specific to a vaccinating antigen. Nat Protoc 2009; 4:372-84.

62. Li C, Evans R M. Ligation independent cloning irrespective of restriction site compatibility. Nucleic acids research 1997; 25:4165-6.

What is claimed is:

1. An engineered antibody comprising a first and a second polypeptide chain, each of the first and second polypeptide chains comprising:

(a) a single-chain antigen-binding (scFab) fragment comprising, in N-terminal to C-terminal direction:

(i) a light chain variable domain (VL);

(ii) a light chain constant domain (CL);

(iii) a removable linker comprising the sequence of SEQ ID NO: 80;

(iv) a heavy chain variable domain (VH); and (v) a heavy chain constant domain CH1, wherein the scFab fragments of the first and second polypeptide chains have specificity for different antigens; and (b) an antibody Fc region N-terminally linked to the scFab fragment in (a), wherein the Fc regions of the first and a second polypeptide chains are associated with one another via an interface which has been modified to promote heterodimer formation.

2. The engineered antibody of claim 1, wherein the C-terminus and/or the N-terminus of at least one of the first and the second polypeptide chains is operably linked to one or more additional scFab fragments having specificity for additional antigens.

3. The engineered antibody of claim 1, wherein the one or more proteolytic cleavage sites can be cleaved by a protease or an endopeptidase.

4. The engineered antibody of claim 3, wherein the protease is selected from the group consisting of thrombin, PreScission™ protease, and tobacco etch virus (TEV) protease.

5. The engineered antibody of claim 3, wherein the endopeptidase is selected from the group consisting of trypsin, chymotrypsin, elastase, thermolysin, pepsin, glutamyl endopeptidase, or neprilysin.

6. The engineered antibody of claim 1, wherein the removable linker further comprises one or more affinity tags.

7. The engineered antibody of claim 6, wherein the one or more affinity tags is selected from the group consisting of polyhistidine (poly-His) tags, hemagglutinin (HA) tags, Avi-Tag™, protein C tags, FLAG tags, Strep-tag® II, Twin-Strep-tag®, glutathione-S-transferase (GST), C-myc tag, chitin-binding domain, Streptavidin binding proteins (SBP), maltose binding protein (MBP), cellulose-binding domains, calmodulin-binding peptides, and S-tags.

8. The engineered antibody of claim 6, wherein the removable linker further comprises one or more polypeptide dimerization motifs selected from the group consisting of homodimerization motifs, heterodimerization motifs, leucine zipper motifs, and combinations of any thereof.

9. The engineered antibody of claim 6, wherein the Fc regions of the first and the second polypeptide chains are associated with one another via a modified interface that is located within a constant domain of the Fc regions.

10. The engineered antibody of claim 9, wherein the modified interface of the first polypeptide chain comprises a protuberance which is positionable in a cavity in the modified interface of the second polypeptide chain.

11. The engineered antibody of claim 10, the amino acid sequence of an original interface has been modified so as to introduce the protuberance and/or cavity into the modified interface such that a greater ratio of heterodimer: homodimer forms than that for a dimer having a non-modified interface.

12. The engineered antibody of claim 11, wherein (a) the cavity comprises an amino acid residue substituted into the interface of the second polypeptide, and wherein the substituted amino acid residue is selected from the group consisting of alanine (A), serine(S), threonine (T), and valine (V); and/or (b) the protuberance comprises an amino acid residue substituted into the interface of the first polypeptide, and wherein the substituted amino acid residue is selected from the group consisting of arginine (R), phenylalanine (F), tyrosine (Y), and tryptophan (W).

13. The engineered antibody of claim 12, wherein (a) the amino acid residue is substituted into the interface of the first polypeptide at position 347, 349, 350, 351, 366, 368, 370, 392, 394, 395, 397, 398, 399, 405, 407, or 409 of the CH3 domain of human IgG1; and/or (b) the protuberance comprises a T366W amino acid substitution within the constant domain CH3 of the Fc region of the first polypeptide; and/or (c) the cavity comprises an amino acid substitution selected from the group consisting of S354C, T366S, L368A, and Y407V present within the constant domain CH3 of the Fc region of the second polypeptide.

14. The engineered antibody of claim 2, wherein the one or more additional scFab fragments are operably linked to the first polypeptide chain and/or the second polypeptide chain by a connector.

15. A recombinant nucleic acid comprising a nucleic acid sequence that encodes at least one of the first and the second polypeptide chains of an engineered antibody according to claim 1 or a scFab fragment thereof.

16. A recombinant cell comprising one or more of the following:

(a) an engineered antibody according to claim 1;

(b) at least one of the first and the second polypeptide chains of an engineered antibody according to (a) or a scFab fragment thereof; and (c) a recombinant nucleic acid comprising a nucleic acid sequence that encodes (a) or (b).

17. A method for preparing an engineered antibody, comprising:

(a) providing an engineered antibody according to claim 1; and (b) removing the removable linker to produce an antibody that does not contain the removable linker.

18. An antibody prepared by a method according to claim 17.

19. A pharmaceutical composition comprising the antibody of claim 18, and a pharmaceutically acceptable carrier.

20. The engineered antibody of claim 1, wherein the Fc regions of the first and the second polypeptide chains are associated with one another via a modified interface that is located within a constant domain of the Fc regions.

21. The engineered antibody of claim 7, wherein the one or more affinity tags comprises a poly-His tag or a Twin-Strep-tag®.

22. The engineered antibody of claim 21, wherein the removable linker comprises the sequence of SEQ ID NO: 35 or SEQ ID NO: 40.

* * * * *

SEQUENCE LISTING

<160> NUMBER OF SEQ ID NOS: 83

<210> SEQ ID NO 1
<211> LENGTH: 731
<212> TYPE: PRT
<213> ORGANISM: Artificial Sequence
<220> FEATURE:
<223> OTHER INFORMATION: Light chain (Ipil)-sc36TMB linker-Heavy chain
(Ipil)-Fc region

<400> SEQUENCE: 1

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Gly Ser Ser Tyr Leu Ala Trp Tyr Gln Gln Lys Pro Gly Gln Ala Pro
    50                  55                  60

Arg Leu Leu Ile Tyr Gly Ala Phe Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Ser Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Leu Val Pro Arg Gly
225                 230                 235                 240

Ser Gly Ser Gly Gly Gly Ser Gly Gly Gly Ser Glu Gly Gly Gly Ser
                245                 250                 255

Glu Gly Gly Gly Ser Glu Gly Gly Gly Ser Glu Gly Gly Gly Ser Gly
            260                 265                 270

Gly Gly Ser Gly Gly Leu Val Pro Arg Gly Ser Gln Val Gln Leu Val
        275                 280                 285

Glu Ser Gly Gly Gly Val Val Gln Pro Gly Arg Ser Leu Arg Leu Ser
    290                 295                 300

Cys Ala Ala Ser Gly Phe Thr Phe Ser Ser Tyr Thr Met His Trp Val
305                 310                 315                 320

Arg Gln Ala Pro Gly Lys Gly Leu Glu Trp Val Thr Phe Ile Ser Tyr
                325                 330                 335

Asp Gly Asn Asn Lys Tyr Tyr Ala Asp Ser Val Lys Gly Arg Phe Thr
            340                 345                 350
```

```
Ile Ser Arg Asp Asn Ser Lys Asn Thr Leu Tyr Leu Gln Met Asn Ser
        355                 360                 365

Leu Arg Ala Glu Asp Thr Ala Ile Tyr Tyr Cys Ala Arg Thr Gly Trp
    370                 375                 380

Leu Gly Pro Phe Asp Tyr Trp Gly Gln Gly Thr Leu Val Thr Val Ser
385                 390                 395                 400

Ser Ala Ser Thr Lys Gly Pro Ser Val Phe Pro Leu Ala Pro Ser Ser
                405                 410                 415

Lys Ser Thr Ser Gly Gly Thr Ala Ala Leu Gly Cys Leu Val Lys Asp
            420                 425                 430

Tyr Phe Pro Glu Pro Val Thr Val Ser Trp Asn Ser Gly Ala Leu Thr
        435                 440                 445

Ser Gly Val His Thr Phe Pro Ala Val Leu Gln Ser Ser Gly Leu Tyr
    450                 455                 460

Ser Leu Ser Ser Val Val Thr Val Pro Ser Ser Ser Leu Gly Thr Gln
465                 470                 475                 480

Thr Tyr Ile Cys Asn Val Asn His Lys Pro Ser Asn Thr Lys Val Asp
                485                 490                 495

Lys Lys Val Glu Pro Lys Ser Cys Asp Lys Thr His Thr Cys Pro Pro
            500                 505                 510

Cys Pro Ala Pro Glu Leu Leu Gly Gly Pro Ser Val Phe Leu Phe Pro
        515                 520                 525

Pro Lys Pro Lys Asp Thr Leu Met Ile Ser Arg Thr Pro Glu Val Thr
    530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Asn Ser Thr Tyr Arg Val Val Ser Val Leu Thr Val
            580                 585                 590

Leu His Gln Asp Trp Leu Asn Gly Lys Glu Tyr Lys Cys Lys Val Ser
        595                 600                 605

Asn Lys Ala Leu Pro Ala Pro Ile Glu Lys Thr Ile Ser Lys Ala Lys
    610                 615                 620

Gly Gln Pro Arg Glu Pro Gln Val Tyr Thr Leu Pro Pro Ser Arg Asp
625                 630                 635                 640

Glu Leu Thr Lys Asn Gln Val Ser Leu Thr Cys Leu Val Lys Gly Phe
                645                 650                 655

Tyr Pro Ser Asp Ile Ala Val Glu Trp Glu Ser Asn Gly Gln Pro Glu
            660                 665                 670

Asn Asn Tyr Lys Thr Thr Pro Pro Val Leu Asp Ser Asp Gly Ser Phe
        675                 680                 685

Phe Leu Tyr Ser Lys Leu Thr Val Asp Lys Ser Arg Trp Gln Gln Gly
    690                 695                 700

Asn Val Phe Ser Cys Ser Val Met His Glu Ala Leu His Asn His Tyr
705                 710                 715                 720

Thr Gln Lys Ser Leu Ser Leu Ser Pro Gly Lys
                725                 730
```

<210> SEQ ID NO 2
<211> LENGTH: 734
<212> TYPE: PRT
<213> ORGANISM: Artificial Sequence
<220> FEATURE:
<223> OTHER INFORMATION: Light chain (Dara)-sc36TMB linker-Heavy chain -continued (Dara)-Fc region

<400> SEQUENCE: 2

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Leu Val Pro Arg Gly Ser
225                 230                 235                 240

Gly Ser Gly Gly Gly Ser Gly Gly Gly Ser Glu Gly Gly Gly Ser Glu
                245                 250                 255

Gly Gly Gly Ser Glu Gly Gly Gly Ser Glu Gly Gly Gly Ser Gly Gly
            260                 265                 270

Gly Ser Gly Gly Leu Val Pro Arg Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Val Ser Gly Phe Thr Phe Asn Ser Phe Ala Met Ser Trp Val Arg
305                 310                 315                 320

Gln Ala Pro Gly Lys Gly Leu Glu Trp Val Ser Ala Ile Ser Gly Ser
                325                 330                 335

Gly Gly Gly Thr Tyr Tyr Ala Asp Ser Val Lys Gly Arg Phe Thr Ile
            340                 345                 350

Ser Arg Asp Asn Ser Lys Asn Thr Leu Tyr Leu Gln Met Asn Ser Leu
        355                 360                 365

Arg Ala Glu Asp Thr Ala Val Tyr Phe Cys Ala Lys Asp Lys Ile Leu
    370                 375                 380

Trp Phe Gly Glu Pro Val Phe Asp Tyr Trp Gly Gln Gly Thr Leu Val
385                 390                 395                 400
```

```
Thr Val Ser Ser Ala Ser Thr Lys Gly Pro Ser Val Phe Pro Leu Ala
                405                 410                 415

Pro Ser Ser Lys Ser Thr Ser Gly Gly Thr Ala Ala Leu Gly Cys Leu
            420                 425                 430

Val Lys Asp Tyr Phe Pro Glu Pro Val Thr Val Ser Trp Asn Ser Gly
        435                 440                 445

Ala Leu Thr Ser Gly Val His Thr Phe Pro Ala Val Leu Gln Ser Ser
    450                 455                 460

Gly Leu Tyr Ser Leu Ser Ser Val Val Thr Val Pro Ser Ser Ser Leu
465                 470                 475                 480

Gly Thr Gln Thr Tyr Ile Cys Asn Val Asn His Lys Pro Ser Asn Thr
                485                 490                 495

Lys Val Asp Lys Lys Val Glu Pro Lys Ser Cys Asp Lys Thr His Thr
            500                 505                 510

Cys Pro Pro Cys Pro Ala Pro Glu Leu Leu Gly Gly Pro Ser Val Phe
        515                 520                 525

Leu Phe Pro Pro Lys Pro Lys Asp Thr Leu Met Ile Ser Arg Thr Pro
    530                 535                 540

Glu Val Thr Cys Val Val Val Asp Val Ser His Glu Asp Pro Glu Val
545                 550                 555                 560

Lys Phe Asn Trp Tyr Val Asp Gly Val Glu Val His Asn Ala Lys Thr
                565                 570                 575

Lys Pro Arg Glu Glu Gln Tyr Asn Ser Thr Tyr Arg Val Val Ser Val
            580                 585                 590

Leu Thr Val Leu His Gln Asp Trp Leu Asn Gly Lys Glu Tyr Lys Cys
        595                 600                 605

Lys Val Ser Asn Lys Ala Leu Pro Ala Pro Ile Glu Lys Thr Ile Ser
    610                 615                 620

Lys Ala Lys Gly Gln Pro Arg Glu Pro Gln Val Tyr Thr Leu Pro Pro
625                 630                 635                 640

Ser Arg Asp Glu Leu Thr Lys Asn Gln Val Ser Leu Thr Cys Leu Val
                645                 650                 655

Lys Gly Phe Tyr Pro Ser Asp Ile Ala Val Glu Trp Glu Ser Asn Gly
            660                 665                 670

Gln Pro Glu Asn Asn Tyr Lys Thr Thr Pro Pro Val Leu Asp Ser Asp
        675                 680                 685

Gly Ser Phe Phe Leu Tyr Ser Lys Leu Thr Val Asp Lys Ser Arg Trp
    690                 695                 700

Gln Gln Gly Asn Val Phe Ser Cys Ser Val Met His Glu Ala Leu His
705                 710                 715                 720

Asn His Tyr Thr Gln Lys Ser Leu Ser Leu Ser Pro Gly Lys
                725                 730


<210> SEQ ID NO 3
<211> LENGTH: 731
<212> TYPE: PRT
<213> ORGANISM: Artificial Sequence
<220> FEATURE:
<223> OTHER INFORMATION: Light chain (Ipil)-sc36TMB linker-Heavy chain
      (Ipil)-Fc region (Hole)

<400> SEQUENCE: 3

Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
            20                  25                  30
```

```
Ser Pro Gly Glu Arg Ala Thr Leu Ser Cys Arg Ala Ser Gln Ser Val
        35                  40                  45

Gly Ser Ser Tyr Leu Ala Trp Tyr Gln Gln Lys Pro Gly Gln Ala Pro
    50                  55                  60

Arg Leu Leu Ile Tyr Gly Ala Phe Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Ser Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Leu Val Pro Arg Gly
225                 230                 235                 240

Ser Gly Ser Gly Gly Gly Ser Gly Gly Gly Ser Glu Gly Gly Gly Ser
                245                 250                 255

Glu Gly Gly Gly Ser Glu Gly Gly Gly Ser Glu Gly Gly Gly Ser Gly
            260                 265                 270

Gly Gly Ser Gly Gly Leu Val Pro Arg Gly Ser Gln Val Gln Leu Val
        275                 280                 285

Glu Ser Gly Gly Gly Val Val Gln Pro Gly Arg Ser Leu Arg Leu Ser
    290                 295                 300

Cys Ala Ala Ser Gly Phe Thr Phe Ser Ser Tyr Thr Met His Trp Val
305                 310                 315                 320

Arg Gln Ala Pro Gly Lys Gly Leu Glu Trp Val Thr Phe Ile Ser Tyr
                325                 330                 335

Asp Gly Asn Asn Lys Tyr Tyr Ala Asp Ser Val Lys Gly Arg Phe Thr
            340                 345                 350

Ile Ser Arg Asp Asn Ser Lys Asn Thr Leu Tyr Leu Gln Met Asn Ser
        355                 360                 365

Leu Arg Ala Glu Asp Thr Ala Ile Tyr Tyr Cys Ala Arg Thr Gly Trp
    370                 375                 380

Leu Gly Pro Phe Asp Tyr Trp Gly Gln Gly Thr Leu Val Thr Val Ser
385                 390                 395                 400

Ser Ala Ser Thr Lys Gly Pro Ser Val Phe Pro Leu Ala Pro Ser Ser
                405                 410                 415

Lys Ser Thr Ser Gly Gly Thr Ala Ala Leu Gly Cys Leu Val Lys Asp
            420                 425                 430

Tyr Phe Pro Glu Pro Val Thr Val Ser Trp Asn Ser Gly Ala Leu Thr
        435                 440                 445
```

```
Ser Gly Val His Thr Phe Pro Ala Val Leu Gln Ser Ser Gly Leu Tyr
    450                 455                 460

Ser Leu Ser Ser Val Val Thr Val Pro Ser Ser Ser Leu Gly Thr Gln
465                 470                 475                 480

Thr Tyr Ile Cys Asn Val Asn His Lys Pro Ser Asn Thr Lys Val Asp
                485                 490                 495

Lys Lys Val Glu Pro Lys Ser Cys Asp Lys Thr His Thr Cys Pro Pro
            500                 505                 510

Cys Pro Ala Pro Glu Leu Leu Gly Gly Pro Ser Val Phe Leu Phe Pro
        515                 520                 525

Pro Lys Pro Lys Asp Thr Leu Met Ile Ser Arg Thr Pro Glu Val Thr
    530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Asn Ser Thr Tyr Arg Val Val Ser Val Leu Thr Val
            580                 585                 590

Leu His Gln Asp Trp Leu Asn Gly Lys Glu Tyr Lys Cys Lys Val Ser
        595                 600                 605

Asn Lys Ala Leu Pro Ala Pro Ile Glu Lys Thr Ile Ser Lys Ala Lys
    610                 615                 620

Gly Gln Pro Arg Glu Pro Gln Val Cys Thr Leu Pro Pro Ser Arg Asp
625                 630                 635                 640

Glu Leu Thr Lys Asn Gln Val Ser Leu Ser Cys Ala Val Lys Gly Phe
                645                 650                 655

Tyr Pro Ser Asp Ile Ala Val Glu Trp Glu Ser Asn Gly Gln Pro Glu
            660                 665                 670

Asn Asn Tyr Lys Thr Thr Pro Pro Val Leu Asp Ser Asp Gly Ser Phe
        675                 680                 685

Phe Leu Val Ser Lys Leu Thr Val Asp Lys Ser Arg Trp Gln Gln Gly
    690                 695                 700

Asn Val Phe Ser Cys Ser Val Met His Glu Ala Leu His Asn His Tyr
705                 710                 715                 720

Thr Gln Lys Ser Leu Ser Leu Ser Pro Gly Lys
                725                 730


<210> SEQ ID NO 4
<211> LENGTH: 734
<212> TYPE: PRT
<213> ORGANISM: Artificial Sequence
<220> FEATURE:
<223> OTHER INFORMATION: Light chain (Dara)-sc36TMB linker- Heavy chain
      (Dara)-Fc region (Knob)

<400> SEQUENCE: 4

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80
```

```
Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Leu Val Pro Arg Gly Ser
225                 230                 235                 240

Gly Ser Gly Gly Gly Ser Gly Gly Gly Ser Glu Gly Gly Gly Ser Glu
                245                 250                 255

Gly Gly Gly Ser Glu Gly Gly Gly Ser Glu Gly Gly Gly Ser Gly Gly
            260                 265                 270

Gly Ser Gly Gly Leu Val Pro Arg Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Val Ser Gly Phe Thr Phe Asn Ser Phe Ala Met Ser Trp Val Arg
305                 310                 315                 320

Gln Ala Pro Gly Lys Gly Leu Glu Trp Val Ser Ala Ile Ser Gly Ser
                325                 330                 335

Gly Gly Gly Thr Tyr Tyr Ala Asp Ser Val Lys Gly Arg Phe Thr Ile
            340                 345                 350

Ser Arg Asp Asn Ser Lys Asn Thr Leu Tyr Leu Gln Met Asn Ser Leu
        355                 360                 365

Arg Ala Glu Asp Thr Ala Val Tyr Phe Cys Ala Lys Asp Lys Ile Leu
    370                 375                 380

Trp Phe Gly Glu Pro Val Phe Asp Tyr Trp Gly Gln Gly Thr Leu Val
385                 390                 395                 400

Thr Val Ser Ser Ala Ser Thr Lys Gly Pro Ser Val Phe Pro Leu Ala
                405                 410                 415

Pro Ser Ser Lys Ser Thr Ser Gly Gly Thr Ala Ala Leu Gly Cys Leu
            420                 425                 430

Val Lys Asp Tyr Phe Pro Glu Pro Val Thr Val Ser Trp Asn Ser Gly
        435                 440                 445

Ala Leu Thr Ser Gly Val His Thr Phe Pro Ala Val Leu Gln Ser Ser
    450                 455                 460

Gly Leu Tyr Ser Leu Ser Ser Val Val Thr Val Pro Ser Ser Ser Leu
465                 470                 475                 480

Gly Thr Gln Thr Tyr Ile Cys Asn Val Asn His Lys Pro Ser Asn Thr
                485                 490                 495
```

```
Lys Val Asp Lys Lys Val Glu Pro Lys Ser Cys Asp Lys Thr His Thr
            500                 505                 510

Cys Pro Pro Cys Pro Ala Pro Glu Leu Leu Gly Gly Pro Ser Val Phe
        515                 520                 525

Leu Phe Pro Pro Lys Pro Lys Asp Thr Leu Met Ile Ser Arg Thr Pro
    530                 535                 540

Glu Val Thr Cys Val Val Val Asp Val Ser His Glu Asp Pro Glu Val
545                 550                 555                 560

Lys Phe Asn Trp Tyr Val Asp Gly Val Glu Val His Asn Ala Lys Thr
                565                 570                 575

Lys Pro Arg Glu Glu Gln Tyr Asn Ser Thr Tyr Arg Val Val Ser Val
            580                 585                 590

Leu Thr Val Leu His Gln Asp Trp Leu Asn Gly Lys Glu Tyr Lys Cys
        595                 600                 605

Lys Val Ser Asn Lys Ala Leu Pro Ala Pro Ile Glu Lys Thr Ile Ser
    610                 615                 620

Lys Ala Lys Gly Gln Pro Arg Glu Pro Gln Val Tyr Thr Leu Pro Pro
625                 630                 635                 640

Cys Arg Asp Glu Leu Thr Lys Asn Gln Val Ser Leu Trp Cys Leu Val
                645                 650                 655

Lys Gly Phe Tyr Pro Ser Asp Ile Ala Val Glu Trp Glu Ser Asn Gly
            660                 665                 670

Gln Pro Glu Asn Asn Tyr Lys Thr Thr Pro Pro Val Leu Asp Ser Asp
        675                 680                 685

Gly Ser Phe Phe Leu Tyr Ser Lys Leu Thr Val Asp Lys Ser Arg Trp
    690                 695                 700

Gln Gln Gly Asn Val Phe Ser Cys Ser Val Met His Glu Ala Leu His
705                 710                 715                 720

Asn His Tyr Thr Gln Lys Ser Leu Ser Leu Ser Pro Gly Lys
                725                 730


<210> SEQ ID NO 5
<211> LENGTH: 732
<212> TYPE: PRT
<213> ORGANISM: Artificial Sequence
<220> FEATURE:
<223> OTHER INFORMATION: Light chain (Her)-sc36TMB linker-Heavy chain
      (Her)-Fc region (Knob)

<400> SEQUENCE: 5

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125
```

```
Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Leu Val Pro Arg Gly Ser
225                 230                 235                 240

Gly Ser Gly Gly Gly Ser Gly Gly Gly Ser Glu Gly Gly Gly Ser Glu
                245                 250                 255

Gly Gly Gly Ser Glu Gly Gly Gly Ser Glu Gly Gly Gly Ser Gly Gly
            260                 265                 270

Gly Ser Gly Gly Leu Val Pro Arg Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Phe Asn Ile Lys Asp Thr Tyr Ile His Trp Val Arg
305                 310                 315                 320

Gln Ala Pro Gly Lys Gly Leu Glu Trp Val Ala Arg Ile Tyr Pro Thr
                325                 330                 335

Asn Gly Tyr Thr Arg Tyr Ala Asp Ser Val Lys Gly Arg Phe Thr Ile
            340                 345                 350

Ser Ala Asp Thr Ser Lys Asn Thr Ala Tyr Leu Gln Met Asn Ser Leu
        355                 360                 365

Arg Ala Glu Asp Thr Ala Val Tyr Tyr Cys Ser Arg Trp Gly Gly Asp
    370                 375                 380

Gly Phe Tyr Ala Met Asp Tyr Trp Gly Gln Gly Thr Leu Val Thr Val
385                 390                 395                 400

Ser Ser Ala Ser Thr Lys Gly Pro Ser Val Phe Pro Leu Ala Pro Ser
                405                 410                 415

Ser Lys Ser Thr Ser Gly Gly Thr Ala Ala Leu Gly Cys Leu Val Lys
            420                 425                 430

Asp Tyr Phe Pro Glu Pro Val Thr Val Ser Trp Asn Ser Gly Ala Leu
        435                 440                 445

Thr Ser Gly Val His Thr Phe Pro Ala Val Leu Gln Ser Ser Gly Leu
    450                 455                 460

Tyr Ser Leu Ser Ser Val Val Thr Val Pro Ser Ser Ser Leu Gly Thr
465                 470                 475                 480

Gln Thr Tyr Ile Cys Asn Val Asn His Lys Pro Ser Asn Thr Lys Val
                485                 490                 495

Asp Lys Lys Val Glu Pro Lys Ser Cys Asp Lys Thr His Thr Cys Pro
            500                 505                 510

Pro Cys Pro Ala Pro Glu Leu Leu Gly Gly Pro Ser Val Phe Leu Phe
        515                 520                 525

Pro Pro Lys Pro Lys Asp Thr Leu Met Ile Ser Arg Thr Pro Glu Val
    530                 535                 540
```

Thr Cys Val Val Val Asp Val Ser His Glu Asp Pro Glu Val Lys Phe
545 550 555 560

Asn Trp Tyr Val Asp Gly Val Glu Val His Asn Ala Lys Thr Lys Pro
565 570 575

Arg Glu Glu Gln Tyr Asn Ser Thr Tyr Arg Val Val Ser Val Leu Thr
580 585 590

Val Leu His Gln Asp Trp Leu Asn Gly Lys Glu Tyr Lys Cys Lys Val
595 600 605

Ser Asn Lys Ala Leu Pro Ala Pro Ile Glu Lys Thr Ile Ser Lys Ala
610 615 620

Lys Gly Gln Pro Arg Glu Pro Gln Val Tyr Thr Leu Pro Pro Cys Arg
625 630 635 640

Asp Glu Leu Thr Lys Asn Gln Val Ser Leu Trp Cys Leu Val Lys Gly
645 650 655

Phe Tyr Pro Ser Asp Ile Ala Val Glu Trp Glu Ser Asn Gly Gln Pro
660 665 670

Glu Asn Asn Tyr Lys Thr Thr Pro Pro Val Leu Asp Ser Asp Gly Ser
675 680 685

Phe Phe Leu Tyr Ser Lys Leu Thr Val Asp Lys Ser Arg Trp Gln Gln
690 695 700

Gly Asn Val Phe Ser Cys Ser Val Met His Glu Ala Leu His Asn His
705 710 715 720

Tyr Thr Gln Lys Ser Leu Ser Leu Ser Pro Gly Lys
725 730

<210> SEQ ID NO 6
<211> LENGTH: 755
<212> TYPE: PRT
<213> ORGANISM: Artificial Sequence
<220> FEATURE:
<223> OTHER INFORMATION: Light chain (Ipil)-sc36TMB linker Twin Strep tag-Heavy chain (Ipil)-Fc (Hole)

<400> SEQUENCE: 6

Met Gly Trp Ser Cys Ile Ile Leu Phe Leu Val Ala Thr Ala Thr Gly
1 5 10 15

Val His Ser Glu Ile Val Leu Thr Gln Ser Pro Gly Thr Leu Ser Leu
20 25 30

Ser Pro Gly Glu Arg Ala Thr Leu Ser Cys Arg Ala Ser Gln Ser Val
35 40 45

Gly Ser Ser Tyr Leu Ala Trp Tyr Gln Gln Lys Pro Gly Gln Ala Pro
50 55 60

Arg Leu Leu Ile Tyr Gly Ala Phe Ser Arg Ala Thr Gly Ile Pro Asp
65 70 75 80

Arg Phe Ser Gly Ser Gly Ser Gly Thr Asp Phe Thr Leu Thr Ile Ser
85 90 95

Arg Leu Glu Pro Glu Asp Phe Ala Val Tyr Tyr Cys Gln Gln Tyr Gly
100 105 110

Ser Ser Pro Trp Thr Phe Gly Gln Gly Thr Lys Val Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

-continued

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Leu Val Pro Arg Gly
225                 230                 235                 240

Ser Gly Ser Gly Gly Gly Ser Glu Gly Gly Gly Ser Glu Gly Gly Trp
                245                 250                 255

Ser His Pro Gln Phe Glu Lys Gly Gly Gly Ser Gly Gly Gly Ser Gly
            260                 265                 270

Gly Ser Ala Trp Ser His Pro Gln Phe Glu Lys Gly Ser Glu Gly Gly
        275                 280                 285

Gly Ser Glu Gly Gly Gly Ser Gly Gly Gly Ser Gly Gly Leu Val Pro
    290                 295                 300

Arg Gly Ser Gln Val Gln Leu Val Glu Ser Gly Gly Gly Val Val Gln
305                 310                 315                 320

Pro Gly Arg Ser Leu Arg Leu Ser Cys Ala Ala Ser Gly Phe Thr Phe
                325                 330                 335

Ser Ser Tyr Thr Met His Trp Val Arg Gln Ala Pro Gly Lys Gly Leu
            340                 345                 350

Glu Trp Val Thr Phe Ile Ser Tyr Asp Gly Asn Asn Lys Tyr Tyr Ala
        355                 360                 365

Asp Ser Val Lys Gly Arg Phe Thr Ile Ser Arg Asp Asn Ser Lys Asn
    370                 375                 380

Thr Leu Tyr Leu Gln Met Asn Ser Leu Arg Ala Glu Asp Thr Ala Ile
385                 390                 395                 400

Tyr Tyr Cys Ala Arg Thr Gly Trp Leu Gly Pro Phe Asp Tyr Trp Gly
                405                 410                 415

Gln Gly Thr Leu Val Thr Val Ser Ser Ala Ser Thr Lys Gly Pro Ser
            420                 425                 430

Val Phe Pro Leu Ala Pro Ser Ser Lys Ser Thr Ser Gly Gly Thr Ala
        435                 440                 445

Ala Leu Gly Cys Leu Val Lys Asp Tyr Phe Pro Glu Pro Val Thr Val
    450                 455                 460

Ser Trp Asn Ser Gly Ala Leu Thr Ser Gly Val His Thr Phe Pro Ala
465                 470                 475                 480

Val Leu Gln Ser Ser Gly Leu Tyr Ser Leu Ser Ser Val Val Thr Val
                485                 490                 495

Pro Ser Ser Ser Leu Gly Thr Gln Thr Tyr Ile Cys Asn Val Asn His
            500                 505                 510

Lys Pro Ser Asn Thr Lys Val Asp Lys Lys Val Glu Pro Lys Ser Cys
        515                 520                 525

Asp Lys Thr His Thr Cys Pro Pro Cys Pro Ala Pro Glu Leu Leu Gly
    530                 535                 540

Gly Pro Ser Val Phe Leu Phe Pro Pro Lys Pro Lys Asp Thr Leu Met
545                 550                 555                 560

Ile Ser Arg Thr Pro Glu Val Thr Cys Val Val Val Asp Val Ser His
                565                 570                 575

Glu Asp Pro Glu Val Lys Phe Asn Trp Tyr Val Asp Gly Val Glu Val
            580                 585                 590
```

```
His Asn Ala Lys Thr Lys Pro Arg Glu Glu Gln Tyr Asn Ser Thr Tyr
        595                 600                 605

Arg Val Val Ser Val Leu Thr Val Leu His Gln Asp Trp Leu Asn Gly
    610                 615                 620

Lys Glu Tyr Lys Cys Lys Val Ser Asn Lys Ala Leu Pro Ala Pro Ile
625                 630                 635                 640

Glu Lys Thr Ile Ser Lys Ala Lys Gly Gln Pro Arg Glu Pro Gln Val
                645                 650                 655

Cys Thr Leu Pro Pro Ser Arg Asp Glu Leu Thr Lys Asn Gln Val Ser
            660                 665                 670

Leu Ser Cys Ala Val Lys Gly Phe Tyr Pro Ser Asp Ile Ala Val Glu
        675                 680                 685

Trp Glu Ser Asn Gly Gln Pro Glu Asn Asn Tyr Lys Thr Thr Pro Pro
    690                 695                 700

Val Leu Asp Ser Asp Gly Ser Phe Phe Leu Val Ser Lys Leu Thr Val
705                 710                 715                 720

Asp Lys Ser Arg Trp Gln Gln Gly Asn Val Phe Ser Cys Ser Val Met
                725                 730                 735

His Glu Ala Leu His Asn His Tyr Thr Gln Lys Ser Leu Ser Leu Ser
            740                 745                 750

Pro Gly Lys
        755


<210> SEQ ID NO 7
<211> LENGTH: 736
<212> TYPE: PRT
<213> ORGANISM: Artificial Sequence
<220> FEATURE:
<223> OTHER INFORMATION: Light chain (Dara)-sc36TMB linker 10xHisTag-
      Heavy chain (Dara)-Fc (Knob)

<400> SEQUENCE: 7

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190
```

```
Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Leu Val Pro Arg Gly Ser
225                 230                 235                 240

Gly Ser Gly Gly Gly Ser Gly Gly Gly Ser His His His His His His
                245                 250                 255

His His His His Gly Gly Gly Ser Gly Gly Gly Ser Gly Gly Gly Ser
            260                 265                 270

Gly Gly Gly Ser Gly Gly Leu Val Pro Arg Gly Ser Glu Val Gln Leu
        275                 280                 285

Leu Glu Ser Gly Gly Gly Leu Val Gln Pro Gly Gly Ser Leu Arg Leu
    290                 295                 300

Ser Cys Ala Val Ser Gly Phe Thr Phe Asn Ser Phe Ala Met Ser Trp
305                 310                 315                 320

Val Arg Gln Ala Pro Gly Lys Gly Leu Glu Trp Val Ser Ala Ile Ser
                325                 330                 335

Gly Ser Gly Gly Gly Thr Tyr Tyr Ala Asp Ser Val Lys Gly Arg Phe
            340                 345                 350

Thr Ile Ser Arg Asp Asn Ser Lys Asn Thr Leu Tyr Leu Gln Met Asn
        355                 360                 365

Ser Leu Arg Ala Glu Asp Thr Ala Val Tyr Phe Cys Ala Lys Asp Lys
    370                 375                 380

Ile Leu Trp Phe Gly Glu Pro Val Phe Asp Tyr Trp Gly Gln Gly Thr
385                 390                 395                 400

Leu Val Thr Val Ser Ser Ala Ser Thr Lys Gly Pro Ser Val Phe Pro
                405                 410                 415

Leu Ala Pro Ser Ser Lys Ser Thr Ser Gly Gly Thr Ala Ala Leu Gly
            420                 425                 430

Cys Leu Val Lys Asp Tyr Phe Pro Glu Pro Val Thr Val Ser Trp Asn
        435                 440                 445

Ser Gly Ala Leu Thr Ser Gly Val His Thr Phe Pro Ala Val Leu Gln
    450                 455                 460

Ser Ser Gly Leu Tyr Ser Leu Ser Ser Val Val Thr Val Pro Ser Ser
465                 470                 475                 480

Ser Leu Gly Thr Gln Thr Tyr Ile Cys Asn Val Asn His Lys Pro Ser
                485                 490                 495

Asn Thr Lys Val Asp Lys Lys Val Glu Pro Lys Ser Cys Asp Lys Thr
            500                 505                 510

His Thr Cys Pro Pro Cys Pro Ala Pro Glu Leu Leu Gly Gly Pro Ser
        515                 520                 525

Val Phe Leu Phe Pro Pro Lys Pro Lys Asp Thr Leu Met Ile Ser Arg
    530                 535                 540

Thr Pro Glu Val Thr Cys Val Val Val Asp Val Ser His Glu Asp Pro
545                 550                 555                 560

Glu Val Lys Phe Asn Trp Tyr Val Asp Gly Val Glu Val His Asn Ala
                565                 570                 575

Lys Thr Lys Pro Arg Glu Glu Gln Tyr Asn Ser Thr Tyr Arg Val Val
            580                 585                 590

Ser Val Leu Thr Val Leu His Gln Asp Trp Leu Asn Gly Lys Glu Tyr
        595                 600                 605
```

Lys Cys Lys Val Ser Asn Lys Ala Leu Pro Ala Pro Ile Glu Lys Thr
610 615 620

Ile Ser Lys Ala Lys Gly Gln Pro Arg Glu Pro Gln Val Tyr Thr Leu
625 630 635 640

Pro Pro Cys Arg Asp Glu Leu Thr Lys Asn Gln Val Ser Leu Trp Cys
645 650 655

Leu Val Lys Gly Phe Tyr Pro Ser Asp Ile Ala Val Glu Trp Glu Ser
660 665 670

Asn Gly Gln Pro Glu Asn Asn Tyr Lys Thr Thr Pro Pro Val Leu Asp
675 680 685

Ser Asp Gly Ser Phe Phe Leu Tyr Ser Lys Leu Thr Val Asp Lys Ser
690 695 700

Arg Trp Gln Gln Gly Asn Val Phe Ser Cys Ser Val Met His Glu Ala
705 710 715 720

Leu His Asn His Tyr Thr Gln Lys Ser Leu Ser Leu Ser Pro Gly Lys
725 730 735

<210> SEQ ID NO 8
<211> LENGTH: 734
<212> TYPE: PRT
<213> ORGANISM: Artificial Sequence
<220> FEATURE:
<223> OTHER INFORMATION: Light chain (Her)-sc36TMB linker 10xHisTag-
Heavy chain (Her)-Fc region (Knob)

<400> SEQUENCE: 8

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Arg Ala Ser Gln Asp Val
35 40 45

Asn Thr Ala Val Ala Trp Tyr Gln Gln Lys Pro Gly Lys Ala Pro Lys
50 55 60

Leu Leu Ile Tyr Ser Ala Ser Phe Leu Tyr Ser Gly Val Pro Ser Arg
65 70 75 80

Phe Ser Gly Ser Arg Ser Gly Thr Asp Phe Thr Leu Thr Ile Ser Ser
85 90 95

Leu Gln Pro Glu Asp Phe Ala Thr Tyr Tyr Cys Gln Gln His Tyr Thr
100 105 110

Thr Pro Pro Thr Phe Gly Gln Gly Thr Lys Val Glu Ile Lys Arg Thr
115 120 125

Val Ala Ala Pro Ser Val Phe Ile Phe Pro Pro Ser Asp Glu Gln Leu
130 135 140

Lys Ser Gly Thr Ala Ser Val Val Cys Leu Leu Asn Asn Phe Tyr Pro
145 150 155 160

Arg Glu Ala Lys Val Gln Trp Lys Val Asp Asn Ala Leu Gln Ser Gly
165 170 175

Asn Ser Gln Glu Ser Val Thr Glu Gln Asp Ser Lys Asp Ser Thr Tyr
180 185 190

Ser Leu Ser Ser Thr Leu Thr Leu Ser Lys Ala Asp Tyr Glu Lys His
195 200 205

Lys Val Tyr Ala Cys Glu Val Thr His Gln Gly Leu Ser Ser Pro Val
210 215 220

Thr Lys Ser Phe Asn Arg Gly Glu Cys Gly Leu Val Pro Arg Gly Ser
225 230 235 240

```
Gly Ser Gly Gly Gly Ser Gly Gly Gly Ser His His His His His His
                245                 250                 255

His His His His Gly Gly Gly Ser Gly Gly Gly Ser Gly Gly Gly Ser
            260                 265                 270

Gly Gly Gly Ser Gly Gly Leu Val Pro Arg Gly Ser Glu Val Gln Leu
        275                 280                 285

Val Glu Ser Gly Gly Gly Leu Val Gln Pro Gly Gly Ser Leu Arg Leu
    290                 295                 300

Ser Cys Ala Ala Ser Gly Phe Asn Ile Lys Asp Thr Tyr Ile His Trp
305                 310                 315                 320

Val Arg Gln Ala Pro Gly Lys Gly Leu Glu Trp Val Ala Arg Ile Tyr
                325                 330                 335

Pro Thr Asn Gly Tyr Thr Arg Tyr Ala Asp Ser Val Lys Gly Arg Phe
            340                 345                 350

Thr Ile Ser Ala Asp Thr Ser Lys Asn Thr Ala Tyr Leu Gln Met Asn
        355                 360                 365

Ser Leu Arg Ala Glu Asp Thr Ala Val Tyr Tyr Cys Ser Arg Trp Gly
    370                 375                 380

Gly Asp Gly Phe Tyr Ala Met Asp Tyr Trp Gly Gln Gly Thr Leu Val
385                 390                 395                 400

Thr Val Ser Ser Ala Ser Thr Lys Gly Pro Ser Val Phe Pro Leu Ala
                405                 410                 415

Pro Ser Ser Lys Ser Thr Ser Gly Gly Thr Ala Ala Leu Gly Cys Leu
            420                 425                 430

Val Lys Asp Tyr Phe Pro Glu Pro Val Thr Val Ser Trp Asn Ser Gly
        435                 440                 445

Ala Leu Thr Ser Gly Val His Thr Phe Pro Ala Val Leu Gln Ser Ser
    450                 455                 460

Gly Leu Tyr Ser Leu Ser Ser Val Val Thr Val Pro Ser Ser Ser Leu
465                 470                 475                 480

Gly Thr Gln Thr Tyr Ile Cys Asn Val Asn His Lys Pro Ser Asn Thr
                485                 490                 495

Lys Val Asp Lys Lys Val Glu Pro Lys Ser Cys Asp Lys Thr His Thr
            500                 505                 510

Cys Pro Pro Cys Pro Ala Pro Glu Leu Leu Gly Gly Pro Ser Val Phe
        515                 520                 525

Leu Phe Pro Pro Lys Pro Lys Asp Thr Leu Met Ile Ser Arg Thr Pro
    530                 535                 540

Glu Val Thr Cys Val Val Val Asp Val Ser His Glu Asp Pro Glu Val
545                 550                 555                 560

Lys Phe Asn Trp Tyr Val Asp Gly Val Glu Val His Asn Ala Lys Thr
                565                 570                 575

Lys Pro Arg Glu Glu Gln Tyr Asn Ser Thr Tyr Arg Val Val Ser Val
            580                 585                 590

Leu Thr Val Leu His Gln Asp Trp Leu Asn Gly Lys Glu Tyr Lys Cys
        595                 600                 605

Lys Val Ser Asn Lys Ala Leu Pro Ala Pro Ile Glu Lys Thr Ile Ser
    610                 615                 620

Lys Ala Lys Gly Gln Pro Arg Glu Pro Gln Val Tyr Thr Leu Pro Pro
625                 630                 635                 640

Cys Arg Asp Glu Leu Thr Lys Asn Gln Val Ser Leu Trp Cys Leu Val
                645                 650                 655
```

Lys Gly Phe Tyr Pro Ser Asp Ile Ala Val Glu Trp Glu Ser Asn Gly
660 665 670

Gln Pro Glu Asn Asn Tyr Lys Thr Thr Pro Pro Val Leu Asp Ser Asp
675 680 685

Gly Ser Phe Phe Leu Tyr Ser Lys Leu Thr Val Asp Lys Ser Arg Trp
690 695 700

Gln Gln Gly Asn Val Phe Ser Cys Ser Val Met His Glu Ala Leu His
705 710 715 720

Asn His Tyr Thr Gln Lys Ser Leu Ser Leu Ser Pro Gly Lys
725 730

<210> SEQ ID NO 9
<211> LENGTH: 1227
<212> TYPE: PRT
<213> ORGANISM: Artificial Sequence
<220> FEATURE:
<223> OTHER INFORMATION: Light chain (Her)-sc36TMB linker-heavy chain(Her)-N-linker-Light chain (Ipil)-sc36TMB linker-Heavy chain (Ipil)-Fc region (Hole)

<400> SEQUENCE: 9

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Arg Ala Ser Gln Asp Val
35 40 45

Asn Thr Ala Val Ala Trp Tyr Gln Gln Lys Pro Gly Lys Ala Pro Lys
50 55 60

Leu Leu Ile Tyr Ser Ala Ser Phe Leu Tyr Ser Gly Val Pro Ser Arg
65 70 75 80

Phe Ser Gly Ser Arg Ser Gly Thr Asp Phe Thr Leu Thr Ile Ser Ser
85 90 95

Leu Gln Pro Glu Asp Phe Ala Thr Tyr Tyr Cys Gln Gln His Tyr Thr
100 105 110

Thr Pro Pro Thr Phe Gly Gln Gly Thr Lys Val Glu Ile Lys Arg Thr
115 120 125

Val Ala Ala Pro Ser Val Phe Ile Phe Pro Pro Ser Asp Glu Gln Leu
130 135 140

Lys Ser Gly Thr Ala Ser Val Val Cys Leu Leu Asn Asn Phe Tyr Pro
145 150 155 160

Arg Glu Ala Lys Val Gln Trp Lys Val Asp Asn Ala Leu Gln Ser Gly
165 170 175

Asn Ser Gln Glu Ser Val Thr Glu Gln Asp Ser Lys Asp Ser Thr Tyr
180 185 190

Ser Leu Ser Ser Thr Leu Thr Leu Ser Lys Ala Asp Tyr Glu Lys His
195 200 205

Lys Val Tyr Ala Cys Glu Val Thr His Gln Gly Leu Ser Ser Pro Val
210 215 220

Thr Lys Ser Phe Asn Arg Gly Glu Cys Gly Leu Val Pro Arg Gly Ser
225 230 235 240

Gly Ser Gly Gly Gly Ser Gly Gly Gly Ser Glu Gly Gly Gly Ser Glu
245 250 255

Gly Gly Gly Ser Glu Gly Gly Gly Ser Glu Gly Gly Gly Ser Gly Gly
260 265 270

Gly Ser Gly Gly Leu Val Pro Arg Gly Ser Glu Val Gln Leu Val Glu

-continued

```
        275                 280                 285

Ser Gly Gly Gly Leu Val Gln Pro Gly Gly Ser Leu Arg Leu Ser Cys
    290                 295                 300

Ala Ala Ser Gly Phe Asn Ile Lys Asp Thr Tyr Ile His Trp Val Arg
305                 310                 315                 320

Gln Ala Pro Gly Lys Gly Leu Glu Trp Val Ala Arg Ile Tyr Pro Thr
                325                 330                 335

Asn Gly Tyr Thr Arg Tyr Ala Asp Ser Val Lys Gly Arg Phe Thr Ile
            340                 345                 350

Ser Ala Asp Thr Ser Lys Asn Thr Ala Tyr Leu Gln Met Asn Ser Leu
        355                 360                 365

Arg Ala Glu Asp Thr Ala Val Tyr Tyr Cys Ser Arg Trp Gly Gly Asp
    370                 375                 380

Gly Phe Tyr Ala Met Asp Tyr Trp Gly Gln Gly Thr Leu Val Thr Val
385                 390                 395                 400

Ser Ser Ala Ser Thr Lys Gly Pro Ser Val Phe Pro Leu Ala Pro Ser
                405                 410                 415

Ser Lys Ser Thr Ser Gly Gly Thr Ala Ala Leu Gly Cys Leu Val Lys
            420                 425                 430

Asp Tyr Phe Pro Glu Pro Val Thr Val Ser Trp Asn Ser Gly Ala Leu
        435                 440                 445

Thr Ser Gly Val His Thr Phe Pro Ala Val Leu Gln Ser Ser Gly Leu
    450                 455                 460

Tyr Ser Leu Ser Ser Val Val Thr Val Pro Ser Ser Ser Leu Gly Thr
465                 470                 475                 480

Gln Thr Tyr Ile Cys Asn Val Asn His Lys Pro Ser Asn Thr Lys Val
                485                 490                 495

Asp Lys Lys Val Glu Pro Lys Ser Cys Ala Ser Thr Lys Gly Pro Ser
            500                 505                 510

Gly Ser Gly Glu Ile Val Leu Thr Gln Ser Pro Gly Thr Leu Ser Leu
        515                 520                 525

Ser Pro Gly Glu Arg Ala Thr Leu Ser Cys Arg Ala Ser Gln Ser Val
    530                 535                 540

Gly Ser Ser Tyr Leu Ala Trp Tyr Gln Gln Lys Pro Gly Gln Ala Pro
545                 550                 555                 560

Arg Leu Leu Ile Tyr Gly Ala Phe Ser Arg Ala Thr Gly Ile Pro Asp
                565                 570                 575

Arg Phe Ser Gly Ser Gly Ser Gly Thr Asp Phe Thr Leu Thr Ile Ser
            580                 585                 590

Arg Leu Glu Pro Glu Asp Phe Ala Val Tyr Tyr Cys Gln Gln Tyr Gly
        595                 600                 605

Ser Ser Pro Trp Thr Phe Gly Gln Gly Thr Lys Val Glu Ile Lys Arg
    610                 615                 620

Thr Val Ala Ala Pro Ser Val Phe Ile Phe Pro Pro Ser Asp Glu Gln
625                 630                 635                 640

Leu Lys Ser Gly Thr Ala Ser Val Val Cys Leu Leu Asn Asn Phe Tyr
                645                 650                 655

Pro Arg Glu Ala Lys Val Gln Trp Lys Val Asp Asn Ala Leu Gln Ser
            660                 665                 670

Gly Asn Ser Gln Glu Ser Val Thr Glu Gln Asp Ser Lys Asp Ser Thr
        675                 680                 685

Tyr Ser Leu Ser Ser Thr Leu Thr Leu Ser Lys Ala Asp Tyr Glu Lys
    690                 695                 700
```

His Lys Val Tyr Ala Cys Glu Val Thr His Gln Gly Leu Ser Ser Pro
705 710 715 720

Val Thr Lys Ser Phe Asn Arg Gly Glu Cys Gly Leu Val Pro Arg Gly
725 730 735

Ser Gly Ser Gly Gly Gly Ser Gly Gly Gly Ser Glu Gly Gly Gly Ser
740 745 750

Glu Gly Gly Gly Ser Glu Gly Gly Gly Ser Glu Gly Gly Gly Ser Gly
755 760 765

Gly Gly Ser Gly Gly Leu Val Pro Arg Gly Ser Gln Val Gln Leu Val
770 775 780

Glu Ser Gly Gly Gly Val Val Gln Pro Gly Arg Ser Leu Arg Leu Ser
785 790 795 800

Cys Ala Ala Ser Gly Phe Thr Phe Ser Ser Tyr Thr Met His Trp Val
805 810 815

Arg Gln Ala Pro Gly Lys Gly Leu Glu Trp Val Thr Phe Ile Ser Tyr
820 825 830

Asp Gly Asn Asn Lys Tyr Tyr Ala Asp Ser Val Lys Gly Arg Phe Thr
835 840 845

Ile Ser Arg Asp Asn Ser Lys Asn Thr Leu Tyr Leu Gln Met Asn Ser
850 855 860

Leu Arg Ala Glu Asp Thr Ala Ile Tyr Tyr Cys Ala Arg Thr Gly Trp
865 870 875 880

Leu Gly Pro Phe Asp Tyr Trp Gly Gln Gly Thr Leu Val Thr Val Ser
885 890 895

Ser Ala Ser Thr Lys Gly Pro Ser Val Phe Pro Leu Ala Pro Ser Ser
900 905 910

Lys Ser Thr Ser Gly Gly Thr Ala Ala Leu Gly Cys Leu Val Lys Asp
915 920 925

Tyr Phe Pro Glu Pro Val Thr Val Ser Trp Asn Ser Gly Ala Leu Thr
930 935 940

Ser Gly Val His Thr Phe Pro Ala Val Leu Gln Ser Ser Gly Leu Tyr
945 950 955 960

Ser Leu Ser Ser Val Val Thr Val Pro Ser Ser Ser Leu Gly Thr Gln
965 970 975

Thr Tyr Ile Cys Asn Val Asn His Lys Pro Ser Asn Thr Lys Val Asp
980 985 990

Lys Lys Val Glu Pro Lys Ser Cys Asp Lys Thr His Thr Cys Pro Pro
995 1000 1005

Cys Pro Ala Pro Glu Leu Leu Gly Gly Pro Ser Val Phe Leu Phe
1010 1015 1020

Pro Pro Lys Pro Lys Asp Thr Leu Met Ile Ser Arg Thr Pro Glu
1025 1030 1035

Val Thr Cys Val Val Val Asp Val Ser His Glu Asp Pro Glu Val
1040 1045 1050

Lys Phe Asn Trp Tyr Val Asp Gly Val Glu Val His Asn Ala Lys
1055 1060 1065

Thr Lys Pro Arg Glu Glu Gln Tyr Asn Ser Thr Tyr Arg Val Val
1070 1075 1080

Ser Val Leu Thr Val Leu His Gln Asp Trp Leu Asn Gly Lys Glu
1085 1090 1095

Tyr Lys Cys Lys Val Ser Asn Lys Ala Leu Pro Ala Pro Ile Glu
1100 1105 1110

Lys Thr Ile Ser Lys Ala Lys Gly Gln Pro Arg Glu Pro Gln Val
1115 1120 1125

Cys Thr Leu Pro Pro Ser Arg Asp Glu Leu Thr Lys Asn Gln Val
1130 1135 1140

Ser Leu Ser Cys Ala Val Lys Gly Phe Tyr Pro Ser Asp Ile Ala
1145 1150 1155

Val Glu Trp Glu Ser Asn Gly Gln Pro Glu Asn Asn Tyr Lys Thr
1160 1165 1170

Thr Pro Pro Val Leu Asp Ser Asp Gly Ser Phe Phe Leu Val Ser
1175 1180 1185

Lys Leu Thr Val Asp Lys Ser Arg Trp Gln Gln Gly Asn Val Phe
1190 1195 1200

Ser Cys Ser Val Met His Glu Ala Leu His Asn His Tyr Thr Gln
1205 1210 1215

Lys Ser Leu Ser Leu Ser Pro Gly Lys
1220 1225

<210> SEQ ID NO 10
<211> LENGTH: 1228
<212> TYPE: PRT
<213> ORGANISM: Artificial Sequence
<220> FEATURE:
<223> OTHER INFORMATION: Light chain (Atez)-sc36TMB linker-heavy chain(Atez)-N-linker-Light chain (Dara)-sc36TMB linker-Heavy chain (dara)-Fc region (Knob)

<400> SEQUENCE: 10

Met Gly Trp Ser Cys Ile Ile Leu Phe Leu Val Ala Thr Ala Thr Gly
1 5 10 15

Val His Ser Asp Ile Gln Met Thr Gln Ser Pro Ser Ser Leu Ser Ala
20 25 30

Ser Val Gly Asp Arg Val Thr Ile Thr Cys Arg Ala Ser Gln Asp Val
35 40 45

Ser Thr Ala Val Ala Trp Tyr Gln Gln Lys Pro Gly Lys Ala Pro Lys
50 55 60

Leu Leu Ile Tyr Ser Ala Ser Phe Leu Tyr Ser Gly Val Pro Ser Arg
65 70 75 80

Phe Ser Gly Ser Gly Ser Gly Thr Asp Phe Thr Leu Thr Ile Ser Ser
85 90 95

Leu Gln Pro Glu Asp Phe Ala Thr Tyr Tyr Cys Gln Gln Tyr Leu Tyr
100 105 110

His Pro Ala Thr Phe Gly Gln Gly Thr Lys Val Glu Ile Lys Arg Thr
115 120 125

Val Ala Ala Pro Ser Val Phe Ile Phe Pro Pro Ser Asp Glu Gln Leu
130 135 140

Lys Ser Gly Thr Ala Ser Val Val Cys Leu Leu Asn Asn Phe Tyr Pro
145 150 155 160

Arg Glu Ala Lys Val Gln Trp Lys Val Asp Asn Ala Leu Gln Ser Gly
165 170 175

Asn Ser Gln Glu Ser Val Thr Glu Gln Asp Ser Lys Asp Ser Thr Tyr
180 185 190

Ser Leu Ser Ser Thr Leu Thr Leu Ser Lys Ala Asp Tyr Glu Lys His
195 200 205

Lys Val Tyr Ala Cys Glu Val Thr His Gln Gly Leu Ser Ser Pro Val
210 215 220

Thr Lys Ser Phe Asn Arg Gly Glu Cys Gly Leu Val Pro Arg Gly Ser

```
225                 230                 235                 240

Gly Ser Gly Gly Gly Ser Gly Gly Gly Ser Glu Gly Gly Gly Ser Glu
                245                 250                 255

Gly Gly Gly Ser Glu Gly Gly Gly Ser Glu Gly Gly Gly Ser Gly Gly
            260                 265                 270

Gly Ser Gly Gly Leu Val Pro Arg Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Phe Thr Phe Ser Asp Ser Trp Ile His Trp Val Arg
305                 310                 315                 320

Gln Ala Pro Gly Lys Gly Leu Glu Trp Val Ala Trp Ile Ser Pro Tyr
                325                 330                 335

Gly Gly Ser Thr Tyr Tyr Ala Asp Ser Val Lys Gly Arg Phe Thr Ile
            340                 345                 350

Ser Ala Asp Thr Ser Lys Asn Thr Ala Tyr Leu Gln Met Asn Ser Leu
        355                 360                 365

Arg Ala Glu Asp Thr Ala Val Tyr Tyr Cys Ala Arg Arg His Trp Pro
    370                 375                 380

Gly Gly Phe Asp Tyr Trp Gly Gln Gly Thr Leu Val Thr Val Ser Ser
385                 390                 395                 400

Ala Ser Thr Lys Gly Pro Ser Val Phe Pro Leu Ala Pro Ser Ser Lys
                405                 410                 415

Ser Thr Ser Gly Gly Thr Ala Ala Leu Gly Cys Leu Val Lys Asp Tyr
            420                 425                 430

Phe Pro Glu Pro Val Thr Val Ser Trp Asn Ser Gly Ala Leu Thr Ser
        435                 440                 445

Gly Val His Thr Phe Pro Ala Val Leu Gln Ser Ser Gly Leu Tyr Ser
    450                 455                 460

Leu Ser Ser Val Val Thr Val Pro Ser Ser Ser Leu Gly Thr Gln Thr
465                 470                 475                 480

Tyr Ile Cys Asn Val Asn His Lys Pro Ser Asn Thr Lys Val Asp Lys
                485                 490                 495

Lys Val Glu Pro Lys Ser Cys Ala Ser Thr Lys Gly Pro Ser Gly Ser
            500                 505                 510

Gly Glu Ile Val Leu Thr Gln Ser Pro Ala Thr Leu Ser Leu Ser Pro
        515                 520                 525

Gly Glu Arg Ala Thr Leu Ser Cys Arg Ala Ser Gln Ser Val Ser Ser
    530                 535                 540

Tyr Leu Ala Trp Tyr Gln Gln Lys Pro Gly Gln Ala Pro Arg Leu Leu
545                 550                 555                 560

Ile Tyr Asp Ala Ser Asn Arg Ala Thr Gly Ile Pro Ala Arg Phe Ser
                565                 570                 575

Gly Ser Gly Ser Gly Thr Asp Phe Thr Leu Thr Ile Ser Ser Leu Glu
            580                 585                 590

Pro Glu Asp Phe Ala Val Tyr Tyr Cys Gln Gln Arg Ser Asn Trp Pro
        595                 600                 605

Pro Thr Phe Gly Gln Gly Thr Lys Val Glu Ile Lys Arg Thr Val Ala
    610                 615                 620

Ala Pro Ser Val Phe Ile Phe Pro Pro Ser Asp Glu Gln Leu Lys Ser
625                 630                 635                 640

Gly Thr Ala Ser Val Val Cys Leu Leu Asn Asn Phe Tyr Pro Arg Glu
                645                 650                 655
```

```
Ala Lys Val Gln Trp Lys Val Asp Asn Ala Leu Gln Ser Gly Asn Ser
            660                 665                 670

Gln Glu Ser Val Thr Glu Gln Asp Ser Lys Asp Ser Thr Tyr Ser Leu
        675                 680                 685

Ser Ser Thr Leu Thr Leu Ser Lys Ala Asp Tyr Glu Lys His Lys Val
    690                 695                 700

Tyr Ala Cys Glu Val Thr His Gln Gly Leu Ser Ser Pro Val Thr Lys
705                 710                 715                 720

Ser Phe Asn Arg Gly Glu Cys Gly Leu Val Pro Arg Gly Ser Gly Ser
                725                 730                 735

Gly Gly Gly Ser Gly Gly Gly Ser Glu Gly Gly Gly Ser Glu Gly Gly
            740                 745                 750

Gly Ser Glu Gly Gly Gly Ser Glu Gly Gly Gly Ser Gly Gly Gly Ser
        755                 760                 765

Gly Gly Leu Val Pro Arg Gly Ser Glu Val Gln Leu Leu Glu Ser Gly
    770                 775                 780

Gly Gly Leu Val Gln Pro Gly Gly Ser Leu Arg Leu Ser Cys Ala Val
785                 790                 795                 800

Ser Gly Phe Thr Phe Asn Ser Phe Ala Met Ser Trp Val Arg Gln Ala
                805                 810                 815

Pro Gly Lys Gly Leu Glu Trp Val Ser Ala Ile Ser Gly Ser Gly Gly
            820                 825                 830

Gly Thr Tyr Tyr Ala Asp Ser Val Lys Gly Arg Phe Thr Ile Ser Arg
        835                 840                 845

Asp Asn Ser Lys Asn Thr Leu Tyr Leu Gln Met Asn Ser Leu Arg Ala
    850                 855                 860

Glu Asp Thr Ala Val Tyr Phe Cys Ala Lys Asp Lys Ile Leu Trp Phe
865                 870                 875                 880

Gly Glu Pro Val Phe Asp Tyr Trp Gly Gln Gly Thr Leu Val Thr Val
                885                 890                 895

Ser Ser Ala Ser Thr Lys Gly Pro Ser Val Phe Pro Leu Ala Pro Ser
            900                 905                 910

Ser Lys Ser Thr Ser Gly Gly Thr Ala Ala Leu Gly Cys Leu Val Lys
        915                 920                 925

Asp Tyr Phe Pro Glu Pro Val Thr Val Ser Trp Asn Ser Gly Ala Leu
    930                 935                 940

Thr Ser Gly Val His Thr Phe Pro Ala Val Leu Gln Ser Ser Gly Leu
945                 950                 955                 960

Tyr Ser Leu Ser Ser Val Val Thr Val Pro Ser Ser Ser Leu Gly Thr
                965                 970                 975

Gln Thr Tyr Ile Cys Asn Val Asn His Lys Pro Ser Asn Thr Lys Val
            980                 985                 990

Asp Lys Lys Val Glu Pro Lys Ser  Cys Asp Lys Thr His  Thr Cys Pro
        995                 1000                1005

Pro Cys  Pro Ala Pro Glu Leu  Leu Gly Gly Pro Ser  Val Phe Leu
    1010                1015                1020

Phe Pro  Pro Lys Pro Lys Asp  Thr Leu Met Ile Ser  Arg Thr Pro
    1025                1030                1035

Glu Val  Thr Cys Val Val Val  Asp Val Ser His Glu  Asp Pro Glu
    1040                1045                1050

Val Lys  Phe Asn Trp Tyr Val  Asp Gly Val Glu Val  His Asn Ala
    1055                1060                1065
```

```
Lys Thr  Lys Pro Arg Glu Glu  Gln Tyr Asn Ser Thr  Tyr Arg Val
    1070                 1075                 1080

Val Ser  Val Leu Thr Val Leu  His Gln Asp Trp Leu  Asn Gly Lys
    1085                 1090                 1095

Glu Tyr  Lys Cys Lys Val Ser  Asn Lys Ala Leu Pro  Ala Pro Ile
    1100                 1105                 1110

Glu Lys  Thr Ile Ser Lys Ala  Lys Gly Gln Pro Arg  Glu Pro Gln
    1115                 1120                 1125

Val Tyr  Thr Leu Pro Pro Cys  Arg Asp Glu Leu Thr  Lys Asn Gln
    1130                 1135                 1140

Val Ser  Leu Trp Cys Leu Val  Lys Gly Phe Tyr Pro  Ser Asp Ile
    1145                 1150                 1155

Ala Val  Glu Trp Glu Ser Asn  Gly Gln Pro Glu Asn  Asn Tyr Lys
    1160                 1165                 1170

Thr Thr  Pro Pro Val Leu Asp  Ser Asp Gly Ser Phe  Phe Leu Tyr
    1175                 1180                 1185

Ser Lys  Leu Thr Val Asp Lys  Ser Arg Trp Gln Gln  Gly Asn Val
    1190                 1195                 1200

Phe Ser  Cys Ser Val Met His  Glu Ala Leu His Asn  His Tyr Thr
    1205                 1210                 1215

Gln Lys  Ser Leu Ser Leu Ser  Pro Gly Lys
    1220                 1225


<210> SEQ ID NO 11
<211> LENGTH: 1230
<212> TYPE: PRT
<213> ORGANISM: Artificial Sequence
<220> FEATURE:
<223> OTHER INFORMATION: Light chain (Ipil)-sc36TMB linker-heavychain
      (ipil)-Fc region (Hole)-C-linker- Light chain (Her)-sc36TMB
      linker-Heavy chain (Her)

<400> SEQUENCE: 11

Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Gly Ser Ser Tyr Leu Ala Trp Tyr Gln Gln Lys Pro Gly Gln Ala Pro
    50                  55                  60

Arg Leu Leu Ile Tyr Gly Ala Phe Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Ser Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
```

-continued

```
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Leu Val Pro Arg Gly
225                 230                 235                 240

Ser Gly Ser Gly Gly Gly Ser Gly Gly Gly Ser Glu Gly Gly Gly Ser
                245                 250                 255

Glu Gly Gly Gly Ser Glu Gly Gly Gly Ser Glu Gly Gly Gly Ser Gly
            260                 265                 270

Gly Gly Ser Gly Gly Leu Val Pro Arg Gly Ser Gln Val Gln Leu Val
        275                 280                 285

Glu Ser Gly Gly Gly Val Val Gln Pro Gly Arg Ser Leu Arg Leu Ser
    290                 295                 300

Cys Ala Ala Ser Gly Phe Thr Phe Ser Ser Tyr Thr Met His Trp Val
305                 310                 315                 320

Arg Gln Ala Pro Gly Lys Gly Leu Glu Trp Val Thr Phe Ile Ser Tyr
                325                 330                 335

Asp Gly Asn Asn Lys Tyr Tyr Ala Asp Ser Val Lys Gly Arg Phe Thr
            340                 345                 350

Ile Ser Arg Asp Asn Ser Lys Asn Thr Leu Tyr Leu Gln Met Asn Ser
        355                 360                 365

Leu Arg Ala Glu Asp Thr Ala Ile Tyr Tyr Cys Ala Arg Thr Gly Trp
    370                 375                 380

Leu Gly Pro Phe Asp Tyr Trp Gly Gln Gly Thr Leu Val Thr Val Ser
385                 390                 395                 400

Ser Ala Ser Thr Lys Gly Pro Ser Val Phe Pro Leu Ala Pro Ser Ser
                405                 410                 415

Lys Ser Thr Ser Gly Gly Thr Ala Ala Leu Gly Cys Leu Val Lys Asp
            420                 425                 430

Tyr Phe Pro Glu Pro Val Thr Val Ser Trp Asn Ser Gly Ala Leu Thr
        435                 440                 445

Ser Gly Val His Thr Phe Pro Ala Val Leu Gln Ser Ser Gly Leu Tyr
    450                 455                 460

Ser Leu Ser Ser Val Val Thr Val Pro Ser Ser Ser Leu Gly Thr Gln
465                 470                 475                 480

Thr Tyr Ile Cys Asn Val Asn His Lys Pro Ser Asn Thr Lys Val Asp
                485                 490                 495

Lys Lys Val Glu Pro Lys Ser Cys Asp Lys Thr His Thr Cys Pro Pro
            500                 505                 510

Cys Pro Ala Pro Glu Leu Leu Gly Gly Pro Ser Val Phe Leu Phe Pro
        515                 520                 525

Pro Lys Pro Lys Asp Thr Leu Met Ile Ser Arg Thr Pro Glu Val Thr
    530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Asn Ser Thr Tyr Arg Val Val Ser Val Leu Thr Val
            580                 585                 590

Leu His Gln Asp Trp Leu Asn Gly Lys Glu Tyr Lys Cys Lys Val Ser
        595                 600                 605
```

```
Asn Lys Ala Leu Pro Ala Pro Ile Glu Lys Thr Ile Ser Lys Ala Lys
    610                 615                 620

Gly Gln Pro Arg Glu Pro Gln Val Cys Thr Leu Pro Pro Ser Arg Asp
625                 630                 635                 640

Glu Leu Thr Lys Asn Gln Val Ser Leu Ser Cys Ala Val Lys Gly Phe
                645                 650                 655

Tyr Pro Ser Asp Ile Ala Val Glu Trp Glu Ser Asn Gly Gln Pro Glu
            660                 665                 670

Asn Asn Tyr Lys Thr Thr Pro Pro Val Leu Asp Ser Asp Gly Ser Phe
        675                 680                 685

Phe Leu Val Ser Lys Leu Thr Val Asp Lys Ser Arg Trp Gln Gln Gly
    690                 695                 700

Asn Val Phe Ser Cys Ser Val Met His Glu Ala Leu His Asn His Tyr
705                 710                 715                 720

Thr Gln Lys Ser Leu Ser Leu Ser Pro Gly Lys Gly Gly Gly Ser Gly
                725                 730                 735

Gly Gly Ser Gly Gly Gly Ser Gly Asp Ile Gln Met Thr Gln Ser Pro
            740                 745                 750

Ser Ser Leu Ser Ala Ser Val Gly Asp Arg Val Thr Ile Thr Cys Arg
        755                 760                 765

Ala Ser Gln Asp Val Asn Thr Ala Val Ala Trp Tyr Gln Gln Lys Pro
    770                 775                 780

Gly Lys Ala Pro Lys Leu Leu Ile Tyr Ser Ala Ser Phe Leu Tyr Ser
785                 790                 795                 800

Gly Val Pro Ser Arg Phe Ser Gly Ser Arg Ser Gly Thr Asp Phe Thr
                805                 810                 815

Leu Thr Ile Ser Ser Leu Gln Pro Glu Asp Phe Ala Thr Tyr Tyr Cys
            820                 825                 830

Gln Gln His Tyr Thr Thr Pro Pro Thr Phe Gly Gln Gly Thr Lys Val
        835                 840                 845

Glu Ile Lys Arg Thr Val Ala Ala Pro Ser Val Phe Ile Phe Pro Pro
    850                 855                 860

Ser Asp Glu Gln Leu Lys Ser Gly Thr Ala Ser Val Val Cys Leu Leu
865                 870                 875                 880

Asn Asn Phe Tyr Pro Arg Glu Ala Lys Val Gln Trp Lys Val Asp Asn
                885                 890                 895

Ala Leu Gln Ser Gly Asn Ser Gln Glu Ser Val Thr Glu Gln Asp Ser
            900                 905                 910

Lys Asp Ser Thr Tyr Ser Leu Ser Ser Thr Leu Thr Leu Ser Lys Ala
        915                 920                 925

Asp Tyr Glu Lys His Lys Val Tyr Ala Cys Glu Val Thr His Gln Gly
    930                 935                 940

Leu Ser Ser Pro Val Thr Lys Ser Phe Asn Arg Gly Glu Cys Gly Leu
945                 950                 955                 960

Val Pro Arg Gly Ser Gly Ser Gly Gly Gly Ser Gly Gly Gly Ser Glu
                965                 970                 975

Gly Gly Gly Ser Glu Gly Gly Gly Ser Glu Gly Gly Gly Ser Glu Gly
            980                 985                 990

Gly Gly Ser Gly Gly Gly Ser Gly  Gly Leu Val Pro Arg  Gly Ser Glu
        995                 1000                1005

Val Gln  Leu Val Glu Ser Gly  Gly Gly Leu Val Gln  Pro Gly Gly
    1010                1015                1020
```

```
Ser Leu  Arg Leu Ser Cys Ala  Ala Ser Gly Phe Asn  Ile Lys Asp
    1025                 1030                 1035

Thr Tyr  Ile His Trp Val Arg  Gln Ala Pro Gly Lys  Gly Leu Glu
    1040                 1045                 1050

Trp Val  Ala Arg Ile Tyr Pro  Thr Asn Gly Tyr Thr  Arg Tyr Ala
    1055                 1060                 1065

Asp Ser  Val Lys Gly Arg Phe  Thr Ile Ser Ala Asp  Thr Ser Lys
    1070                 1075                 1080

Asn Thr  Ala Tyr Leu Gln Met  Asn Ser Leu Arg Ala  Glu Asp Thr
    1085                 1090                 1095

Ala Val  Tyr Tyr Cys Ser Arg  Trp Gly Gly Asp Gly  Phe Tyr Ala
    1100                 1105                 1110

Met Asp  Tyr Trp Gly Gln Gly  Thr Leu Val Thr Val  Ser Ser Ala
    1115                 1120                 1125

Ser Thr  Lys Gly Pro Ser Val  Phe Pro Leu Ala Pro  Ser Ser Lys
    1130                 1135                 1140

Ser Thr  Ser Gly Gly Thr Ala  Ala Leu Gly Cys Leu  Val Lys Asp
    1145                 1150                 1155

Tyr Phe  Pro Glu Pro Val Thr  Val Ser Trp Asn Ser  Gly Ala Leu
    1160                 1165                 1170

Thr Ser  Gly Val His Thr Phe  Pro Ala Val Leu Gln  Ser Ser Gly
    1175                 1180                 1185

Leu Tyr  Ser Leu Ser Ser Val  Val Thr Val Pro Ser  Ser Ser Leu
    1190                 1195                 1200

Gly Thr  Gln Thr Tyr Ile Cys  Asn Val Asn His Lys  Pro Ser Asn
    1205                 1210                 1215

Thr Lys  Val Asp Lys Lys Val  Glu Pro Lys Ser Cys
    1220                 1225                 1230


<210> SEQ ID NO 12
<211> LENGTH: 1231
<212> TYPE: PRT
<213> ORGANISM: Artificial Sequence
<220> FEATURE:
<223> OTHER INFORMATION: Light chain (Dara)-sc36TMB linker-Heavy chain
      (Dara)-Fc region (Knob) - C-linker - Light chain (Atez)-sc36TMB
      linker-Heavy chain (Atez)

<400> SEQUENCE: 12

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
```

```
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys Gly Leu Val Pro Arg Gly Ser
225                 230                 235                 240

Gly Ser Gly Gly Gly Ser Gly Gly Gly Ser Glu Gly Gly Gly Ser Glu
                245                 250                 255

Gly Gly Gly Ser Glu Gly Gly Gly Ser Glu Gly Gly Gly Ser Gly Gly
            260                 265                 270

Gly Ser Gly Gly Leu Val Pro Arg Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Val Ser Gly Phe Thr Phe Asn Ser Phe Ala Met Ser Trp Val Arg
305                 310                 315                 320

Gln Ala Pro Gly Lys Gly Leu Glu Trp Val Ser Ala Ile Ser Gly Ser
                325                 330                 335

Gly Gly Gly Thr Tyr Tyr Ala Asp Ser Val Lys Gly Arg Phe Thr Ile
            340                 345                 350

Ser Arg Asp Asn Ser Lys Asn Thr Leu Tyr Leu Gln Met Asn Ser Leu
        355                 360                 365

Arg Ala Glu Asp Thr Ala Val Tyr Phe Cys Ala Lys Asp Lys Ile Leu
    370                 375                 380

Trp Phe Gly Glu Pro Val Phe Asp Tyr Trp Gly Gln Gly Thr Leu Val
385                 390                 395                 400

Thr Val Ser Ser Ala Ser Thr Lys Gly Pro Ser Val Phe Pro Leu Ala
                405                 410                 415

Pro Ser Ser Lys Ser Thr Ser Gly Gly Thr Ala Ala Leu Gly Cys Leu
            420                 425                 430

Val Lys Asp Tyr Phe Pro Glu Pro Val Thr Val Ser Trp Asn Ser Gly
        435                 440                 445

Ala Leu Thr Ser Gly Val His Thr Phe Pro Ala Val Leu Gln Ser Ser
    450                 455                 460

Gly Leu Tyr Ser Leu Ser Ser Val Val Thr Val Pro Ser Ser Ser Leu
465                 470                 475                 480

Gly Thr Gln Thr Tyr Ile Cys Asn Val Asn His Lys Pro Ser Asn Thr
                485                 490                 495

Lys Val Asp Lys Lys Val Glu Pro Lys Ser Cys Asp Lys Thr His Thr
            500                 505                 510

Cys Pro Pro Cys Pro Ala Pro Glu Leu Leu Gly Gly Pro Ser Val Phe
        515                 520                 525

Leu Phe Pro Pro Lys Pro Lys Asp Thr Leu Met Ile Ser Arg Thr Pro
    530                 535                 540

Glu Val Thr Cys Val Val Val Asp Val Ser His Glu Asp Pro Glu Val
545                 550                 555                 560
```

```
Lys Phe Asn Trp Tyr Val Asp Gly Val Glu Val His Asn Ala Lys Thr
                565                 570                 575

Lys Pro Arg Glu Glu Gln Tyr Asn Ser Thr Tyr Arg Val Val Ser Val
            580                 585                 590

Leu Thr Val Leu His Gln Asp Trp Leu Asn Gly Lys Glu Tyr Lys Cys
        595                 600                 605

Lys Val Ser Asn Lys Ala Leu Pro Ala Pro Ile Glu Lys Thr Ile Ser
    610                 615                 620

Lys Ala Lys Gly Gln Pro Arg Glu Pro Gln Val Tyr Thr Leu Pro Pro
625                 630                 635                 640

Cys Arg Asp Glu Leu Thr Lys Asn Gln Val Ser Leu Trp Cys Leu Val
                645                 650                 655

Lys Gly Phe Tyr Pro Ser Asp Ile Ala Val Glu Trp Glu Ser Asn Gly
            660                 665                 670

Gln Pro Glu Asn Asn Tyr Lys Thr Thr Pro Pro Val Leu Asp Ser Asp
        675                 680                 685

Gly Ser Phe Phe Leu Tyr Ser Lys Leu Thr Val Asp Lys Ser Arg Trp
    690                 695                 700

Gln Gln Gly Asn Val Phe Ser Cys Ser Val Met His Glu Ala Leu His
705                 710                 715                 720

Asn His Tyr Thr Gln Lys Ser Leu Ser Leu Ser Pro Gly Lys Gly Gly
                725                 730                 735

Gly Ser Gly Gly Gly Ser Gly Gly Gly Ser Gly Asp Ile Gln Met Thr
            740                 745                 750

Gln Ser Pro Ser Ser Leu Ser Ala Ser Val Gly Asp Arg Val Thr Ile
        755                 760                 765

Thr Cys Arg Ala Ser Gln Asp Val Ser Thr Ala Val Ala Trp Tyr Gln
    770                 775                 780

Gln Lys Pro Gly Lys Ala Pro Lys Leu Leu Ile Tyr Ser Ala Ser Phe
785                 790                 795                 800

Leu Tyr Ser Gly Val Pro Ser Arg Phe Ser Gly Ser Gly Ser Gly Thr
                805                 810                 815

Asp Phe Thr Leu Thr Ile Ser Ser Leu Gln Pro Glu Asp Phe Ala Thr
            820                 825                 830

Tyr Tyr Cys Gln Gln Tyr Leu Tyr His Pro Ala Thr Phe Gly Gln Gly
        835                 840                 845

Thr Lys Val Glu Ile Lys Arg Thr Val Ala Ala Pro Ser Val Phe Ile
    850                 855                 860

Phe Pro Pro Ser Asp Glu Gln Leu Lys Ser Gly Thr Ala Ser Val Val
865                 870                 875                 880

Cys Leu Leu Asn Asn Phe Tyr Pro Arg Glu Ala Lys Val Gln Trp Lys
                885                 890                 895

Val Asp Asn Ala Leu Gln Ser Gly Asn Ser Gln Glu Ser Val Thr Glu
            900                 905                 910

Gln Asp Ser Lys Asp Ser Thr Tyr Ser Leu Ser Ser Thr Leu Thr Leu
        915                 920                 925

Ser Lys Ala Asp Tyr Glu Lys His Lys Val Tyr Ala Cys Glu Val Thr
    930                 935                 940

His Gln Gly Leu Ser Ser Pro Val Thr Lys Ser Phe Asn Arg Gly Glu
945                 950                 955                 960

Cys Gly Leu Val Pro Arg Gly Ser Gly Ser Gly Gly Gly Ser Gly Gly
                965                 970                 975
```

```
Gly Ser Glu Gly Gly Gly Ser Glu Gly Gly Gly Ser Glu Gly Gly Gly
            980                 985                 990

Ser Glu Gly Gly Gly Ser Gly Gly  Gly Ser Gly Gly Leu  Val Pro Arg
        995                 1000                1005

Gly Ser  Glu Val Gln Leu Val  Glu Ser Gly Gly Gly  Leu Val Gln
    1010                 1015                 1020

Pro Gly  Gly Ser Leu Arg Leu  Ser Cys Ala Ala Ser  Gly Phe Thr
    1025                 1030                 1035

Phe Ser  Asp Ser Trp Ile His  Trp Val Arg Gln Ala  Pro Gly Lys
    1040                 1045                 1050

Gly Leu  Glu Trp Val Ala Trp  Ile Ser Pro Tyr Gly  Gly Ser Thr
    1055                 1060                 1065

Tyr Tyr  Ala Asp Ser Val Lys  Gly Arg Phe Thr Ile  Ser Ala Asp
    1070                 1075                 1080

Thr Ser  Lys Asn Thr Ala Tyr  Leu Gln Met Asn Ser  Leu Arg Ala
    1085                 1090                 1095

Glu Asp  Thr Ala Val Tyr Tyr  Cys Ala Arg Arg His  Trp Pro Gly
    1100                 1105                 1110

Gly Phe  Asp Tyr Trp Gly Gln  Gly Thr Leu Val Thr  Val Ser Ser
    1115                 1120                 1125

Ala Ser  Thr Lys Gly Pro Ser  Val Phe Pro Leu Ala  Pro Ser Ser
    1130                 1135                 1140

Lys Ser  Thr Ser Gly Gly Thr  Ala Ala Leu Gly Cys  Leu Val Lys
    1145                 1150                 1155

Asp Tyr  Phe Pro Glu Pro Val  Thr Val Ser Trp Asn  Ser Gly Ala
    1160                 1165                 1170

Leu Thr  Ser Gly Val His Thr  Phe Pro Ala Val Leu  Gln Ser Ser
    1175                 1180                 1185

Gly Leu  Tyr Ser Leu Ser Ser  Val Val Thr Val Pro  Ser Ser Ser
    1190                 1195                 1200

Leu Gly  Thr Gln Thr Tyr Ile  Cys Asn Val Asn His  Lys Pro Ser
    1205                 1210                 1215

Asn Thr  Lys Val Asp Lys Lys  Val Glu Pro Lys Ser  Cys
    1220                 1225                 1230
```

<210> SEQ ID NO 13
<211> LENGTH: 108
<212> TYPE: PRT
<213> ORGANISM: Artificial Sequence
<220> FEATURE:
<223> OTHER INFORMATION: VL (Ipil) of SEQ ID NO: 1

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

Trp Thr Phe Gly Gln Gly Thr Lys Val Glu Ile Lys
100 105

<210> SEQ ID NO 14
<211> LENGTH: 107
<212> TYPE: PRT
<213> ORGANISM: Artificial Sequence
<220> FEATURE:
<223> OTHER INFORMATION: CL (Ipil) of of SEQ ID NO: 1

<400> SEQUENCE: 14

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 15
<211> LENGTH: 118
<212> TYPE: PRT
<213> ORGANISM: Artificial Sequence
<220> FEATURE:
<223> OTHER INFORMATION: VH (Ipil) of SEQ ID NO: 1

<400> SEQUENCE: 15

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Thr Met His Trp Val Arg Gln Ala Pro Gly Lys Gly Leu Glu Trp Val
35 40 45

Thr Phe Ile Ser Tyr Asp Gly Asn Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Tyr Cys
85 90 95

Ala Arg Thr Gly Trp Leu Gly Pro Phe Asp Tyr Trp Gly Gln Gly Thr
100 105 110

Leu Val Thr Val Ser Ser
115

<210> SEQ ID NO 16
<211> LENGTH: 330
<212> TYPE: PRT
<213> ORGANISM: Artificial Sequence
<220> FEATURE:
<223> OTHER INFORMATION: CH1 and Fc region of SEQ ID NO: 1

<400> SEQUENCE: 16

Ala Ser Thr Lys Gly Pro Ser Val Phe Pro Leu Ala Pro Ser Ser Lys

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 17
<211> LENGTH: 107
<212> TYPE: PRT
<213> ORGANISM: Artificial Sequence
<220> FEATURE:
<223> OTHER INFORMATION: VL (Dara) of SEQ ID NO: 2

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

```
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105


<210> SEQ ID NO 18
<211> LENGTH: 107
<212> TYPE: PRT
<213> ORGANISM: Artificial Sequence
<220> FEATURE:
<223> OTHER INFORMATION: CL (Dara) of SEQ ID NO: 2

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 19
<211> LENGTH: 122
<212> TYPE: PRT
<213> ORGANISM: Artificial Sequence
<220> FEATURE:
<223> OTHER INFORMATION: VH (Dara) of SEQ ID NO: 2

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120
```

<210> SEQ ID NO 20
<211> LENGTH: 330
<212> TYPE: PRT
<213> ORGANISM: Artificial Sequence
<220> FEATURE:
<223> OTHER INFORMATION: CH1 and Fc region of SEQ ID NO: 2

<400> SEQUENCE: 20

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 21
<211> LENGTH: 108
<212> TYPE: PRT
<213> ORGANISM: Artificial Sequence
<220> FEATURE:

<223> OTHER INFORMATION: VL (Ipil) of SEQ ID NO: 3

<400> SEQUENCE: 21

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Gly Ser Ser
20 25 30

Tyr Leu Ala Trp Tyr Gln Gln Lys Pro Gly Gln Ala Pro Arg Leu Leu
35 40 45

Ile Tyr Gly Ala Phe Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 22
<211> LENGTH: 107
<212> TYPE: PRT
<213> ORGANISM: Artificial Sequence
<220> FEATURE:
<223> OTHER INFORMATION: CL (Ipil) of of SEQ ID NO: 3

<400> SEQUENCE: 22

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 23
<211> LENGTH: 118
<212> TYPE: PRT
<213> ORGANISM: Artificial Sequence
<220> FEATURE:
<223> OTHER INFORMATION: VH (Ipil) of SEQ ID NO: 3

<400> SEQUENCE: 23

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Thr Met His Trp Val Arg Gln Ala Pro Gly Lys Gly Leu Glu Trp Val
35 40 45

Thr Phe Ile Ser Tyr Asp Gly Asn Asn Lys Tyr Tyr Ala Asp Ser Val
50 55 60

Lys Gly Arg Phe Thr Ile Ser Arg Asp Asn Ser Lys Asn Thr Leu Tyr

```
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115


<210> SEQ ID NO 24
<211> LENGTH: 330
<212> TYPE: PRT
<213> ORGANISM: Artificial Sequence
<220> FEATURE:
<223> OTHER INFORMATION: CH1 and Fc region (Hole) of SEQ ID NO: 3

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

305 310 315 320

Gln Lys Ser Leu Ser Leu Ser Pro Gly Lys
325 330

<210> SEQ ID NO 25
<211> LENGTH: 107
<212> TYPE: PRT
<213> ORGANISM: Artificial Sequence
<220> FEATURE:
<223> OTHER INFORMATION: VL (Dara) of SEQ ID NO: 4

<400> SEQUENCE: 25

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Thr Phe Gly Gln Gly Thr Lys Val Glu Ile Lys
100 105

<210> SEQ ID NO 26
<211> LENGTH: 107
<212> TYPE: PRT
<213> ORGANISM: Artificial Sequence
<220> FEATURE:
<223> OTHER INFORMATION: CL (Dara) of SEQ ID NO: 4

<400> SEQUENCE: 26

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 27
<211> LENGTH: 122
<212> TYPE: PRT
<213> ORGANISM: Artificial Sequence
<220> FEATURE:
<223> OTHER INFORMATION: VH (Dara) of SEQ ID NO: 4

<400> SEQUENCE: 27

Glu Val Gln Leu Leu Glu Ser Gly Gly Gly Leu Val Gln Pro Gly Gly
1 5 10 15

Ser Leu Arg Leu Ser Cys Ala Val Ser Gly Phe Thr Phe Asn Ser Phe
20 25 30

Ala Met Ser Trp Val Arg Gln Ala Pro Gly Lys Gly Leu Glu Trp Val
35 40 45

Ser Ala Ile Ser Gly Ser Gly Gly Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys
85 90 95

Ala Lys Asp Lys Ile Leu Trp Phe Gly Glu Pro Val Phe Asp Tyr Trp
100 105 110

Gly Gln Gly Thr Leu Val Thr Val Ser Ser
115 120

<210> SEQ ID NO 28
<211> LENGTH: 330
<212> TYPE: PRT
<213> ORGANISM: Artificial Sequence
<220> FEATURE:
<223> OTHER INFORMATION: CH1 and Fc region (Knob) of SEQ ID NO: 4

<400> SEQUENCE: 28

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Cys Arg Asp Glu
225 230 235 240

Leu Thr Lys Asn Gln Val Ser Leu Trp Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 29
<211> LENGTH: 107
<212> TYPE: PRT
<213> ORGANISM: Artificial Sequence
<220> FEATURE:
<223> OTHER INFORMATION: VL (Her) of SEQ ID NO: 5

<400> SEQUENCE: 29

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys
100 105

<210> SEQ ID NO 30
<211> LENGTH: 107
<212> TYPE: PRT
<213> ORGANISM: Artificial Sequence
<220> FEATURE:
<223> OTHER INFORMATION: CL (Her) of SEQ ID NO: 5

<400> SEQUENCE: 30

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

```
<210> SEQ ID NO 31
<211> LENGTH: 120
<212> TYPE: PRT
<213> ORGANISM: Artificial Sequence
<220> FEATURE:
<223> OTHER INFORMATION: VH (Her) of SEQ ID NO: 5

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 32
<211> LENGTH: 330
<212> TYPE: PRT
<213> ORGANISM: Artificial Sequence
<220> FEATURE:
<223> OTHER INFORMATION: CH1 and Fc region (Knob) of SEQ ID NO: 5

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Cys Arg Asp Glu
225 230 235 240

Leu Thr Lys Asn Gln Val Ser Leu Trp Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 33
<211> LENGTH: 108
<212> TYPE: PRT
<213> ORGANISM: Artificial Sequence
<220> FEATURE:
<223> OTHER INFORMATION: VL (Ipil) of SEQ ID NO: 6

<400> SEQUENCE: 33

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Gly Ser Ser
20 25 30

Tyr Leu Ala Trp Tyr Gln Gln Lys Pro Gly Gln Ala Pro Arg Leu Leu
35 40 45

Ile Tyr Gly Ala Phe Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 34
<211> LENGTH: 107
<212> TYPE: PRT
<213> ORGANISM: Artificial Sequence
<220> FEATURE:
<223> OTHER INFORMATION: CL (Ipil) of SEQ ID NO: 6

<400> SEQUENCE: 34

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 35
<211> LENGTH: 73
<212> TYPE: PRT
<213> ORGANISM: Artificial Sequence
<220> FEATURE:
<223> OTHER INFORMATION: sc36TMB linker Twin Strep tag of SEQ ID NO: 6

<400> SEQUENCE: 35

Gly Leu Val Pro Arg Gly Ser Gly Ser Gly Gly Gly Ser Glu Gly Gly
1 5 10 15

Gly Ser Glu Gly Gly Trp Ser His Pro Gln Phe Glu Lys Gly Gly Gly
20 25 30

Ser Gly Gly Gly Ser Gly Gly Ser Ala Trp Ser His Pro Gln Phe Glu
35 40 45

Lys Gly Ser Glu Gly Gly Gly Ser Glu Gly Gly Gly Ser Gly Gly Gly
50 55 60

Ser Gly Gly Leu Val Pro Arg Gly Ser
65 70

<210> SEQ ID NO 36
<211> LENGTH: 118
<212> TYPE: PRT
<213> ORGANISM: Artificial Sequence
<220> FEATURE:
<223> OTHER INFORMATION: VH (Ipil) of SEQ ID NO: 6

<400> SEQUENCE: 36

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Thr Met His Trp Val Arg Gln Ala Pro Gly Lys Gly Leu Glu Trp Val
35 40 45

Thr Phe Ile Ser Tyr Asp Gly Asn Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Tyr Cys
85 90 95

Ala Arg Thr Gly Trp Leu Gly Pro Phe Asp Tyr Trp Gly Gln Gly Thr
100 105 110

Leu Val Thr Val Ser Ser
115

<210> SEQ ID NO 37
<211> LENGTH: 330
<212> TYPE: PRT
<213> ORGANISM: Artificial Sequence
<220> FEATURE:
<223> OTHER INFORMATION: CH1 and Fc region (Hole) of SEQ ID NO: 6

<400> SEQUENCE: 37

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 38
<211> LENGTH: 107
<212> TYPE: PRT
<213> ORGANISM: Artificial Sequence
<220> FEATURE:
<223> OTHER INFORMATION: VL (Dara) of SEQ ID NO: 7

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Thr Phe Gly Gln Gly Thr Lys Val Glu Ile Lys
100 105

<210> SEQ ID NO 39
<211> LENGTH: 107
<212> TYPE: PRT
<213> ORGANISM: Artificial Sequence
<220> FEATURE:
<223> OTHER INFORMATION: CL (Dara) of SEQ ID NO: 7

<400> SEQUENCE: 39

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 40
<211> LENGTH: 51
<212> TYPE: PRT
<213> ORGANISM: Artificial Sequence
<220> FEATURE:
<223> OTHER INFORMATION: sc36TMB linker 10xHisTag of SEQ ID NO: 7

<400> SEQUENCE: 40

Gly Leu Val Pro Arg Gly Ser Gly Ser Gly Gly Gly Ser Gly Gly Gly
1 5 10 15

Ser His His His His His His His His His His Gly Gly Gly Ser Gly
20 25 30

Gly Gly Ser Gly Gly Gly Ser Gly Gly Gly Ser Gly Gly Leu Val Pro
35 40 45

Arg Gly Ser
50

<210> SEQ ID NO 41
<211> LENGTH: 122
<212> TYPE: PRT
<213> ORGANISM: Artificial Sequence
<220> FEATURE:
<223> OTHER INFORMATION: VH (DARA) OF SEQ ID NO: 7

<400> SEQUENCE: 41

Glu Val Gln Leu Leu Glu Ser Gly Gly Gly Leu Val Gln Pro Gly Gly

```
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120


<210> SEQ ID NO 42
<211> LENGTH: 330
<212> TYPE: PRT
<213> ORGANISM: Artificial Sequence
<220> FEATURE:
<223> OTHER INFORMATION: CH1 and Fc region (Knob) of SEQ ID NO: 7

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
```

```
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 43
<211> LENGTH: 107
<212> TYPE: PRT
<213> ORGANISM: Artificial Sequence
<220> FEATURE:
<223> OTHER INFORMATION: VL (Her) of SEQ ID NO: 8

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 44
<211> LENGTH: 107
<212> TYPE: PRT
<213> ORGANISM: Artificial Sequence
<220> FEATURE:
<223> OTHER INFORMATION: CL (Her) of SEQ ID NO: 8

<400> SEQUENCE: 44

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 45
<211> LENGTH: 51
<212> TYPE: PRT
<213> ORGANISM: Artificial Sequence
<220> FEATURE:
<223> OTHER INFORMATION: sc36TMB linker 10xHisTag of SEQ ID NO: 8

<400> SEQUENCE: 45

```
Gly Leu Val Pro Arg Gly Ser Gly Ser Gly Gly Gly Ser Gly Gly Gly
1               5                   10                  15

Ser His His His His His His His His His His Gly Gly Gly Ser Gly
            20                  25                  30

Gly Gly Ser Gly Gly Gly Ser Gly Gly Gly Ser Gly Gly Leu Val Pro
        35                  40                  45

Arg Gly Ser
    50
```

<210> SEQ ID NO 46
<211> LENGTH: 120
<212> TYPE: PRT
<213> ORGANISM: Artificial Sequence
<220> FEATURE:
<223> OTHER INFORMATION: VH (Her) of SEQ ID NO: 8

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 47
<211> LENGTH: 330
<212> TYPE: PRT
<213> ORGANISM: Artificial Sequence
<220> FEATURE:
<223> OTHER INFORMATION: CH1 and Fc region (Knob) of SEQ ID NO: 8

<400> SEQUENCE: 47

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 48
<211> LENGTH: 107
<212> TYPE: PRT
<213> ORGANISM: Artificial Sequence
<220> FEATURE:
<223> OTHER INFORMATION: VL (Her) of SEQ ID NO: 9

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
```

100 105

<210> SEQ ID NO 49
<211> LENGTH: 107
<212> TYPE: PRT
<213> ORGANISM: Artificial Sequence
<220> FEATURE:
<223> OTHER INFORMATION: CL (Her) of SEQ ID NO: 9

<400> SEQUENCE: 49

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 50
<211> LENGTH: 120
<212> TYPE: PRT
<213> ORGANISM: Artificial Sequence
<220> FEATURE:
<223> OTHER INFORMATION: VH (Her) of SEQ ID NO: 9

<400> SEQUENCE: 50

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 51
<211> LENGTH: 10
<212> TYPE: PRT
<213> ORGANISM: Artificial Sequence
<220> FEATURE:
<223> OTHER INFORMATION: N-linker of SEQ ID NO: 9

<400> SEQUENCE: 51

Ala Ser Thr Lys Gly Pro Ser Gly Ser Gly
1 5 10

<210> SEQ ID NO 52
<211> LENGTH: 108
<212> TYPE: PRT
<213> ORGANISM: Artificial Sequence
<220> FEATURE:
<223> OTHER INFORMATION: VL (Ipil) of SEQ ID NO: 9

<400> SEQUENCE: 52

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 53
<211> LENGTH: 107
<212> TYPE: PRT
<213> ORGANISM: Artificial Sequence
<220> FEATURE:
<223> OTHER INFORMATION: CL (Ipil) of SEQ ID NO: 9

<400> SEQUENCE: 53

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 54
<211> LENGTH: 118
<212> TYPE: PRT
<213> ORGANISM: Artificial Sequence
<220> FEATURE:
<223> OTHER INFORMATION: VH (Ipil) of SEQ ID NO: 9

<400> SEQUENCE: 54

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115


<210> SEQ ID NO 55
<211> LENGTH: 330
<212> TYPE: PRT
<213> ORGANISM: Artificial Sequence
<220> FEATURE:
<223> OTHER INFORMATION: CH1 and Fc region (Hole) of SEQ ID NO: 9

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 56
<211> LENGTH: 107
<212> TYPE: PRT
<213> ORGANISM: Artificial Sequence
<220> FEATURE:
<223> OTHER INFORMATION: VL (Atez) of SEQ ID NO: 10

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105


<210> SEQ ID NO 57
<211> LENGTH: 107
<212> TYPE: PRT
<213> ORGANISM: Artificial Sequence
<220> FEATURE:
<223> OTHER INFORMATION: CL (Atez) of SEQ ID NO: 10

<400> SEQUENCE: 57

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 58
<211> LENGTH: 118
<212> TYPE: PRT
<213> ORGANISM: Artificial Sequence
```

<220> FEATURE:
<223> OTHER INFORMATION: VH (Atez) of SEQ ID NO: 10

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 59
<211> LENGTH: 10
<212> TYPE: PRT
<213> ORGANISM: Artificial Sequence
<220> FEATURE:
<223> OTHER INFORMATION: N-linker of SEQ ID NO: 10

<400> SEQUENCE: 59

Ala Ser Thr Lys Gly Pro Ser Gly Ser Gly
1               5                   10

<210> SEQ ID NO 60
<211> LENGTH: 107
<212> TYPE: PRT
<213> ORGANISM: Artificial Sequence
<220> FEATURE:
<223> OTHER INFORMATION: VL (Dara) of SEQ ID NO: 10

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 61
<211> LENGTH: 107
<212> TYPE: PRT
<213> ORGANISM: Artificial Sequence
<220> FEATURE:

<223> OTHER INFORMATION: CL (Dara) of SEQ ID NO: 10

<400> SEQUENCE: 61

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 62
<211> LENGTH: 122
<212> TYPE: PRT
<213> ORGANISM: Artificial Sequence
<220> FEATURE:
<223> OTHER INFORMATION: VH (Dara) of SEQ ID NO: 10

<400> SEQUENCE: 62

Glu Val Gln Leu Leu Glu Ser Gly Gly Gly Leu Val Gln Pro Gly Gly
1 5 10 15

Ser Leu Arg Leu Ser Cys Ala Val Ser Gly Phe Thr Phe Asn Ser Phe
20 25 30

Ala Met Ser Trp Val Arg Gln Ala Pro Gly Lys Gly Leu Glu Trp Val
35 40 45

Ser Ala Ile Ser Gly Ser Gly Gly Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys
85 90 95

Ala Lys Asp Lys Ile Leu Trp Phe Gly Glu Pro Val Phe Asp Tyr Trp
100 105 110

Gly Gln Gly Thr Leu Val Thr Val Ser Ser
115 120

<210> SEQ ID NO 63
<211> LENGTH: 330
<212> TYPE: PRT
<213> ORGANISM: Artificial Sequence
<220> FEATURE:
<223> OTHER INFORMATION: CH1 and Fc region (Knob) of SEQ ID NO: 10

<400> SEQUENCE: 63

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser

```
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Cys Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 64
<211> LENGTH: 108
<212> TYPE: PRT
<213> ORGANISM: Artificial Sequence
<220> FEATURE:
<223> OTHER INFORMATION: VL (Ipil) of SEQ ID NO: 11

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
```

```
                85                  90                  95

Trp Thr Phe Gly Gln Gly Thr Lys Val Glu Ile Lys
            100                 105


<210> SEQ ID NO 65
<211> LENGTH: 107
<212> TYPE: PRT
<213> ORGANISM: Artificial Sequence
<220> FEATURE:
<223> OTHER INFORMATION: CL (Ipil) of SEQ ID NO: 11

<400> SEQUENCE: 65

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 66
<211> LENGTH: 118
<212> TYPE: PRT
<213> ORGANISM: Artificial Sequence
<220> FEATURE:
<223> OTHER INFORMATION: VH (Ipil) of SEQ ID NO: 11

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115


<210> SEQ ID NO 67
<211> LENGTH: 330
<212> TYPE: PRT
<213> ORGANISM: Artificial Sequence
<220> FEATURE:
<223> OTHER INFORMATION: CH1 and Fc region (Hole) of SEQ ID NO: 11

<400> SEQUENCE: 67
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 68
<211> LENGTH: 13
<212> TYPE: PRT
<213> ORGANISM: Artificial Sequence
<220> FEATURE:
<223> OTHER INFORMATION: C-linker of SEQ ID NO: 11

<400> SEQUENCE: 68

```
Gly Gly Gly Ser Gly Gly Gly Ser Gly Gly Gly Ser Gly
1               5                   10
```

<210> SEQ ID NO 69

<211> LENGTH: 107
<212> TYPE: PRT
<213> ORGANISM: Artificial Sequence
<220> FEATURE:
<223> OTHER INFORMATION: VL (Her) of SEQ ID NO: 11

<400> SEQUENCE: 69

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 70
<211> LENGTH: 107
<212> TYPE: PRT
<213> ORGANISM: Artificial Sequence
<220> FEATURE:
<223> OTHER INFORMATION: CL (Her) of SEQ ID NO: 11

<400> SEQUENCE: 70

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 71
<211> LENGTH: 120
<212> TYPE: PRT
<213> ORGANISM: Artificial Sequence
<220> FEATURE:
<223> OTHER INFORMATION: VH (Her) of SEQ ID NO: 11

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 72
<211> LENGTH: 108
<212> TYPE: PRT
<213> ORGANISM: Artificial Sequence
<220> FEATURE:
<223> OTHER INFORMATION: VL (Dara) of SEQ ID NO: 12

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg
            100                 105


<210> SEQ ID NO 73
<211> LENGTH: 106
<212> TYPE: PRT
<213> ORGANISM: Artificial Sequence
<220> FEATURE:
<223> OTHER INFORMATION: CL (Dara) of SEQ ID NO: 12

<400> SEQUENCE: 73

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 74
```

<211> LENGTH: 122
<212> TYPE: PRT
<213> ORGANISM: Artificial Sequence
<220> FEATURE:
<223> OTHER INFORMATION: VH (Dara 1) of SEQ ID NO: 12

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120
```

<210> SEQ ID NO 75
<211> LENGTH: 330
<212> TYPE: PRT
<213> ORGANISM: Artificial Sequence
<220> FEATURE:
<223> OTHER INFORMATION: CH1 and Fc region (Knob) of SEQ ID NO: 12

<400> SEQUENCE: 75

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Cys Arg Asp Glu
225 230 235 240

Leu Thr Lys Asn Gln Val Ser Leu Trp Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 76
<211> LENGTH: 13
<212> TYPE: PRT
<213> ORGANISM: Artificial Sequence
<220> FEATURE:
<223> OTHER INFORMATION: C-linker of SEQ ID NO: 12

<400> SEQUENCE: 76

Gly Gly Gly Ser Gly Gly Gly Ser Gly Gly Gly Ser Gly
1 5 10

<210> SEQ ID NO 77
<211> LENGTH: 107
<212> TYPE: PRT
<213> ORGANISM: Artificial Sequence
<220> FEATURE:
<223> OTHER INFORMATION: VL (Atez) of SEQ ID NO: 12

<400> SEQUENCE: 77

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Leu Tyr His Pro Ala
85 90 95

Thr Phe Gly Gln Gly Thr Lys Val Glu Ile Lys
100 105

<210> SEQ ID NO 78
<211> LENGTH: 107
<212> TYPE: PRT
<213> ORGANISM: Artificial Sequence
<220> FEATURE:
<223> OTHER INFORMATION: CL (Atez) of SEQ ID NO: 12

<400> SEQUENCE: 78

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 79
<211> LENGTH: 118
<212> TYPE: PRT
<213> ORGANISM: Artificial Sequence
<220> FEATURE:
<223> OTHER INFORMATION: VH (Atez) of SEQ ID NO: 12

<400> SEQUENCE: 79

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ser
115

<210> SEQ ID NO 80
<211> LENGTH: 49
<212> TYPE: PRT
<213> ORGANISM: Artificial Sequence
<220> FEATURE:
<223> OTHER INFORMATION: sc36TMB linker

<400> SEQUENCE: 80

Gly Leu Val Pro Arg Gly Ser Gly Ser Gly Gly Gly Ser Gly Gly Gly
1 5 10 15

Ser Glu Gly Gly Gly Ser Glu Gly Gly Gly Ser Glu Gly Gly Gly Ser
20 25 30

Glu Gly Gly Gly Ser Gly Gly Gly Ser Gly Gly Leu Val Pro Arg Gly
35 40 45

Ser

<210> SEQ ID NO 81

```
<211> LENGTH: 11
<212> TYPE: PRT
<213> ORGANISM: Artificial Sequence
<220> FEATURE:
<223> OTHER INFORMATION: N-linker

<400> SEQUENCE: 81

Ala Ser Thr Lys Gly Pro Ser Gly Ser Gly Ser
1               5                   10


<210> SEQ ID NO 82
<211> LENGTH: 13
<212> TYPE: PRT
<213> ORGANISM: Artificial Sequence
<220> FEATURE:
<223> OTHER INFORMATION: C-linker

<400> SEQUENCE: 82

Gly Gly Gly Ser Gly Gly Gly Ser Gly Gly Gly Ser Gly
1               5                   10


<210> SEQ ID NO 83
<211> LENGTH: 5
<212> TYPE: PRT
<213> ORGANISM: Artificial Sequence
<220> FEATURE:
<223> OTHER INFORMATION: 5-mer peptide

<400> SEQUENCE: 83

Gly Leu Val Pro Arg
1               5
```